United States Patent
Kang et al.

(10) Patent No.: US 12,269,855 B2
(45) Date of Patent: Apr. 8, 2025

(54) INTERLEUKIN-2 AND USE THEREOF

(71) Applicant: INNOVENT BIOLOGICS (SUZHOU) CO., LTD., Jiangsu (CN)

(72) Inventors: Lishan Kang, Jiangsu (CN); Chunyin Gu, Jiangsu (CN); Fenggen Fu, Jiangsu (CN); Shuaixiang Zhou, Jiangsu (CN); Xinzhen Shi, Jiangsu (CN); Junjian Liu, Jiangsu (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 1165 days.

(21) Appl. No.: 17/059,583

(22) PCT Filed: Sep. 20, 2019

(86) PCT No.: PCT/CN2019/107055
§ 371 (c)(1),
(2) Date: Nov. 30, 2020

(87) PCT Pub. No.: WO2020/057646
PCT Pub. Date: Mar. 26, 2020

(65) Prior Publication Data
US 2021/0221863 A1    Jul. 22, 2021

(30) Foreign Application Priority Data

Sep. 21, 2018   (CN) .......................... 201811108649.X

(51) Int. Cl.
| C07K 14/55 | (2006.01) |
| A61K 38/00 | (2006.01) |
| A61K 47/68 | (2017.01) |
| C07K 16/18 | (2006.01) |
| C07K 16/24 | (2006.01) |
| C07K 16/30 | (2006.01) |
| C07K 16/40 | (2006.01) |
| C12P 21/02 | (2006.01) |

(52) U.S. Cl.
CPC .......... *C07K 14/55* (2013.01); *A61K 47/6843* (2017.08); *A61K 47/6845* (2017.08); *A61K 47/6853* (2017.08); *A61K 47/6865* (2017.08); *A61K 47/6871* (2017.08); *C07K 16/18* (2013.01); *C07K 16/248* (2013.01); *C07K 16/3007* (2013.01); *C07K 16/3053* (2013.01); *C07K 16/40* (2013.01); *C12P 21/02* (2013.01); *A61K 38/00* (2013.01); *C07K 2317/55* (2013.01); *C07K 2317/56* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| 4,518,584 | A | 5/1985 | Mark et al. |
| 5,153,310 | A | 10/1992 | Mitchell et al. |
| 6,171,586 | B1 | 1/2001 | Lam et al. |
| 6,207,156 | B1 | 3/2001 | Kuchroo et al. |
| 6,267,958 | B1 | 7/2001 | Andya et al. |
| 9,244,059 | B2 | 1/2016 | Triebel et al. |
| 11,111,312 | B2 | 9/2021 | Ast et al. |
| 2011/0070238 | A1 | 3/2011 | Triebel et al. |
| 2011/0150892 | A1 | 6/2011 | Thudium et al. |
| 2012/0244112 | A1 | 9/2012 | Ast et al. |
| 2018/0142037 | A1 | 5/2018 | Ast et al. |
| 2018/0326010 | A1 | 11/2018 | Codarri et al. |
| 2021/0213102 | A1 | 7/2021 | Kang et al. |
| 2021/0269497 | A1 | 9/2021 | Li et al. |
| 2023/0145766 | A1 | 5/2023 | He et al. |
| 2023/0174604 | A1 | 6/2023 | Fu et al. |

FOREIGN PATENT DOCUMENTS

| CA | 3040313 | | 5/2018 |
| CN | 1309705 | A | 8/2001 |
| CN | 102101885 | A1 | 6/2011 |
| CN | 103492411 | A | 1/2014 |
| CN | 104231068 | A | 12/2014 |
| CN | 105980410 | A | 9/2016 |
| CN | 110003339 | A | 7/2019 |
| CN | 110382525 | A | 10/2019 |

(Continued)

OTHER PUBLICATIONS

Tilly et al., Identification of a Small Molecule Inhibitor of the IL-2/IL-2Rα Receptor Interaction Which Binds to IL-2. Journal of the American Chemical Society 119 (32): 7589-7590, 1997.*
Lenardo: "Interleukin-2 programs mouse αβ T lymphocytes for apoptosis", Nature 353: 858 (1991).
Estep et al., "High throughput solution based measurement of antibody-antigen affinity and epitope binning". MAbs, 2013, 5(2): pp. 270-278.
Denesyuk et al., Molecular models of two competitive inhibitors, IL-2δ2 and IL-2δ3, generated by alternative splicing of human interleukin-2, Immunology Letters, 60 (1998) 61-66.
Xu et al., Structure-Function Studies of the C-terminal α-Helix of Human Iterleukin-2 by site-directed mutagenesis, Chinese Journal of Biotechnology, 9(4):298-302, 1993. 23.

(Continued)

*Primary Examiner* — Ruixiang Li
(74) *Attorney, Agent, or Firm* — LEASON ELLIS LLP

(57) ABSTRACT

The present invention relates to a novel interleukin-2 (IL-2) mutant protein and use thereof. In particular, the present invention relates to an IL-2 mutant protein with reduced IL-2Rα receptor binding ability and/or increased IL-2Rβ receptor binding ability compared with the wild-type IL-2. The present invention further provides a fusion protein and an immunoconjugate comprising the IL-2 mutant protein, a nucleic acid encoding the IL-2 mutant protein, and a vector and a host cell comprising the nucleic acid. The present invention further provides a method for preparing the IL-2 mutant protein, a pharmaceutical composition comprising the IL-2 mutant protein, and therapeutic use of the mutant protein.

12 Claims, 9 Drawing Sheets

Specification includes a Sequence Listing.

(56) References Cited

FOREIGN PATENT DOCUMENTS

| | | |
|---|---|---|
| CN | 110392692 A | 10/2019 |
| CN | 111655718 A | 9/2020 |
| CN | 111868079 A | 10/2020 |
| EP | 4273161 A1 | 11/2023 |
| JP | H04-503604 A | 7/1992 |
| JP | 2007-527242 A | 9/2007 |
| JP | 2007-528728 A | 10/2007 |
| JP | 2007-535919 A | 12/2007 |
| JP | 2008-509651 A | 4/2008 |
| JP | 2014-506793 A | 3/2014 |
| JP | 2017-500040 A | 1/2017 |
| JP | 2017-518361 A | 7/2017 |
| JP | 2020-529977 A | 10/2020 |
| JP | 2021-531013 A | 11/2021 |
| TW | 201237165 A1 | 9/2012 |
| TW | 201831688 A | 9/2018 |
| TW | 201900220 A | 1/2019 |
| TW | 202014432 A | 4/2020 |
| TW | 202144391 A | 12/2021 |
| WO | 1990/010070 A1 | 9/1990 |
| WO | 91/02000 A1 | 2/1991 |
| WO | 98/42752 A1 | 10/1998 |
| WO | 00/37504 A2 | 6/2000 |
| WO | 01/14424 A2 | 3/2001 |
| WO | 2005/086751 A2 | 9/2005 |
| WO | 2005/086798 A2 | 9/2005 |
| WO | 2005/100395 A2 | 10/2005 |
| WO | 2006/044908 A2 | 4/2006 |
| WO | 2010/021961 A2 | 2/2010 |
| WO | 2010/087994 A2 | 8/2010 |
| WO | 2012/119093 A1 | 9/2012 |
| WO | 2014/008218 A1 | 1/2014 |
| WO | 2017/025016 A1 | 2/2017 |
| WO | 2017024465 A1 | 2/2017 |
| WO | 2019/028419 A1 | 2/2019 |
| WO | 2019/173832 A2 | 9/2019 |
| WO | 2019246404 A1 | 12/2019 |
| WO | 2020/020783 A1 | 1/2020 |
| WO | 2020057645 A1 | 3/2020 |
| WO | 2020247843 A2 | 12/2020 |
| WO | 2020252418 A2 | 12/2020 |
| WO | 2020252421 A2 | 12/2020 |
| WO | 2021185362 A1 | 9/2021 |

OTHER PUBLICATIONS

International Search Report and Written Opinion of PCT/CN2019/107054, mailed on Dec. 20, 2019.

Vidarsson et al., IgG subclasses and allotypes: from structure to effector functions, 2014, Columbe 5, Article 520: 1-17.

Carmenate et al., "Human IL-2 mutein with higher antitumor efficacy than wild type IL-2", The Journal of Immunology, 2013, 190(12): 6230-6238.

Smith et al., "A novel, native-format bispecific antibody triggering T-cell killing of B-cells is robustly active in mouse tumor models and cynomolgus monkeys", Scientific Reports, 2015-5:17943—DOI: 10.1038/srep17943.

International Search Report and Written Opinion of PCT/CN2021/081840, mailed Jul. 1, 2021.

International Search Report and Written Opinion of PCT/CN2021/081841, mailed Jun. 18, 2021.

Chen et al., "A novel human IL2 mutein with minimal systemic toxicity exerts greater antitumor efficacy than wild-type IL2", Cell Death and Disease, 2018, 9:989, pp. 1-12.

Lopes et al: "ALKS 4230: a novel engineered IL-2 fusion protein with an improved cellular selectivity profile for cancer immunotherapy", Journal for Immunotherapy of Cancer, vol. 8, No. 1, 2020:e000673. 13 pages.

Wu et al: "IL-2R[alpha]-biased agonist enhances antitumor immunity by invigorating tumor-infiltrating CD25+CD8+ T cells", Nature Cancer, vol. 4, No. 9, 2023:1309-1325. 35 pages.

Zhang et al.: "Comparative analysis of bat genomes provides insight into the evolution of flight and immunity", Science, 2013, 339(6118): 456-460. 10 pages.

Smith, Science 240, 1169-76 (1988): "Interleukin-2: Inception, Impact, and Implications".

Bazan, Science 257,410-413 (1992): "Unraveling the Structure of IL-2".

Krieg et al., Proc Natl Acad Sci 107, 11906-11 (2010): "Improved IL-2 immunotherapy by selective stimulation of IL-2 receptors on lymphocytes and endothelial cells".

Boyman, O. and Sprent. J. Nat. Rev. Immunol. 12, 180-190 (2012): "The role of interleukin-2 during homeostasis and activation of the immune system".

Fontenot et al., Nature Immunol. 6, 1142-51 (2005): "A function for interleukin 2 in Foxp3-expressing regulatory T cells".

D'Cruz, Klein, Nature Immunol 6, 1152-59 (2005): "Development and function of agonist-induced CD25+Foxp3+ regulatory T cells in the absence of interleukin 2 signaling".

Maloy, Powrie, Nature Immunol. 6,1171-72 (2005): "Fueling regulation: IL-2 keeps CD4+ T reg cells fit".

Boyman et al., Science 311, 1924-1927 (2006): "Selective Stimulation of T Cell Subsets with Antibody-Cytokine Immune Complexes".

Aron M. Levin et al., Nature, vol. 484, p. 529-533, 2012: "Exploiting a natural conformational switch to engineer an interleukin-2 'superkine' ".

Rodrigo Vazquez-Lombardi, et al., Nature Communications, 8:15373, 2017: "Potent antitumour activity of interleukin-2-Fc fusion proteins requires Fc-mediated depletion of regulatory T-cells".

Gerngross, Nat Biotech 22, 1409-1414 (2004): "Advances in the production of human therapeutic proteins in yeasts and filamentous fungi".

Li et al., Nat Biotech 24, 210-215 (2006): "Optimization of humanized IgGs in glycoengineered Pichia pastoris".

Graham et al., J Gen Virol 36,59-72 (1977): "Characteristics of a Human Cell Line Transformed by DNA from Human Adenovirus Type 5".

Mather, Biol Reprod 23,243-252 (1980): "Establishment and Characterization of Two Distinct Mouse Testicular Epithelial Cell Lines".

Mather et al., Annals N. Y. Acad Sci 383,44-68 (1982): "Culture of Testicular Cells in Hormone-Supplemented Serum-Free Medium".

Urlaub et al., Proc Natl Acad Sci USA 77, 4216 (1980): "Isolation of Chinese hamster cell mutants deficient in dihydrofolate reductase activity".

Hurwitz et al. (1998) Proc. Natl. Acad. Sci. USA 95(17): 10067-10071: "CTLA-4 blockade synergizes with tumor-derived granulocyte-macrophage colony-stimulating factor for treatment of an experimental mammary carcinoma".

Camacho et al. (2004) J. Clin. Oncology 22(145): Abstract No. 2505: "Phase 1 clinical trial of anti-CTLA4 human monoclonal antibody CP-675,206 in patients (pts) with advanced solid malignancies".

Mokyr et al. (1998) Cancer Res. 58:5301-5304: "Realization of the Therapeutic Potential of CTLA-4 Blockade in Low-Dose Chemotherapy-treated Tumor-bearing Mice".

Lorenzo Benatuil et al.: "An improved yeast transformation method for the generation of very large human antibody libraries": Protein Engineering, Design & Selection vol. 23 No. 4 pp. 155-159, 2010.

International Search Report and Written Opinion of PCT/CN2019/107055, mailed on Dec. 12, 2019.

International Search Report and Written Opinion of PCT/CN2022/120265, mailed Nov. 25, 2022, including translations. [28 pages].

Kamimura et al. "IL-2 In Vivo Activities and Antitumor Efficacy Enhanced by an Anti-IL-2 mAb1", J. Immunol. 177, 306-14 (2006). [9 pages].

Ren et al. "Selective delivery of low-affinity IL-2 to PD-1+ T cells rejuvenates antitumor immunity with reduced toxicity", The Journal of Clinical Investigation, vol. 132, No. 3, 2022. [13 pages].

U.S. Appl. No. 18/693,453, filed Mar. 19, 2024 [105 pages].

* cited by examiner

Crystal structure of IL-2/IL-2Rα complex

Crystal structure of IL-2/IL-2Rβ complex

Primers used to construct mutant library IBYDL029

| Primer | | N1 | N2 | N3 | | N4 | N5 | N6 | N7 | 3' |
|---|---|---|---|---|---|---|---|---|---|---|
| AMP0 200 | 5' | ATCAACAACTA CAAGAACCCC | AAG | ACT | CGT | ATG CTG | ACC | TTC | AAG | TTT | TAC | ATGCCCAAGAAGGCCAC CGAGCTGAAGCATTTA |
| | | 50% (original amino acid) | K | T | R | ML | T | F | K | F | Y | |
| | | 50% (mutant amino acid) | D,E | D,E,R,K, F,Y,W | D,E,F,Y, W,A,V | | K,R,M,F,Y, W,Q,E | K,R,A, E,Q | E,D,F, Y,W | | R,K | |

According to the table, the original amino acids in N1-N7 are 50%, and the remaining 50% are equally divided by the corresponding mutant amino acids. The codon is preferably saccharomyces cerevisiae; after a forward sequence is designed, the primer is synthesized in a reverse sequence

| Primer | | N1 | N2 | N3 | N4 | 3' |
|---|---|---|---|---|---|---|
| AMP0 201 | 5' | GCCACCGAGCTGAAGC ATTTTACAGTGTTTAGAG | GAG | GAG | CTGAAGCCTTTAGAG | GAG | GTGCTCAAT | TTA | GCCCAGAGC AAGAACTTCC |
| | | 50% (original amino acid) | E | E | LKPLE | E | VLN | L | |
| | | 50% (mutant amino acid) | R,K,W,Y,L | R,K,W,Y | | R,K,W,Y | | R,K,F,Y,W | |

According to the table, the original amino acids in N1-N4 are 50%, and the remaining 50% are equally divided by the corresponding mutant amino acids. The codon is preferably saccharomyces cerevisiae; the primer is synthesized in a forward sequence

FIG. 3A

Primers used to construct mutant libraries IBYDL030 and 031

| Primer | | N1 | N2 | | N3 | N4 | | N5 | N6 | | N7 | |
|---|---|---|---|---|---|---|---|---|---|---|---|---|
| | 5' | CTG | CAG | CTG | GAG | CAT | TTA CTG | CTG | GAT | TTACAG | ATG | GCAGCA CCAAGA AGACCC AG | ATTTTAAACG GCATCAACA ACTAC 3' |
| AMP0 222 | | 50% (original amino acid) | L | Q | L | E | H | LL | L | D | LQ | M | |
| | | 50% (mutant amino acid) | V,I,D,N,E,Q, R,K,F,Y,W | D,E,V, L,F,N,T | | D,N,Q,H, W,K,R,Y | D,N,Q,H, W,Y,F,T,I, R,K | | V,I,M,T,D, N,E,Q,Y,H, R,K | E,N,Q, T,V,L | | V,I,D,N,E,Q, F,Y,W,R,K | |

According to the table, the original amino acids in N1-N7 are 50%, and the remaining 50% are equally divided by the corresponding mutant amino acids. The codon is preferably saccharomyces cerevisiae

| Primer | | N1 | N2 | N3 | N4 | N5 | N6 | N7 | N8 | N9 | |
|---|---|---|---|---|---|---|---|---|---|---|---|
| | 5' | CAT | TTA | CCT | CGT | GAT | AGC | AAC | GTG | ATC | GTGCTG GAGCTG AAGGGC AG 3' |
| | | | | | | | | ATC AAC | | | |
| | | | | | | | | | | | |
| AMP02 23 | | CAATTAGC CCAGAGCAA GAACTTC | | | | | | | | | |
| | | 50% (original amino acid) | H | L | P | R | D | S | N | V | I |
| | | 50% (mutant amino acid) | R,K,Y,W, D,E,Q | | I,T,A | E | E,N,Q, H,T,V | T,D,N,E, Q,K,R, Y,W | D,E, Q,H, Y,W | T,L,I,M,D, N,E,Q,H | V,L,M,F, Y,W,N,D, E,Q |
| | | | | | | | | | LI | IN | |

According to the table, the original amino acids in N1-N9 are 50%, and the remaining 50% are equally divided by the corresponding mutant amino acids. The codon is preferably saccharomyces cerevisiae

FIG. 3B

| Clone No. | 35 | 37 | 38 | 41 | 42 | 43 | 45 | 61 | 62 | 68 | 72 |
|---|---|---|---|---|---|---|---|---|---|---|---|
| IL-2^WF | K | T | R | T | F | K | Y | E | E | E | L |
| Y27A3 | D | K | E | K | Q | D | Y | E | E | E | L |
| Y28E4 | D | D | R | F | F | D | K | E | E | Y | L |
| Y29A1 | D | D | D | F | F | E | K | E | E | E | L |
| Y29A2 | D | K | D | E | F | E | Y | E | E | E | L |
| Y29A3 | D | T | F | T | E | E | K | E | E | E | L |
| Y29A4 | E | T | F | T | E | E | Y | E | E | E | L |
| Y29A5 | D | E | D | E | E | E | Y | E | E | E | F |
| Y29A6 | E | T | D | T | E | E | Y | K | E | E | L |
| Y29B2 | E | D | W | M | Q | E | K | K | E | R | K |
| Y29B3 | K | D | R | E | F | E | K | E | E | K | L |
| Y29B4 | E | T | E | M | E | E | K | E | E | E | L |
| Y29B5 | D | T | D | E | E | E | Y | E | E | E | F |
| Y29C2 | E | D | D | T | F | E | Y | E | E | E | L |
| Y29C5 | E | D | D | E | F | E | K | E | E | E | F |
| Y29D1 | E | E | E | E | F | E | Y | W | E | E | F |
| Y29D2 | D | E | E | E | F | E | K | E | E | E | F |
| Y29D5 | D | T | D | T | A | E | Y | E | E | E | L |
| Y29D6 | D | D | W | E | Q | K | K | E | E | Y | L |
| Y29E3 | E | E | D | E | F | D | Y | E | E | E | L |
| Y29E4 | E | T | R | R | R | D | R | E | E | R | F |
| Y29F2 | E | E | W | Q | E | D | Y | E | E | E | L |
| Y29F3 | E | T | D | Y | E | D | R | L | E | E | K |
| Y29F4 | D | Y | W | T | F | E | Y | E | E | E | F |
| Y29G4 | E | E | D | F | F | K | K | E | E | L | L |
| Y29G5 | D | E | E | K | F | Y | R | E | E | E | L |
| Y29H4 | K | K | R | K | F | K | K | E | E | K | K |
| Y29H5 | E | T | W | T | Q | K | R | W | E | R | L |
| Y30A1 | D | E | E | E | F | K | Y | E | E | E | F |
| Y30A3 | D | E | D | E | F | K | Y | E | E | E | F |
| Y30A4 | D | E | D | E | F | E | Y | E | E | E | F |
| Y30A5 | E | T | E | E | F | Y | K | E | E | E | L |
| Y30A6 | D | D | R | T | A | Y | Y | E | E | E | L |
| Y30B1 | E | T | E | E | F | Y | K | E | E | Y | L |
| Y30B4 | D | T | W | T | Y | Y | K | R | E | W | L |
| Y30B6 | K | T | K | R | Q | K | K | Y | E | R | L |
| Y30C1 | E | E | T | T | Q | K | K | L | E | E | L |
| Y30C2 | D | D | E | E | F | E | Y | E | E | E | L |
| Y30C4 | E | D | E | T | F | E | Y | E | E | E | L |
| Y30D1 | E | T | T | T | F | E | Y | E | E | E | F |
| Y30D2 | E | E | E | E | F | K | Y | E | E | E | F |
| Y30D4 | E | D | E | T | A | E | Y | E | E | E | L |
| Y30E1 | E | T | F | E | E | E | K | E | E | E | L |
| Y30E3 | E | K | E | E | E | K | Y | K | E | Y | L |
| Y30E6 | K | T | K | Q | P | E | K | E | E | E | E |
| Y30F1 | D | T | D | T | F | R | Y | E | E | R | L |
| Y30F4 | D | E | E | E | R | K | Y | E | E | E | F |
| Y30F6 | E | E | F | E | E | E | Y | E | E | E | L |
| Y30G1 | E | D | D | T | F | E | Y | E | E | E | L |
| Y30G3 | E | T | F | E | F | Y | K | E | E | K | L |
| Y30G4 | D | E | W | E | E | Y | R | E | E | E | L |
| Y30H1 | E | D | E | T | E | Y | Y | E | E | E | L |
| Y30H3 | E | T | E | E | F | K | K | E | E | E | L |
| Y30H4 | E | D | W | T | E | K | K | E | E | Y | R |

FIG. 4A

| Clone No. | 35 | 37 | 38 | 41 | 42 | 43 | 45 | 61 | 62 | 68 | 72 |
|---|---|---|---|---|---|---|---|---|---|---|---|
| IL-2^WT | K | T | R | T | F | K | Y | E | E | E | L |
| Y33A1 | E | D | W | T | Q | K | R | E | R | R | L |
| Y33A2 | E | D | R | F | A | E | Y | W | E | K | W |
| Y33A3 | K | T | R | K | F | D | R | L | E | K | K |
| Y33A4 | E | E | W | T | Q | K | R | R | E | R | L |
| Y33A5 | E | D | W | T | Q | K | R | K | E | R | L |
| Y33A6 | E | D | W | T | Q | K | K | W | E | R | L |
| Y33B1 | E | T | W | T | Q | K | K | K | E | R | L |
| Y33B4 | E | T | W | T | Q | K | K | W | E | R | L |
| Y33B5 | E | D | W | T | Q | K | K | R | E | R | L |
| Y33C4 | E | T | D | T | F | K | K | E | E | R | K |
| Y33C5 | E | T | W | T | Q | K | R | R | E | R | L |
| Y33E5 | K | E | R | T | F | D | Y | E | E | Y | R |
| Y33F3 | E | T | R | T | F | K | R | L | E | W | L |
| Y33F4 | E | D | W | T | Q | K | R | R | E | R | L |
| Y33G4 | E | D | V | T | E | W | R | L | E | W | L |
| Y34B3 | E | W | E | Y | R | D | K | K | E | W | L |
| Y34C2 | D | T | W | T | K | Y | R | R | E | W | K |
| Y34C3 | E | E | R | T | F | K | Y | W | E | E | K |
| Y34E2 | E | T | Y | E | F | K | Y | E | E | Y | L |
| Y34F4 | E | E | W | T | Q | K | R | K | E | R | L |
| Y34G3 | K | D | R | T | F | D | R | Y | E | K | R |
| Y34H1 | D | T | W | T | E | Y | R | R | E | Y | K |
| Y34H2 | K | E | R | T | R | K | R | Y | E | K | K |
| Y34H4 | E | D | V | T | A | K | K | R | W | Y | R |

FIG. 4B

| Clone No. | 79 | 81 | 82 | 83 | 84 | 87 | 88 | 91 | 92 |
|---|---|---|---|---|---|---|---|---|---|
| IL-2^WT | H | R | P | R | D | S | N | V | I |
| Y27C1 | E | D | I | E | D | D | N | V | I |
| Y27C2 | H | D | A | E | D | E | N | V | M |
| Y27C5 | H | D | A | E | D | E | N | V | L |
| Y27D2 | E | D | T | E | D | E | N | L | I |
| Y27D4 | H | D | T | E | D | D | N | V | L |
| Y27E1 | Q | D | A | E | D | E | N | V | I |
| Y27F6 | H | D | T | E | D | E | N | V | M |
| Y28A2 | D | D | P | R | D | D | N | V | L |
| Y28A5 | E | N | A | E | D | D | N | V | L |
| Y28F1 | H | D | T | E | D | D | N | L | L |
| Y28F5 | E | D | A | E | D | E | N | V | M |
| Y32D5 | D | D | P | E | D | E | N | I | L |
| Y35A5 | H | N | T | E | D | E | N | L | F |
| Y35B6 | D | N | T | E | D | E | N | L | F |
| Y35C2 | Q | D | T | E | D | D | N | L | Y |
| Y35D2 | H | D | T | E | D | D | N | V | M |
| Y35E1 | H | D | I | E | D | D | N | I | Y |
| Y35E6 | E | D | I | E | D | E | N | V | M |
| Y35G4 | H | D | P | E | D | D | N | V | L |
| Y35H1 | E | D | T | R | D | E | N | V | F |
| Y36B2 | H | D | T | E | D | E | N | L | I |
| Y36D6 | H | D | A | E | D | E | N | L | I |
| Y36E3 | H | D | T | E | D | E | N | V | I |
| Y36E5 | H | D | P | E | D | E | N | V | L |
| Y36G2 | D | D | P | E | D | D | N | V | I |

FIG. 4C

| Clone No. | 35 | 37 | 38 | 41 | 42 | 43 | 45 | 61 | 62 | 68 | 72 | 79 | 81 | 82 | 83 | 84 | 87 | 88 | 91 | 92 |
|---|---|---|---|---|---|---|---|---|---|---|---|---|---|---|---|---|---|---|---|---|
| IL-2^WT | K | T | R | T | F | K | Y | E | E | E | L | H | R | P | R | D | S | N | V | I |
| Y01 | D | E | E | E | F | E | K | E | E | E | F | E | D | I | E | D | D | N | V | I |
| Y02 | E | T | D | E | F | E | Y | E | E | E | F | H | D | A | E | D | E | N | V | M |
| Y03 | E | T | W | T | Q | K | K | L | E | R | L | H | D | A | E | D | E | N | V | L |
| Y04 | D | K | E | K | Q | D | Y | E | E | Y | L | E | D | T | E | D | E | N | L | I |
| Y05 | D | E | D | T | F | Y | K | E | E | E | F | H | D | T | E | D | D | N | V | L |
| Y06 | E | Y | W | Y | E | E | K | E | E | E | K | Q | D | A | E | D | E | N | V | I |
| Y07 | D | T | W | T | E | E | K | E | E | K | L | H | D | T | E | D | E | N | V | M |
| Y08 | E | T | R | Q | R | D | Y | E | E | Y | L | D | D | P | R | D | D | N | V | L |
| Y09 | D | T | W | T | E | Y | R | R | E | Y | L | E | N | A | E | D | D | N | V | L |
| Y10 | D | T | F | E | E | K | K | E | E | Y | L | H | D | T | E | D | D | N | L | L |
| Y11 | E | K | E | E | F | E | Y | E | E | E | F | E | D | A | E | D | E | N | V | M |
| Y12 | K | T | K | R | Q | K | K | Y | E | W | L | D | D | P | E | D | E | N | I | L |

FIG. 4D

| Position No. | 1-34 | 35 | 36 | 37 | 38 | 39-40 | 41 |
|---|---|---|---|---|---|---|---|
| IL-2^WT | APTSSSTKKTQLQLEHLLLDLQMILNGINNYKNP | K | L | T | R | ML | T |
| IL-2^3X | APTSSSTKKTQLQLEHLLLDLQMILNGINNYKNP | K | L | T | D | ML | T |
| IL-2^H9 | APTSSSTKKTQLQLEHLLLDLQMILNGINNYKNP | K | L | T | R | ML | T |

| Position No. | 42 | 43 | 44 | 45 | 46-60 | 61 | 62 | 63-67 | 68 | 69-71 |
|---|---|---|---|---|---|---|---|---|---|---|
| IL-2^WT | F | K | F | Y | MPKKATELKHLQCLE | E | E | LKPLE | E | VLN |
| IL-2^3X | F | E | F | Y | MPKKATELKHLQCLE | R | E | LKPLE | E | VLN |
| IL-2^H9 | F | K | F | Y | MPKKATELKHLQCLE | E | E | LKPLE | E | VLN |

| Position No. | 72 | 73-78 | 79 | 80 | 81 | 82 | 83 | 84 | 85-86 | 87 | 88 | 89-90 | 91 |
|---|---|---|---|---|---|---|---|---|---|---|---|---|---|
| IL-2^WT | L | AQSKNF | H | L | R | P | R | D | LI | S | N | IN | V |
| IL-2^3X | L | AQSKNF | H | L | R | P | R | D | LI | S | N | IN | V |
| IL-2^H9 | L | AQSKNF | H | F | D | P | R | D | VV | S | N | IN | V |

| Position No. | 92 | 93-133 |
|---|---|---|
| IL-2^WT | I | VLELKGSETTFMCEYADETATIVEFLNRWITFSQSIISTLT |
| IL-2^3X | I | VLELKGSETTFMCEYADETATIVEFLNRWITFSQSIISTLT |
| IL-2^H9 | F | VLELKGSETTFMCEYADETATIVEFLNRWITFSQSIISTLT |

FIG. 6

INTERLEUKIN-2 AND USE THEREOF

TECHNICAL FIELD

The present invention relates to a novel interleukin-2 (IL-2) mutant protein and use thereof. In particular, the present invention relates to an IL-2 mutant protein with reduced binding ability for an IL-2Rα receptor and/or enhanced binding ability for an IL-2Rβ receptor compared with a wild-type IL-2 protein. The present invention further provides a fusion protein and an immunoconjugate comprising the IL-2 mutant protein, a nucleic acid encoding the IL-2 mutant protein, and a vector and a host cell comprising the nucleic acid. The present invention further provides a method for preparing the IL-2 mutant protein, a pharmaceutical composition comprising the IL-2 mutant protein, and therapeutic use of the mutant protein.

BACKGROUND

Interleukin-2 (IL-2), also known as T-cell growth factor (TCGF), is a pluripotent cytokine produced mainly by activated T cells, in particular, by CD4+ T helper cells. In eukaryotic cells, human IL-2 (uniprot: P60568) is synthesized as a precursor polypeptide of 153 amino acids, and mature secretory IL-2 is produced after removal of 20 N-terminus amino acids. The sequences of IL-2 from other species have also been disclosed. See NCBI Ref Seq No. NP032392 (mice), NP446288 (rats) or NP517425 (chimpanzees).

Interleukin-2 has 4 antiparallel and amphipathic a helices, which form a quaternary structure essential for its function (Smith, *Science* 240, 1169-76 (1988); Bazan, *Science* 257, 410-413 (1992)). In most cases, IL-2 acts through three different receptors: IL-2Rα (CD25), IL-2Rβ (CD122), and IL-2Rγ (CD132). IL-2Rβ and IL-2Rγ are critical for IL-2 signaling, while IL-2Rα (CD25) is not essential for signaling but can enable IL-2 to bind to a receptor with high affinity (Krieg et al., *Proc Natl Acad Sci* 107, 11906-11 (2010)). The trimeric receptor (IL-2Rαβγ) formed by the combination of IL-2Rα, IL-2Rβ, and IL-2Rγ is an IL-2 high affinity receptor (with $K_D$ of about 10 pM), the dimeric receptor (IL-2Rβγ) consisting of IL-2Rβ and IL-2Rγ is an intermediate affinity receptor (with $K_D$ of about 1 nM), and the IL-2 receptor formed solely by subunit α is a low affinity receptor.

Immune cells express dimeric or trimeric IL-2 receptors. The dimeric receptor is expressed on cytotoxic CD8+ T cells and natural killer cells (NK), whereas the trimeric receptor is expressed predominantly on activated lymphocytes and CD4+ CD25+ FoxP3+ suppressive regulatory T cells (Treg) (Byman, O. and Sprent. J. *Nat. Rev. Immunol.* 12, 180-190 (2012)). Effector T cells and NK cells in a resting state are relatively insensitive to IL-2 because they do not have CD25 on the cell surface. However, Treg cells consistently express the highest level of CD25 in vivo, and therefore normally IL-2 would preferentially stimulate Treg cell proliferation.

IL-2 mediates multiple actions in an immune response by binding to IL-2 receptors on different cells. In one aspect, as an immune system stimulator, IL-2 can stimulate T cell proliferation and differentiation, induce cytotoxic T lymphocyte (CTL) production, promote B cell proliferation and differentiation and immunoglobulin synthesis, and stimulate the production, proliferation and activation of natural killer (NK) cells, and thus has been approved as an immunotherapeutic agent for the treatment of cancer and chronic viral infection. In another aspect, IL-2 can promote the activation and proliferation of immunosuppressive CD4+ CD25+ regulatory T cells (i.e., Treg cells) (Fontenot et al., *Nature Immunol.* 6, 1142-51 (2005); D'Cruz and Klein, *Nature Immunol.* 6, 1152-59 (2005); Maloy and Powrie, *Nature Immunol.* 6, 1171-72 (2005)), thus resulting in immunosuppression. In addition, high-dose IL-2 administration may cause vascular leak syndrome (VLS) in patients. IL-2 has been shown to induce pulmonary edema by direct binding to IL-2 trimeric receptors (IL-2Rαβγ) on lung endothelial cells (Krieg et al., *Proc Nat Acad Sci USA* 107, 11906-11 (2010)).

To solve the above problems associated with IL-2 immunotherapy, it has been proposed to alter the selectivity or preference of IL-2 for different receptors to reduce the toxicity of IL-2 therapy and/or improve its effect. For example, it has been proposed that a complex of IL-2 and IL-2 monoclonal antibody, by targeting IL-2 to cells expressing CD122 but not CD25, induces preferential amplification of $CD122^{high}$ populations, and improves the effect of IL-2 therapy in vivo (Boyman et al., *Science* 311, 1924-1927 (2006)). Oliver AST et al. (US2018/0142037) proposed to introduce triple mutations F42A/Y45A/L72G at amino acid residue positions 42, 45, and 72 of IL-2 so as to reduce the affinity for the IL-2Rα receptor. Aron M. Levin et al. (*Nature*, Vol 484, p 529-533, DOI: 10.1038/nature10975) proposed an IL-2 mutant IL-$2^{H9}$ called "superkine", which comprises quintuple mutations L80F/R81D/L85V/I86V/I92F, and has enhanced binding to IL-2Rβ, thereby boosting the stimulation of CD25- cells. Rodrigo Vazquez-Lombardi et al. (*Nature Communications*, 8:15373, DOI: 10.1038/ncomms15373) proposed a triple mutant human IL-2 mutant protein IL-$2^{3X}$, which has residue mutations R38D/K43E/E61R at amino acid residue positions 38, 43 and 61, respectively, resulting in the mutant protein not binding to IL-2Rα, so as to eliminate the activation preference of IL-2 for CD25+ cells. However, the activation preference of IL-$2^{3X}$ for CD25+ cells still exists, and the expression level of the mutant protein is low, which is not conducive to subsequent large-scale drug production.

In view of the role of IL-2 in immune regulations and diseases, there is still a need in the art to develop novel IL-2 molecules with improved properties.

SUMMARY

The present invention satisfied the above need by providing a novel IL-2 mutant protein with improved IL-2 receptor selectivity/preference relative to the wild-type IL-2 protein.

Thus, in one aspect, the present invention provides a novel IL-2 mutant protein. In some embodiments, the IL-2 mutant protein disclosed herein has one or more of the following properties:

(i) reduced binding affinity for IL-2Rα receptor compared with the wild-type IL-2 protein;
(ii) enhanced binding affinity for IL-2Rβ receptor compared with the wild-type IL-2 protein;
(iii) an ability to effectively reduce the activation preference of IL-2 for CD25+ cells; and
(iv) an ability to effectively activate CD25- cells.

In some embodiments, the IL-2 mutant protein disclosed herein has high expression level compared with the wild-type IL-2 protein.

In some embodiments, the present invention provides an IL-2 mutant protein comprising at least one mutation at amino acid residue positions 35-72 of IL-2; in other embodiments, the present invention provides an IL-2 mutant protein comprising at least one mutation at amino acid residue positions 79-92 of IL-2; and in still other embodiments, the present invention provides an IL-2 mutant protein comprising more than two and preferably more than three mutations at amino acid positions 35-72 and 79-92.

In addition, the present invention provides a fusion protein and an immunoconjugate comprising the IL-2 mutant protein, a pharmaceutical composition, and a combination product; a nucleic acid encoding the IL-2 mutant protein, and a vector and a host cell comprising the nucleic acid; and a method for producing the IL-2 mutant protein, the fusion protein and the immunoconjugate disclosed herein.

Furthermore, the present invention also provides a method for treating diseases and a method and use for stimulating the immune system of a subject using the IL-2 mutant protein disclosed herein.

The present invention is further illustrated in the following drawings and specific embodiments. However, these drawings and specific embodiments should not be construed as limiting the scope of the present invention, and modifications easily conceived by those skilled in the art will be included in the spirit of the present invention and the protection scope of the appended claims.

BRIEF DESCRIPTION OF THE DRAWINGS

FIGS. 3A-B show a primer design used to construct mutant library IBYDL029 and mutant libraries IBYDL030 and IBYDL031.

FIGS. 4A-D show some IL-2 mutant proteins and sequences thereof screened from mutant libraries IBYDL029 and IBYDL031, as well as some new mutant proteins and sequences thereof produced by combination of mutations screened from the two libraries.

FIG. 6 shows the mature protein sequence (SEQ ID NO: 1) of human interleukin (IL-2) and the numbering of amino acid residues thereof, and shows the sequence alignments with mutant proteins IL-2$^{3X}$ and IL-2$^{H9}$.

DETAILED DESCRIPTION

Figure 1:
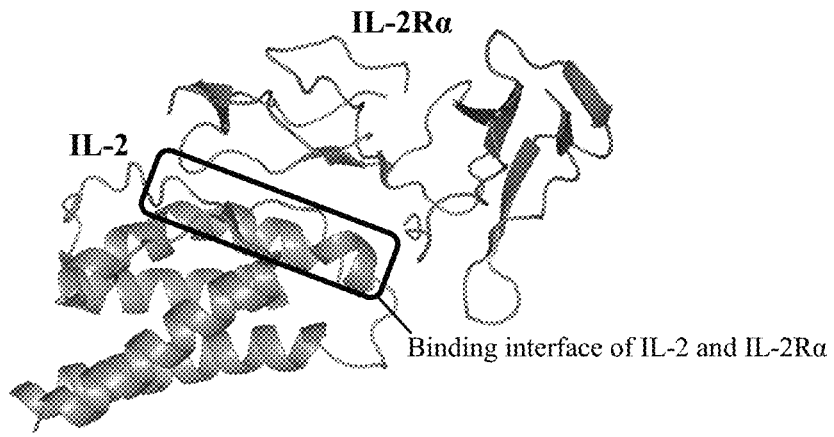
FIG. 1 shows the crystal structure of a complex of IL-2 and IL-2Rα.

Unless otherwise defined, all technical and scientific terms used herein have the same meaning as those commonly understood by those of ordinary skill in the art. For the purposes of the present invention, the following terms are defined below.

The term "about" used in combination with a numerical value is intended to encompass the numerical values in a range from a lower limit less than the specified numerical value by 5% to an upper limit greater than the specified numerical value by 5%.

The term "and/or" should be understood to refer to any one of the options or any two or more of the options.

As used herein, the term "comprise" or "include" is intended to mean that the elements, integers or steps are included, but not to the exclusion of any other elements, integers or steps. As used herein, the term "comprise" or "include", unless indicated otherwise, also encompasses the situation where the entirety consists of the described elements, integers or steps. For example, when referring to an IL-2 mutant protein "comprising" or "including" a mutation or a combinatorial mutation, it is also intended to encompass IL-2 mutant proteins having only said mutation or combinatorial mutation. As used herein, wild-type "interleukin-2" or "IL-2" refers to a parent IL-2 protein, preferably a naturally occurring IL-2 protein, e.g., a native IL-2 protein derived from a human, mouse, rat, or non-human primate, serving as a template to which a mutation or a combinatorial mutation disclosed herein is introduced, including both unprocessed (e.g., without the removal of the signal peptide) and processed (e.g., with the removal of the signal peptide) forms. In addition, this term includes naturally occurring allelic and splice variants, isotypes, homologs, and species homologs of IL-2. This term also includes variants of native IL-2, which may, for example, have at least 95%-99% or more identity to the native IL-2 or have no more than 1-10 or 1-5 amino acid mutations (especially conservative amino acid substitutions) and have substantially the same binding affinity for IL-2Rα and/or IL-2Rβ as the native IL-2 protein. Therefore, in some embodiments, compared to the native IL-2 protein, the wild-type IL-2 protein may comprise amino acid mutations that do not affect its binding to the IL-2 receptor. For example, a native human IL-2 protein (uniprot: P60568) with a mutation C125S introduced at position 125 is a wild-type IL-2 protein disclosed herein. An example of the wild-type human IL-2 protein is set forth in SEQ ID NO: 1. In some embodiments, the wild-type human IL-2 sequence may have at least 85%, 90%, 95%, or even at least 96%, 97%, 98%, 99% or higher amino acid sequence identity to the amino acid sequence set forth in SEQ ID NO: 1.

As used herein, the amino acid mutation may be an amino acid substitution, deletion, insertion, and addition. Any combination of substitution, deletion, insertion and addition may be made to obtain a final mutant protein construct with the desired properties, such as reduced binding affinity for IL-2Rα. Amino acid deletions and insertions include amino- and/or carboxyl-terminus deletions and insertions of a polypeptide sequence. For example, an alanine residue can be deleted at position 1 of a full-length human IL-2. Preferred amino acid mutations are amino acid substitutions. In some embodiments, when an IL-2 mutant protein with altered receptor binding properties is intended to be produced by introducing mutations at specific mutant amino acid positions described herein, it is preferred to perform non-conservative amino acid substitutions at the positions. In some embodiments, preferred non-conservative amino acid substitutions include replacement of hydrophobic amino acids with hydrophilic amino acids, or replacement with amino acids having different polarities or opposite charges.

In the present invention, when mentioning an amino acid position, it is determined by referring to the amino acid sequence of the wild-type human IL-2 protein (also referred to as IL-2$^{WT}$) set forth in SEQ ID NO: 1 (as shown in FIG. 6). The corresponding amino acid positions on other IL-2 proteins or polypeptides (including full-length sequences or truncated fragments) can be identified by performing an amino acid sequence alignment (e.g., using Basic Local Alignment Search Tool (BLAST) available from http://blast.ncbi.nlm.nih.gov/Blast.cgi?PROGRAM=blastp&PAGE_TYPE=BlastSearch&LINK_LOC=blasthome, with default parameters). Therefore, in the present invention, for example, when mentioning "F42", it refers to a phenylalanine residue F at position 42 of SEQ ID NO: 1, or an amino acid residue at other corresponding positions of the IL-2 sequence by alignment. When mentioning a combination of multiple positions, such as a combination of F42, R81, and S87, it can be indicated as F42/R81/S87.

As used herein, when referring to the IL-2 mutant protein, mutations are described in the following manners. An amino acid substitution is expressed as original amino acid residue/position/amino acid residue for substitution. For example, the substitution of isoleucine at position 92 with leucine can be indicated as I92L. When there are multiple optional amino acid substitutions (e.g., D, E, Q) at a given position (e.g., H79), the substitutions can be indicated as: (1) H79D, E, Q; or (2) H79D/E/Q. Correspondingly, for a combinatorial mutation at multiple given positions (e.g., R81, R83 and S87), it can be indicated as: (1) R81D/N, R83E, I92L/F/Y; or (2) R81D/S87D/I92L.

As used herein, the "percent sequence identity" can be determined by comparing two optimally aligned sequences over a comparison window. Preferably, the sequence identity is determined over the full length of a reference sequence (e.g., SEQ ID NO: 1). Methods of sequence alignment for comparison are well known in the art. Algorithms suitable for determining the percent sequence identity include, for example, BLAST and BLAST 2.0 algorithms (see Altschul et al., *Nuc. Acids Res.* 25: 3389-402, 1977 and Altschul et al., *J. mol. Biol.* 215: 403-10, 1990). Software for performing BLAST analysis is publicly available (http://www.ncbi.nlm.nih.gov/) from the National Center for Biotechnology Information. For purposes of this application, the percent identity is typically determined using the BLAST 2.0 algorithm, with parameters set to default values.

As used herein, the term "conservative substitution" means an amino acid substitution that does not adversely affect or alter the biological function of a protein/polypeptide comprising an amino acid sequence. For example, a conservative substitution may be introduced by standard techniques known in the art, such as site-directed mutagenesis and PCR-mediated mutagenesis. A typical conservative amino acid substitution involves a substitution of an amino acid by another amino acid having similar chemical properties (e.g., charge or hydrophobicity). The following six groups comprise amino acids that can be typically conservatively substituted by each other: 1) alanine (A), serine (S), and threonine (T); 2) aspartic acid (D) and glutamic acid (E); 3) asparagine (N) and glutamine (Q); 4) arginine (R) and lysine (K); 5) isoleucine (I), leucine (L), methionine (M), and valine (V); and 6) phenylalanine (F), tyrosine (Y), and tryptophan (W). For example, relative to SEQ ID NO: 1, the wild-type IL-2 protein may have conservative amino acid substitutions, or only have conservative amino acid substitutions. For another example, relative to the wild-type IL-2 protein, the IL-2 mutant protein disclosed herein may have a conservative amino acid substitution in addition to characteristic mutations described herein, or only have a conservative amino acid substitution.

"Affinity" or "binding affinity" refers to the inherent binding ability that reflects the interaction between members of a binding pair. The affinity of molecule X for its binding partner Y can be represented by an equilibrium dissociation constant ($K_D$), which is the ratio of a dissociation rate constant ($k_{dis}$) to an association rate constant ($k_{on}$). Binding affinity can be measured by common methods known in the art. One specific method for measuring affinity is the biolayer interferometry (BLI) technology described herein. In addition, changes in the affinity of the IL-2 mutant protein for different receptors can also be preliminarily evaluated by the flow cytometry described herein. For example, the wild-type IL-2 protein and the IL-2 mutant protein displayed on yeast cells can be stained with biotinylated IL-2Rβ or IL-2Rα receptors to identify the IL-2 mutant protein with altered binding affinity for the IL-2R receptors IL-2Rβ or IL-2Rα compared with the wild-type IL-2 protein.

As used herein, an antibody-binding molecule is a polypeptide molecule that can specifically bind to an antigen, e.g., an immunoglobulin molecule, an antibody, or an antibody fragment (e.g., a Fab fragment and a scFv fragment).

As used herein, an antibody Fc fragment refers to a C-terminus region of an immunoglobulin heavy chain that contains at least a portion of the constant region, and may include Fc fragments of native sequences and variant Fc fragments. In one embodiment, a human IgG heavy chain Fc fragment extends from Cys226 or from Pro230 of a heavy chain to a carboxyl terminus. In another embodiment, the C-terminus lysine (Lys447) of the Fc fragment may or may not be present. In other embodiments, the Fc fragment may comprise a mutation, for example, a L234A/L235A mutation. Unless otherwise indicated herein, amino acid residues in the Fc fragment are numbered according to the EU numbering system, also called the EU index, as described in Kabat, E. A. et al., *Sequences of Proteins of Immunological Interest*, 5th edition, Public Health Service, National Institutes of Health, Bethesda, Md. (1991), NIH Publication 91-3242.

All aspects of the present invention are further detailed in the following sections.

1. IL-2 Mutant Protein Disclosed Herein

In one aspect, the present invention provides a novel IL-2 mutant protein with improved IL-2 receptor selectivity/preference, more specifically, reduced or eliminated binding affinity for an IL-2Rα receptor and/or enhanced binding affinity for an IL-2Rβ receptor.

Advantageous Biological Properties of the IL-2 Mutant Protein Disclosed Herein

The IL-2 protein triggers signaling and functions by interacting with IL-2 receptors. Wild-type IL-2 exhibits different affinities for different IL-2 receptors. IL-2Rβ and IL-2Rγ receptors having a low affinity for wild-type IL-2 are expressed on resting effector cells, including $CD8^+$ cytotoxic T cells and NK cells. IL-2Rα receptors with a high affinity for wild-type IL-2 are expressed on regulatory T cell (Treg) cells and activated effector cells. Due to high affinity, the wild-type IL-2 will preferentially bind to IL-2Rα on the cell surface and then recruit IL-2Rβγ. Treg cells and activated effector cells are stimulated by downstream p-STAT5 signals released through the IL-2Rβγ. Thus, without being bound by theory, decreasing or eliminating the affinity of IL-2 for the IL-2Rα receptor will reduce the preference of IL-2 for preferentially activating $CD25^+$ cells and the IL-2 mediated immune downregulation of Treg cells. Without being bound by theory, maintaining or enhancing the affinity for the IL-2Rβ receptor will retain or enhance the activation of IL-2 on effector cells such as $CD8^+$ cytotoxic T cells and NK cells, thus achieving immunostimulation.

By introducing one or more mutations, especially more than three mutations to a region of the IL-2 mutant protein disclosed herein where IL-2 interacts with IL-2Rα (amino acid residue positions 35-72) and/or a region where IL-2 interacts with IL-2Rβ (amino acid residue positions 79-92), the binding of the IL-2 mutant protein to IL-2Rα is reduced or absent, and/or the binding to IL-2Rβ is unchanged or enhanced. Thus, the IL-2 mutant protein disclosed herein has improved properties relative to the wild-type IL-2 protein, including, for example, one or more of the following:

(1) reduced or eliminated binding affinity for IL-2Rα receptor;

(2) enhanced binding affinity for IL-2Rβ receptor;

(3) reduced binding affinity for high-affinity IL-2R receptor (IL-2Rαβγ);
(4) increased binding affinity for intermediate-affinity IL-2R receptor (IL-2Rβγ);
(5) a reduced ability to activate IL-2 signaling, particularly STAT5 phosphorylation signals, in CD25$^+$ cells (particularly activated CD8$^+$ T cells and Treg cells);
(6) resulting in a decrease in IL-2 mediated activation and proliferation of CD25$^+$ cells (particularly activated CD8$^+$ T cells and Treg cells);
(7) reducing or eliminating preference of the IL-2 for preferentially stimulating Treg cell proliferation;
(8) reducing the IL-2 mediated immune downregulation effect of Treg cells;
(9) maintaining or enhancing, especially enhancing, the activation of CD25$^-$ cells, particularly CD25$^-$ T effector cells and NK cells;
(10) resulting in an increase in IL-2 mediated activation and proliferation of effector T cells and NK cells;
(11) resulting in increased immunostimulation; and
(12) increasing anti-tumor effect.

In some embodiments, the IL-2 mutant protein disclosed herein has the property of (1) above, preferably further has one or more, especially all, properties selected from (3) and (5)-(8), and more preferably still further has one or more, especially all, properties selected from (2) and (9)-(12). In some embodiments, the IL-2 mutant protein disclosed herein has the property of (2) above, preferably further has one or more, especially all, properties selected from (9)-(12), and more preferably still further has one or more, especially all, properties selected from (1), (3), and (5)-(8).

In some preferred embodiments, the IL-2 mutant protein disclosed herein also has reduced in vivo toxicity mediated by the binding of IL-2 to the high-affinity receptor IL-2Rαβγ relative to the wild-type IL-2 protein.

In some embodiments, the IL-2 mutant protein disclosed herein has improved druggability. For example, when expressed in mammalian cells such as H293T cells, it has one or more properties selected from: (i) superior expression level to the wild-type IL-2 protein; (ii) superior homogeneity to the wild-type IL-2 protein; and (iii) easy purification to a higher protein purity.

In some embodiments disclosed herein, the IL-2 mutant protein disclosed herein shows an increased expression level relative to the wild-type IL-2. In some embodiments disclosed herein, the increased expression occurs in a mammalian cell expression system. The expression level can be determined by any suitable method that allows for quantitative or semi-quantitative analysis of the amount of recombinant IL-2 protein in cell culture supernatant, preferably the supernatant purified by one-step affinity chromatography. In some embodiments, compared with the wild-type IL-2 protein, the expression level of the IL-2 mutant protein disclosed herein in mammalian cells is increased by more than at least 1.1-fold, 1.5-fold, 2-fold, 2.5-fold, 3-fold, 3.5-fold or 4-fold.

In some preferred embodiments, the IL-2 mutant protein disclosed herein can reach a purity of higher than 70%, 80%, or 90% after being purified by one-step protein A affinity chromatography. In some embodiments, the purity of the protein is detected by a SEC-HPLC technique.

In some embodiments, compared with the wild-type IL-2 protein (e.g., IL-2$^{WT}$ set forth in SEQ ID NO: 1), the affinity for the IL-2Rα receptor of the IL-2 mutant protein disclosed herein is reduced by more than at least 5-fold, at least 10-fold, or at least 25-fold, especially at least 30-fold, 50-fold or 100-fold. In a preferred embodiment, the mutant protein disclosed herein does not bind to IL-2Rα receptor. The binding affinity can be determined by measuring the equilibrium dissociation constant ($K_D$) of the binding of the IL-2 mutant protein disclosed herein, such as the IL-2 mutant protein disclosed herein fused to an Fc fragment, to the IL-2Rα receptor using the bio-layer interferometry (BLI) technology.

In some embodiments, compared with the wild-type IL-2 protein, the affinity for the IL-2Rβ receptor of the IL-2 mutant protein disclosed herein (e.g., IL-2$^{WT}$ set forth in SEQ ID NO: 1) is enhanced by more than at least 5-fold, at least 10-fold, or at least 25-fold, especially at least 30-fold, 50-fold or 100-fold, preferably, at least 150-fold, 200-fold, 250-fold, 300-fold, 350-fold, 400-fold, 450-fold, 500-fold or 550-fold. The binding affinity can be determined by measuring the equilibrium dissociation constant ($K_D$) of the binding of the IL-2 mutant protein disclosed herein, such as the IL-2 mutant protein disclosed herein fused to an Fc fragment, to the IL-2Rβ receptor using the bio-layer interferometry (BLI) technology. In one embodiment, in a BLI assay, the $K_D$ of the binding affinity of IL-2 mutant protein disclosed herein (in the form of an IL-2-Fc fusion protein) to the IL-2Rβ receptor is less than 10.0E-09M, such as less than 6.0E-09M, 3.0E-09M, 2.0E-09M, 1.0E-09M, preferably less than 9.0E-10M, such as less than 6.0E-10M, 5.0E-10M, 4.0E-10M, 3.0E-10M, 2.0E-10M, 1.0E-10M, more preferably less than 9.0E-11M, 8.0E-11M, or 7.0E-11M.

In one embodiment, the IL-2 mutant protein disclosed herein reduces IL-2-mediated activation and proliferation of CD25$^+$ cells relative to the wild-type IL-2. In one embodiment, the CD25$^+$ cells are CD25$^+$ CD8$^+$ T cells. In another embodiment, the CD25$^+$ cells are Treg cells. In one embodiment, in the STAT5 phosphorylation assay, the ability of the IL-2 mutant protein to activate CD25$^+$ cells is identified by measuring the activation of STAT5 phosphorylation signals by the IL-2 mutant protein in CD25$^+$ cells. For example, as described in the examples of the present invention, STAT5 phosphorylation in cells can be assayed by flow cytometry to determine the half maximum effective concentration ($EC_{50}$). In one embodiment, as determined in the STAT5 phosphorylation assay, compared with the wild-type IL-2 protein (e.g., human IL-2 set forth in SEQ ID NO: 1), the ability of the IL-2 mutant protein disclosed herein (for example, in the form of an Fc fusion protein) to activate CD25$^+$ cells is reduced by at least 10-fold, 50-fold, 100-fold, 300-fold, 1000-fold, 3000-fold or higher.

In one embodiment, the IL-2 mutant protein disclosed herein maintains or enhances IL-2-mediated activation and proliferation of CD25$^-$ cells relative to the wild-type IL-2. In one embodiment, the CD25$^-$ cells are CD8$^+$ effector T cells or NK cells. In one embodiment, in the STAT5 phosphorylation assay, the ability of the IL-2 mutant protein to activate CD25$^-$ cells is identified by measuring the $EC_{50}$ of the IL-2 mutant protein in activating the STAT5 phosphorylation signal in CD25$^-$ cells. In one embodiment, as determined in the STAT5 phosphorylation assay, compared with the wild-type IL-2 protein (e.g., human IL-2 set forth in SEQ ID NO: 1), the ability of the IL-2 mutant protein disclosed herein to activate CD25$^+$ cells is enhanced by at least 1-fold, such as 2-fold, 3-fold, 4-fold, 5-fold, 6-fold, 7-fold, 8-fold, 9-fold, 10-fold, 20-fold, 50-fold, 100-fold, or 150-fold.

In one embodiment, compared with the wild-type IL-2 protein, the IL-2 mutant protein disclosed herein eliminates or reduces the preference of IL-2 for preferentially activating CD25$^+$ cells. In one embodiment, the CD25$^+$ cells are CD25$^+$ CD8$^+$ T cells. In another embodiment, the CD25$^+$ cells are Treg cells. In one embodiment, in the STAT5 phosphorylation assay, the ability of the IL-2 mutant protein to activate CD25⁻ cells is identified by measuring the $EC_{50}$ of the IL-2 mutant protein in activating the STAT5 phosphorylation signal in CD25⁻ cells and in CD25⁺ cells. For example, the activation preference of the IL-2 mutant protein for CD25⁺ cells is determined by calculating the ratio of the $EC_{50}$ for activation of STAT5 phosphorylation signals on CD25⁻ and CD25⁺ T cells. Preferably, compared with the wild-type protein, the preference of the mutant protein for CD25⁺ is reduced by at least 100-fold, preferably at least 1000-fold, 2000-fold, or 3000-fold.

The Mutant Protein Disclosed Herein

The IL-2 protein is a member of the short chain type I cytokine family with four α-helical bundles (A, B, C, and D). According to the analysis of the crystal structure (PDB: 1Z92), IL-2 has the following amino acid sites that interact with CD25 at amino acid residue positions 35-72: 35, 37, 38, 41, 42, 43, 45, 61, 62, 68, and 72. According to the analysis of the crystal structure (PDB: 2ERJ), IL-2 has the following sites that interact with CD122 at amino acid residue positions 12-23 and amino acid positions 79-92: 12, 13, 15, 16, 19, 20, 23, 79, 81, 82, 83, 84, 87, 88, 91, and 92.

The inventors have found that by introducing specific mutations to the sites that interact with CD25 (i.e., sites 35, 37, 38, 41, 42, 43, 45, 61, 62, 68, and 72) at amino acid residue positions 35-72 of IL-2 (hereinafter referred to as "CD25 binding region"), the binding of IL-2 to IL-2Rα can be reduced or eliminated, while the binding to IL-2Rβ can be maintained or enhanced. The inventors have also found that by introducing specific mutations to the sites that interact with CD122 (i.e., sites 79, 81, 82, 83, 84, 87, 88, 91, and 92) at the amino acid residue positions 79-92 of IL-2 (hereinafter referred to as "CD122 binding region"), the binding of IL-2 to IL-2Rβ can be enhanced. In addition, the inventors also found that mutations in two regions can be combined to provide IL-2 mutants having both reduced or eliminated binding to IL-2Rα and enhanced binding to IL-2Rβ.

Thus, the present invention provides an IL-2 mutant protein comprising at least one mutation compared with the wild-type IL-2 protein (preferably human IL-2, more preferably IL-2 comprising the sequence of SEQ ID NO: 1). The mutation eliminates or reduces the binding affinity for the IL-2Rα receptor and/or enhances the binding affinity for the IL-2Rβ receptor.

CD25 Binding Region Mutation

In one aspect, compared with the wild-type IL-2 protein, the IL-2 mutant protein disclosed herein comprises one or more mutations (preferably at least 3) at the site where IL-2 interacts with its IL-2Rα receptor (CD25), preferably at positions corresponding to positions 35, 37, 38, 41, 42, 43, 45, 61, 62, 68, and 72 of SEQ ID NO: 1. The mutation eliminates or reduces the binding affinity for the IL-2Rα receptor, and preferably enhances binding affinity for the IL-2Rβ. Preferably, the mutations at positions described above are amino acid substitutions. More preferably, the mutations at these positions are substituted residues selected from: position 35: K35D, E; position 37: T37D, E, R, K, F, Y, W; position 38: R38D, E, F, Y, W, A, V; position 41: T41K, R, M, F, Y, W, Q, E; position 42: F42K, R, A, E, Q; position 43: K43E, D, F, Y, W; position 45: Y45R, K; position 61: E61R, K, W, Y, L; position 62: E62R, K, W, Y, L; position 68: E68R, K, W, Y; and position 72: L72R, K, F, Y, W. More preferably, the substituted residues at these positions are selected from: K35D, E; T37E, D, K, W, Y; R38W, E, D, V, F, K; T41E, Y, R, K, Q; F42E, R, K, Q, A; K43E, Y, D, W; Y45K, R; E61K, R, L, W; E68R, Y, W, K; and L72K, F. Furthermore preferably, the substituted residues at these positions are selected from: K35D, E; T37D, E; R38D, E, F; T41E; F42A, E, Q; K43E, D, Y; Y45R, K; E61R, K, W, Y, L; E62R, W; E68R, K, W, Y; and L72K, F. Most preferably, the mutant protein comprises one or more mutations selected from: K35D, E; T37E; R38F, E; T41E; F42A, E; Y45K; and E68Y. In a further embodiment, in the IL-2 mutant protein disclosed herein, the mutation that reduces or eliminates the binding affinity for the IL-2Rα receptor comprises a mutation at the position corresponding to a position of SEQ ID NO: 1 selected from:

K35/T37/R38/T41/K43;
K35/T37/R38/T41/K43/L72;
K35/T37/R38/K43/Y45/L72;
K35/R38/T41/K43;
K35/R38/T41/K43/L72;
K35/R38/T41/K43/E61/L72;
K35/R38/T41/K43/Y45/L72;
K35/R38/T41/K43/Y45/E61/L72;
K35/R38/F42/Y45;
K35/R38/F42/Y45/E61/E68;
K35/R38/F42/E68/L72;
K35/R38/F42/K43/Y45/E68;
K35/R38/F42/K43/Y45/E61/E68;
K35/R38/F42/K43/Y45/E61/E68/L72;
K35/T37/R38/F42;
K35/T37/R38/F42/Y45/E61/E68;
K35/T37/R38/F42/K43/Y45/E61/E68;
K35/T37/R38/T41/F42/K43/Y45/E61/E68;
K35/T37/R38/F42/Y45/E61/E62/E68/L72;
K35/T37/R38/F42/Y45/E62/E68;
K35/T37/R38/F42/K43/E68;
K35/T37/F42/K43;
K35/T37/R38/T41/L72;
K35/T37/R38/T41/F42;
K35/T37/R38/T41/F42/K43/E68;
K35/T37/R38/T41/F42/K43/Y45;
K35/T37/R38/T41/F42/K43/Y45/L72;
T37/R38/T41/F42/K43/Y45;
K35/T37/T41/F42/K43/Y45;
K35/T37/T41/F42/K43/E61/E68/L72;
K35/T41/F42/K43/E68;
K35/T37/R38/T41/K43/Y45;
K35/T37/R38/T41/K43/Y45/L72;
K35/T37/R38/T41/K43/Y45/E61/L72;
K35/T37/R38/K43/L72;
K35/R38/K43/L72;
K35/T37/E61/L72;
K35/Y45/E61/E68;
K35/R38/T41/F42;
K35/R38/T41/F42/Y45;
K35/R38/T41/F42/Y45/E68;
K35/R38/T41/E68;
K35/R38/Y45/E68/L72;
T37/K43/E68/L72;
T37/K43/Y45/E68/L72;
T37/K43/Y45/E61/E68/L72;
T37/F42/Y45/E61/E68/L72;
T37/T41/Y45/E61/E68/L72;
R38/T41/F42/Y45/E61/E68; and
T41/K43/Y45/E61/E68/L72.

In some preferred embodiments, the mutation that reduces or eliminates the binding affinity for the IL-2Rα receptor comprises a combinatorial mutation selected from: K35D/T37K/R38E/T41K/F42Q/K43D/E68Y; K35D/T37D/T41F/F42E/K43D/Y45K; K35D/T37K/R38D/T41E/K43E;

K35D/R38E/T41E/K43E; K35D/R38F/F42E/Y45K; K35E/ R38D/T41E/K43E/L72F; K35D/T37E/R38D/K43E/L72F; K35E/R38D/T41E/K43E/E61K/L72F; K35E/T37D/R38W/ F42Q/Y45K/E61K/E68R; T37E/K43E/Y45K/E68K/L72K; K35E/R38E/T41M/F42E/Y45K; K35D/T37E/R38D/T41E/ K43E; K35D/T37D/R38E/K43E/L72F; K35E/T37D/R38D/ K43E/L72F; K35D/R38D/T41E/K43E/Y45K/E61W/L72F; K35D/T37E/R38D/T41E/K43E/L72F; K35D/R38W/F42E/ E68R/L72F; K35D/T37E/R38D/K43Y/Y45K/L72F; K35E/ T37D/R38W/T41E/F42A/K43F/Y45K; K35D/T37E/R38D/ T41R/F42Q; K35E/R38D/T41E/K43D/L72F; K35E/T41Q/ F42R/K43D/E68Y; K35E/T37Y/R38W/T41Y/F42E/K43E/ Y45K/L72K; K35D/T37E/R38D/K43Y/Y45R/L72F; K35E/T37E/R38D/T41E/K43Y; T37E/T41K/Y45R/E61L/ E68K/L72K; K35E/R38W/F42Q/Y45R/E61W/E68R; K35D/T37E/R38E/T41E/L72F; K35D/T37D/R38D/T41E/ L72F; K35D/R38E/T41E/K43E/L72F; K35E/T37D/R38D/ T41E/K43Y/Y45K; K35D/T37D/F42A/K43E; K35E/ R38E/T41E/K43Y/Y45K/L72F; K35D/R38W/F42E/K43Y/ Y45R/E61R/E68Y; R38K/T41R/F42Q/Y45K/E61Y/E68W; K35E/R38W/F42Q/Y45K/E61L/E68R; K35D/T37E/R38E/ T41E/K43E/Y45K/L72F; K35E/R38D/K43E/L72F; K35E/ R38E/K43E/L72F; K35D/T37E/R38D/L72F; K35E/R38E/ T41E/K43E/L72F; K35E/T37E/R38E/F42A; K35D/R38F/ T41E/F42E/Y45K/E68Y; K35E/T37K/R38E/T41E/K43E/ L72F; K35D/R38D/K43E/L72F; K35D/R38A/T41Q/F42R; K35D/T37E/R38F/F42E/K43E/E68R; K35D/T37E/R38D/ T41E/K43E/Y45K/E61W/L72F; T37D/R38F/T41F/F42E/ K43E/Y45R; K35D/R38W/F42E/K43E/Y45K/E68K; K35E/T37D/R38E/T41E/K43Y; K35E/R38W/F42E/Y45K; K35E/T37D/R38W/F42E/Y45K/E68Y/L72R; K35E/T37D/ R38W/F42Q/Y45R/E62R/E68R; K35E/T37D/T41F/F42A/ K43E/E61W/E68K/L72W; T41K/K43D/Y45R/E61L/ E68K/L72K; K35E/T37E/R38W/F42Q/Y45R/E61R/E68R; K35E/T37D/R38W/F42Q/Y45R/E61K/E68R; K35E/T37D/ R38W/F42Q/Y45K/E61W/E68R; K35E/R38W/F42Q/ Y45K/E61K/E68R; K35E/R38W/F42Q/Y45K/E61W/ E68R; K35E/T37D/R38W/F42Q/Y45K/E61R/E68R; K35E/R38D/Y45K/E68R/L72K; K35E/R38W/F42Q/ Y45R/E61R/E68R; T37E/K43D/E68Y/L72R; K35E/Y45R/ E61L/E68W; K35E/T37D/R38W/F42Q/Y45R/E61R/E68R; K35E/T37D/R38V/F42E/K43W/Y45R/E61L/E68W; K35E/T37A/R38W/F42Q/Y45K/E61R/E68R; K35E/ T37W/R38E/T41Y/F42R/K43D/Y45K/E61K/E68W; K35D/R38W/F42K/K43Y/Y45R/E61R/E68W/L72K; K35E/T37E/E61W/L72K; K35E/R38Y/T41E/E68Y; K35E/ T37E/R38W/F42Q/Y45R/E61K/E68R; T37D/K43D/Y45R/ E61Y/E68K/L72R; K35D/R38W/F42E/K43Y/Y45R/E61R/ E68Y/L72K; T37E/F42R/Y45R/E61Y/E68K/L72K; and K35E/T37D/R38V/F42A/Y45K/E61R/E62W/E68Y/L72R.

In some preferred embodiments, the mutation that reduces or eliminates the binding affinity for the IL-2Rα receptor comprises a mutation at a position selected from: K35/R38/F42/T37; K35/R38/F42/Y45/E61/E68; and K35/R38/F42/Y45/E61/E68/T37. Preferably, the mutation comprises K35E, R38E, F42A, and T37E; or K35E, R38W, F42Q, Y45R/K, E61K/W/R, E68R, and optionally T37D/E. Most preferably, the mutation is a combinatorial mutation selected from: K35E/R38E/F42A/T37E; K35E/R38W/F42Q/Y45K/E61K/E68R; K35E/R38W/F42Q/Y45K/E61W/E68R; K35E/R38W/F42Q/Y45R/E61R/E68R; K35E/R38W/F42Q/Y45K/E61K/E68R/T37D; K35E/R38W/F42Q/Y45R/E61K/E68R/T37D; K35E/R38W/F42Q/Y45K/E61W/E68R/T37D; K35E/R38W/F42Q/Y45K/E61R/E68R/T37D; K35E/R38W/F42Q/Y45R/E61R/E68R/T37D; K35E/R38W/F42Q/Y45R/E61R/E68R/T37E; and K35E/R38W/F42Q/Y45R/E61K/E68R/T37E. Preferably, the IL-2 protein disclosed herein comprising these combinatorial mutations has increased binding affinity for IL-2Rβ relative to the wild-type IL-2 protein; and more preferably, it also has reduced activation preference for $CD25^+$ cells.

In some preferred embodiments, the mutation that reduces or eliminates the binding affinity for the IL-2Rα receptor comprises a mutation at a position selected from: K35/R38/F42/Y45/E61/E68/K43; K35/R38/F42/Y45/E61/E68/K43/L72; K35/R38/F42/Y45/E61/E68/K43/T37; and K35/R38/F42/Y45/E61/E68/K43/T37/T41. Preferably, the mutation comprises: K35D/E, R38W/V/E, F42E/K/R, Y45R/K, E61R/L/K, E68Y/W and K43Y/W/D, and optionally one or more of T37D/W, T41Y and L72K. More preferably, the mutation is a combinatorial mutation selected from: K35D/R38W/F42E/Y45R/E61R/E68Y/K43Y; K35D/R38W/F42E/Y45R/E61R/E68Y/K43Y/L72K; K35D/R38W/F42K/Y45R/E61R/E68W/K43Y/L72K; K35E/R38V/F42E/Y45R/E61L/E68W/T37D/K43W; and K35E/R38E/F42R/Y45K/E61K/E68W/T37W/K43D/T41Y. More preferably, the mutation is: K35D/R38W/F42E/Y45R/E61R/E68Y/K43Y/L72K. Preferably, the IL-2 protein disclosed herein comprising these combinatorial mutations has reduced or eliminated binding affinity for IL-2Rα and increased binding affinity for IL-2Rβ relative to the wild-type IL-2 protein.

In some embodiments, the mutation that reduces or eliminates the binding affinity for the IL-2Rα receptor comprises a mutation at a position selected from: K35/R38/T41/K43; K35/R38/T41/K43/T37; K35/R38/T41/K43/L72; K35/R38/T41/K43/T37/L72; K35/R38/T41/K43/E61/L72; K35/R38/T41/K43/Y45/L72; K35/R38/K43/T37/L72; and K35/R38/K43/T37/L72/Y45. Preferably, the mutation comprises: K35D/E, R38D/E, T41E, and K43E/Y, and optionally one or two selected from T37K/E, Y45K, E61K, and L72F; or preferably the mutation comprises K35D/E, R38D, K43E/Y, T37D/E, and L72F, and optionally Y45K. More preferably, the mutation is a combinatorial mutation selected from: K35D/R38E/T41E/K43E; K35D/T37K/R38D/T41E/K43E; K35E/R38E/T41E/K43E/L72F; K35D/T37E/R38D/T41E/K43E/L72F; K35E/R38D/T41E/K43E/E61K/L72F; K35E/R38E/T41E/K43Y/Y45K/L72F; K35D/T37E/R38D/K43E/L72F; K35E/T37D/R38D/K43E/L72F; and K35D/T37E/R38D/K43Y/Y45K/L72F; More preferably, the mutation is a combinatorial mutation selected from: K35D/T37E/R38D/T41E/K43E/L72F; K35E/R38D/T41E/K43E/E61K/L72F; K35E/R38E/T41E/K43Y/Y45K/L72F; K35D/T37E/R38D/K43E/L72F; K35E/T37D/R38D/K43E/L72F; and K35D/T37E/R38D/K43Y/Y45K/L72F; and most preferably the mutation is K35D/R38E/T41E/K43E. Preferably, the IL-2 mutant protein disclosed herein comprising these combinatorial mutations has reduced or eliminated binding affinity for IL-2Rα and increased binding affinity for IL-2Rβ relative to the wild-type IL-2 protein; and more preferably, it also has reduced activation preference for $CD25^+$ cells.

In some preferred embodiments, the mutation that reduces or eliminates the binding affinity for the IL-2Rα receptor comprises a mutation at a position selected from: K35/R38/F42/Y45/E61/E68; K35/R38/F42/Y45/E61/E68/T37; K35/R38/F42/T37; and K35/R38/T41/K43.

In some preferred embodiments, the mutation that reduces or eliminates the binding affinity for the IL-2Rα receptor comprises a combinatorial mutation selected from: K35E/R38E/F42A/T37E; K35E/R38W/F42Q/Y45K/E61K/E68R; K35E/R38W/F42Q/Y45K/E61W/E68R; K35E/R38W/F42Q/Y45R/E61R/E68R; K35E/R38W/F42Q/Y45K/E61K/E68R/T37D; K35E/R38W/F42Q/Y45R/E61K/E68R/T37D; K35E/R38W/F42Q/Y45K/E61W/E68R/T37D; K35E/R38W/F42Q/Y45K/E61R/E68R/T37D; K35E/R38W/

F42Q/Y45R/E61R/E68R/T37D; K35E/R38W/F42Q/Y45R/ E61R/E68R/T37E; K35E/R38W/F42Q/Y45R/E61K/E68R/ T37E; and K35D/R38E/T41E/K43E. These combinatorial mutations may enable the IL-2 mutant protein disclosed herein to have reduced or eliminated binding affinity for IL-2Rα and increased binding affinity for IL-2Rβ relative to the wild-type IL-2 protein, and results in reduced activation preference for CD25+ cells while maintaining or enhancing activation and/or proliferation of CD25− effector cell.

In some preferred embodiments, the mutation that reduces or eliminates the binding affinity for the IL-2Rα receptor comprises a combinatorial mutation selected from: K35D/ T37E/R38E/T41E/K43E/Y45K/L72F; K35E/R38D/T41E/ K43E/L72F; K35E/R38W/F42Q/Y45K/E61L/E68R; K35D/T37K/R38E/T41K/F42Q/K43D/E68Y; K35D/T37E/ R38D/K43Y/Y45K/L72F; K35E/T37Y/R38W/T41Y/F42E/ K43E/Y45K/L72K; K35D/R38W/F42E/K43E/Y45K/ E68K; K35E/T41Q/F42R/K43D/E68Y; K35D/R38W/ F42E/Y45R/E61R/E68Y/K43Y; K35D/R38F/T41E/F42E/ Y45K/E68Y; K35E/T37K/R38E/T41E/K43E/L72F; and R38K/T41R/F42Q/Y45K/E61Y/E68W.

Advantageously, these combinatorial mutations can be combined with the mutations that increase the binding to IL-2Rβ in the regions 79-92 described herein to provide the IL-2 mutant protein that does not bind to IL-2Rα but binds to IL-2Rβ in an enhanced manner.

CD122 Binding Region Mutation

In yet another aspect, the IL-2 mutant protein disclosed herein may comprise one or more mutations at a site where IL-2 interacts with its β receptor CD122 (i.e., IL-2Rβ), preferably at positions corresponding to positions 79, 81, 82, 83, 84, 87, 88, 91, and 92 of SEQ ID NO: 1, and the mutation enhances the binding affinity for IL-2Rβ. Preferably, the mutations at positions described above are amino acid substitutions. More preferably, the mutations at these positions are substituted residues selected from: H79R, K, Y, W, D, E, Q; R81D, E, N, Q, T, H, Y, W; P82I, T, A; R83E; D84E, N, Q, H, T, V; S87T, D, N, E, Q, K, R, Y, W; N88D, E, Q, H, Y, W; V91T, L, I, M, D, N, E, Q, H; and I92V, L, M, F, Y, W, N, D, E, Q.

In one preferred embodiment, the IL-2 mutant protein disclosed herein comprises one or more mutations, preferably amino acid substitutions, in particular one or more substitutions selected from: H79D, E, Q; R81D, N; P82I, T, A; R83E; S87D, E; V91L, I; and I92L, M, F, Y, at positions corresponding to positions 79, 81, 82, 83, 87, 91, and 92 of SEQ ID NO: 1. In one embodiment, the mutant protein disclosed herein remains unchanged relative to the wild-type IL-2 protein at positions corresponding to positions 12, 13, 15, 16, 19, 20, and 23 of SEQ ID NO: 1.

In some preferred embodiments, the mutation that enhances the binding affinity for IL-2β comprises a mutation at a position selected from H79/R81/S87/I92 and H79/R81/ S87/I92/P82. Preferably, the mutation comprises H79D/E, R81D, S87D/E and I92L/F, and optionally P82T. More preferably, the mutation comprises a combinatorial mutation selected from H79D/R81D/S87D/I92L and H79D/R81D/ P82T/S87D/I92L. Preferably, the combinatorial mutation may enable the IL-2 mutant protein disclosed herein to have significantly increased binding affinity for IL-2Rβ relative to the wild-type IL-2 protein, and more preferably results in enhanced activation and/or proliferation of CD25− effector cell.

In some preferred embodiments, the mutation that enhances the binding affinity for IL-2β comprises a mutation at a position selected from: R81/R83/S87; R81/R83/S87/ I92; R81/P82/R83/S87; and R81/P82/R83/S87/I92; and preferably a mutation at one or two positions of H79 and V91. Preferably, the mutation comprises a combinatorial mutation selected from: R81D, P82T/I/A, R83E, S87E/D; R81D/N, P82T/I/A, R83E, S87E/D, I92/L/M/F/Y; and R81D, R83E, S87E/D; R81D, R83E, S87E/D, I92L, and more preferably one or two of H79D/E/Q and V91L/I. More preferably, the mutation is a combinatorial mutation selected from: H79D/R81D/S87D/I92L; H79D/R81D/P82T/S87D/ I92L; R81D/P82T/R83E/S87E; R81D/P82T/R83E/S87E/ V91L; R81D/P82A/R83E/S87E/V91L; H79E/R81D/P82T/ R83E/S87E/V91L; H79E/R81D/P82I/R83E/S87D; H79Q/ R81D/P82A/R83E/S87E; R81N/P82T/R83E/S87E/V91L/ I92F; H79D/R81N/P82T/R83E/S87E/V91L/I92F; R81D/ P82T/R83E/S87D/I92M; H79E/R81D/P82I/R83E/S87E/ I92M; H79Q/R81D/P82T/R83E/S87D/V91L/I92Y; R81D/ P82I/R83E/S87D/V91I/I92Y; R81D/P82T/R83E/S87D/ I92L; R81D/P82T/R83E/S87D/V91L/I92L; R81D/P82A/ R83E/S87E/I92L; H79E/R81N/P82A/R83E/S87D/I92L; R81D/P82T/R83E/S87E/I92M; R81D/P82A/R83E/S87E/ I92M; H79E/R81D/P82A/R83E/S87E/I92M; R81D/R83E/ S87D/I92L; R81D/R83E/S87E/I92L; H79D/R81D/R83E/ S87D; and H79D/R81D/R83E/S87E/V91I/I92L. Preferably, the combinatorial mutation may enable the IL-2 mutant protein disclosed herein to have significantly increased binding affinity for IL-2Rβ relative to the wild-type IL-2 protein, and more preferably results in enhanced activation and/or proliferation of CD25− effector cell.

In some embodiments, the mutation that enhances the binding affinity for IL-2Rβ is a combinatorial mutation selected from: H79D/R81D/S87D/I92L; H79E/R81D/P82T/ R83E/S87E/V91L; H79E/R81D/P82I/R83E/S87D; H79Q/ R81D/P82A/R83E/S87E; R81D/P82T/R83E/S87D/I92L; R81D/P82T/R83E/S87D/V91L/I92L; R81D/P82A/R83E/ S87E/I92L; H79E/R81N/P82A/R83E/S87D/I92L; R81D/ P82T/R83E/S87E/I92M; R81D/P82A/R83E/S87E/I92M; H79E/R81D/P82A/R83E/S87E/I92M; and H79D/R81D/ R83E/S87E/V91I/I92L. Advantageously, these combinatorial mutations can be combined with the mutations that reduce the binding affinity for IL-2Rα in the regions 35-72 described herein to provide the IL-2 mutant protein that does not bind to IL-2Rα but binds to IL-2Rβ in an enhanced manner.

Combination of CD25 Binding Region Mutation and CD122 Binding Region Mutation

In yet another aspect, the present invention provides an IL-2 mutant protein comprising a CD25 binding region mutation and a CD122 binding region mutation, wherein preferably, the mutant protein has reduced (or eliminated) binding to IL-2Rα and enhanced binding to IL-2Rβ, and more preferably, it also has improved druggability, such as higher expression level and product purity.

In some preferred embodiments, the present invention provides an IL-2 mutant protein comprising a combinatorial mutation selected from the following:

| Combinations | A mutation that reduces or eliminates the binding affinity for IL-2Rα receptor | A mutation that enhances the binding affinity for IL-2RB receptor |
|---|---|---|
| 1 | K35D/T37E/R38E/T41E/K43E/Y45K/L72F/ | H79E/R81D/P82I/R83E/S87D/ |
| 2 | K35E/R38D/T41E/K43E/L72F/ | R81D/P82A/R83E/S87E/I92M/ |
| 3 | K35E/R38W/F42Q/Y45K/E61L/E68R/ | R81D/P82A/R83E/S87E/I92L/ |
| 4 | K35D/T37K/R38E/T41K/F42Q/K43D/E68Y/ | H79E/R81D/P82T/R83E/S87E/V91L/ |
| 5 | K35D/T37E/R38D/K43Y/Y45K/L72F/ | R81D/P82T/R83E/S87D/I92L/ |
| 6 | K35E/T37Y/R38W/T41Y/F42E/K43E/Y45K/L72K/ | H79Q/R81D/P82A/R83E/S87E/ |
| 7 | K35D/R38W/F42E/K43E/Y45K/E68K/ | R81D/P82T/R83E/S87E/I92M/ |
| 8 | K35E/T41Q/F42R/K43D/E68Y/ | H79D/R81D/S87D/I92L/ |
| 9 | K35D/R38W/F42E/Y45R/E61R/E68Y/K43Y/ | H79E/R81N/P82A/R83E/S87D/I92L/ |
| 10 | K35D/R38F/T41E/F42E/Y45K/E68Y/ | R81D/P82T/R83E/S87D/V91L/I92L/ |
| 11 | K35E/T37K/R38E/T41E/K43E/L72F/ | H79E/R81D/P82A/R83E/S87E/I92M/ |
| 12 | R38K/T41R/F42Q/Y45K/E61Y/E68W/ | H79D/R81D/R83E/S87E/V91I/I92L/ |

In some preferred embodiments, the present invention provides an IL-2 mutant protein, wherein the mutant protein has a reduced ability to stimulate signaling in CD25⁺ T cells compared with the wild-type IL-2 protein, and preferably, relative to the wild-type IL-2 protein (for example, the human IL-2 protein of SEQ ID NO: 1), the mutant protein comprises (or only has) a combinatorial mutation selected from:
K35E/R38E/F42A/T37E;
K35E/R38W/F42Q/Y45K/E61K/E68R;
K35E/R38W/F42Q/Y45K/E61W/E68R;
K35E/R38W/F42Q/Y45R/E61R/E68R;
K35E/R38W/F42Q/Y45K/E61K/E68R/T37D;
K35E/R38W/F42Q/Y45R/E61K/E68R/T37D;
K35E/R38W/F42Q/Y45K/E61W/E68R/T37D;
K35E/R38W/F42Q/Y45K/E61R/E68R/T37D;
K35E/R38W/F42Q/Y45R/E61R/E68R/T37D;
K35E/R38W/F42Q/Y45K/E61R/E68R/T37E;
K35E/R38W/F42Q/Y45R/E61R/E68R/T37E; and
K35D/R38E/T41E/K43E.

In some preferred embodiments, the present invention provides an IL-2 mutant protein, wherein the mutant protein has a reduced ability to stimulate signaling in CD25⁺ T cells and enhanced ability to stimulate signaling in CD25⁻ T cells compared with the wild-type IL-2 protein, and preferably, relative to the wild-type IL-2 protein (for example, the human IL-2 protein of SEQ ID NO: 1), the mutant protein comprises (or only has) a combinatorial mutation selected from:
K35D/R38W/F42E/K43E/Y45K/E68K/R81D/P82T/R83E/S87E/I92M; and
K35D/R38F/T41E/F42E/Y45K/E68Y/R81D/P82T/R83E/S87D/V91L/I92L.

Other Mutations

In addition to the mutations in the above regions and positions, the IL-2 mutant protein disclosed herein can also have one or more mutations in other regions or positions, as long as it retains one or more beneficial properties described above. For example, the IL-2 mutant protein disclosed herein may also comprise a substitution at position 125, such as C125S, C125A, C125T, or C125V, to provide additional advantages such as improved expression, homogeneity, or stability (see, for example, U.S. Pat. No. 4,518,584). Those skilled in the art know how to determine additional mutations that can be incorporated into the IL-2 mutant protein disclosed herein.

The sequence difference between the IL-2 mutant protein and the wild-type protein can be expressed in terms of sequence identity or in terms of the difference in the number of amino acids between the two. In one embodiment, the IL-2 mutant protein has at least 85%, 86%, 87%, 88%, or 89% identity, preferably more than 90% (preferably 95%) but preferably no more than 97% and more preferably no more than 96% identity to the wild-type protein. In another embodiment, in addition to CD25 binding region mutation, CD122 binding region mutation, or a combinatorial mutation of both mutations described herein, there may be no more than 15, such as 1-10, or 1-5 mutations, between the IL-2 mutant protein and the wild-type protein. In one embodiment, the additional mutation may be a conservative substitution. In one embodiment, the additional mutation may be a mutation that confers other improved properties on IL-2.

2. Fusion Protein and Immunoconjugate

The present invention also provides a fusion protein comprising the IL-2 mutant protein disclosed herein. In one preferred embodiment, the IL-2 mutant protein disclosed herein is fused to another polypeptide, such as albumin, and preferably an antibody Fc fragment, which can provide improved pharmacokinetic properties. Preferably, the Fc fragment comprises a mutation that reduces or removes the effector function, such as an L234A/L235A or L234A/L235E/G237A mutation that reduces the binding to an Fcγ receptor. Preferably, the Fc-containing fusion protein has an increased serum half-life. In one preferred embodiment, the Fc-containing fusion protein also has reduced effector functions mediated by the Fc region, such as ADCC, ADCP or CDC.

The present invention also provides an immunoconjugate comprising the IL-2 mutant protein disclosed herein and an antigen-binding molecule. Preferably, the antigen-binding molecule is an immunoglobulin molecule, particularly an IgG molecule, an antibody, or an antibody fragment, and more particularly a Fab molecule or an scFv molecule. In some embodiments, the antigen-binding molecule specifically binds to an antigen present on a tumor cell or in tumor environment, such as an antigen selected from: fibroblast activation protein (FAP), A1 domain of tenascin-C (TNC A1), A2 domain of tenascin-C (TNC A2), extra domain B (EDB) of fibronectin, carcinoembryonic antigen (CEA), and melanoma-associated chondroitin sulfate proteoglycan (MCSP). Thus, the immunoconjugate disclosed herein can target the tumor cell or the tumor environment after being administrated to a subject, thereby providing further therapeutic benefits, such as the feasibility of treatment at lower doses and the consequent low side effects, and enhanced anti-tumor effects.

In the fusion protein and immunoconjugate disclosed herein, the IL-2 mutant protein disclosed herein can be linked, either directly or through a linker, to another molecule or antigen-binding molecule, and in some embodiments, a proteolytic cleavage site is provided therebetween.

3. Polynucleotide, Vector, and Host

The present invention provides a nucleic acid encoding any of the IL-2 mutant proteins, fusions or conjugates above. The polynucleotide sequence encoding the mutant protein disclosed herein can be generated by de novo solid phase DNA synthesis or by PCR mutagenesis of an existing sequence encoding the wild-type IL-2 using methods well known in the art. In addition, the polynucleotide and the nucleic acid disclosed herein may comprise a segment encoding a secretion signal peptide and are operably linked to a segment encoding the mutant protein disclosed herein so that secretory expression of the mutant protein disclosed herein can be directed.

The present invention also provides a vector comprising the nucleic acid disclosed herein. In one embodiment, the vector is an expression vector, such as a eukaryotic expression vector. The vector includes, but is not limited to, a virus, a plasmid, a cosmid, a lambda phage, or a yeast artificial chromosome (YAC). In a preferred embodiment, the expression vector disclosed herein is pYDO_017 expression vector (SEQ ID NO: 13).

In addition, the present invention also provides a host cell comprising the nucleic acid or the vector. Host cells suitable for replicating and supporting the expression of the IL-2 mutant protein, the fusion or the immunoconjugate are well known in the art. Such cells can be transfected or transduced with a particular expression vector, and a large number of cells comprising vectors can be cultivated for inoculation in large-scale fermenters, so as to obtain sufficient IL-2 mutants, fusions or immunoconjugates for clinical application. In one embodiment, the host cell is eukaryotic. In another embodiment, the host cell is selected from a yeast cell and a mammalian cell (e.g., a CHO cell or a 293 cell). For example, the polypeptide may be produced in a bacterium, particularly when glycosylation is not required. After expression, the polypeptide can be isolated from the bacterial cell paste in a soluble fraction and can be further purified. In addition to prokaryotes, eukaryotic microorganisms such as filamentous fungi or yeast are cloning or expression hosts for the vector suitable for encoding the polypeptide, including fungal and yeast strains in which the glycosylation pathway has been "humanized", which results in the production of the polypeptide with a partially or fully human glycosylation pattern. See Gerngross, *NatBiotech*, 22, 1409-1414 (2004) and Li et al., *NatBiotech*, 24, 210-215 (2006). Examples of available mammalian host cell lines include SV40 transformed monkey kidney CV1 lines (COS-7), human embryonic kidney lines (293 or 293T cells, as described, for example, in Graham et al., *JGenVirol* 36, 59 (1977)), baby hamster kidney cells (BHK), mouse Sertoli cells (TM4 cells, as described, for example, in Mather, *BiolReprod* 23, 243-251 (1980)), monkey kidney cells (CV1), African green monkey kidney cells (VERO-76), human cervical cancer cells (HELA), canine kidney cells (MDCK), buffalo rat liver cells (BRL3A), human lung cells (W138), human liver cells (HepG2), mouse mammary tumor cells (MMT060562), TRI cells (as described, for example, in Mather et al., *AnnalsN.Y.AcadSci* 383, 44-68 (1982)), MRCS cells, and FS4 cells. Other available mammalian host cell lines include Chinese hamster ovary (CHO) cells, including dhfr-CHO cells (Urlaub et al., *ProcNatlAcadSciUSA* 77, 4216 (1980)), and myeloma cell lines such as YO, NS0, P3X63, and Sp2/0. In one embodiment, the host cell is a eukaryotic cell, preferably a mammalian cell such as a Chinese hamster ovary (CHO) cell, a human embryonic kidney (HEK) cell, or a lymphocyte (e.g., YO, NS0, and Sp20 cells).

4. Preparation Method

In a further aspect, the present invention provides a method for preparing the IL-2 mutant protein, the fusion or the conjugate disclosed herein, wherein the method comprises culturing a host cell comprising a nucleic acid encoding the protein, the fusion or the conjugate under conditions suitable for expression of the IL-2 mutant protein, the fusion or the conjugate, as provided above, and optionally isolating the protein, the fusion or the conjugate from the host cell (or the host cell culture medium).

5. Assay

The IL-2 mutant protein provided herein can be identified, screened, or characterized for its physical/chemical properties and/or biological activity through a variety of assays known in the art.

In one aspect, the IL-2 mutant protein disclosed herein can be tested for its binding activity to an IL-2 receptor. For example, the binding to a human IL-2Rα or β protein can be determined by methods known in the art, such as ELISA, Western blotting, and the like, or by the exemplary methods disclosed in the examples herein. For example, the flow cytometry can be used, wherein cells such as yeast display cells that are transfected to express the mutant protein on the cell surface react with a labeled (e.g., biotin-labeled) IL-2Rα or β protein. Alternatively, the binding of the mutant protein to the receptor, including the binding kinetics (e.g., the $K_D$ value), can be determined by a bio-layer interferometry (BLI) assay using a recombinant mutant protein-Fc fusion. In some embodiments, the BLI assay as described in the examples is used.

In yet another aspect, the ability of the IL-2 mutant protein to bind to the IL-2 receptor can be measured indirectly by measuring the signaling and/or immune activation at the downstream of receptor binding.

Thus, in some embodiments, an assay for identifying the IL-2 mutant protein having a biological activity is provided. Biological activity may include, for example, the ability to induce proliferation of T cells and/or NK cells with IL-2 receptors, the ability to induce IL-2 signaling in T cells and/or NK cells with IL-2 receptors, the ability to produce interferon (IFN)-γ as a secondary cytokine by NK cells, reduced ability to induce apoptosis in T cells, ability to induce tumor regression and/or to improve survival, and reduced in vivo toxicity properties, such as reduced vascular permeability. The present invention also provides an IL-2 mutant protein having such biological activities in vivo and/or in vitro.

Various methods known in the art can be used for determining the biological activities of the IL-2. For example, an assay suitable for testing the ability of the IL-2 mutant protein disclosed herein to stimulate IFN-γ production by NK cells may comprise the steps of: incubating the cultured NK cells with the IL-2 mutant protein, the fusion or the immunoconjugate disclosed herein, and measuring the IFN-γ concentration in the culture medium by ELISA. IL-2 signaling induces several signaling pathways and involves JAK (Janus kinase) and STAT (signal transducers and activators of transcription) signaling molecules.

The interaction of the IL-2 with the β and γ subunits of the receptor results in phosphorylation of the receptor and JAK1 and JAK3 (which bind to the β and γ subunits, respectively). STAT5 then binds to the phosphorylated receptor and is phosphorylated on a very important tyrosine residue. This results in dissociation of STAT5 from the receptor, dimerization of STAT5, and translocation of STAT5 dimers to the nucleus where they facilitate the transcription of target genes. Thus, the ability of the mutant IL-2 polypeptide to induce signaling via the IL-2 receptor can be assessed, for example, by measuring the phosphorylation of STAT5. Details of this method have been disclosed in the examples. For example, PBMCs can be treated with the mutant IL-2 polypeptide, the fusion or the immunoconjugate disclosed herein, and the level of phosphorylated STAT5 is determined by flow cytometry.

In addition, the proliferation of T cells or NK cells in response to IL-2 can be measured by incubating the T cells or NK cells isolated from blood with the mutant IL-2 polypeptide or immunoconjugate disclosed herein, followed by determination of ATP content in the lysates of the treated cells. Prior to treatment, T cells may be pre-stimulated with phytohemagglutinin (PHA-M). This assay allows sensitive quantification of the number of viable cells, and a number of suitable alternative assays (e.g., [3H]-thymidine incorporation assay, cell titration GloATP assay, AlamarBlue assay, WST-1 assay, and MTT assay) are also known in the art.

Furthermore, the effect of the mutant IL-2 on tumor growth and survival can be assessed in a variety of animal tumor models known in the art. For example, heterografts of human cancer cell lines can be implanted into immunodeficient mice and treated with the mutant IL-2 polypeptide, the fusion or the immunoconjugate disclosed herein. The in vivo toxicity of the mutant IL-2 polypeptide, the fusion, and the immunoconjugate disclosed herein can be determined based on mortality, life-time observations (visible symptoms of adverse effects, e.g., behavior, body weight, and body temperature), and clinical and anatomical pathology (e.g., measurement of blood chemistry values and/or histopathological analysis). For example, the vascular permeability induced by IL-2 treatment can be examined with a vascular leakage reporter molecule in a pretreated vascular permeability animal model. Preferably, the vascular leakage reporter molecule is large enough to reveal the permeability of the wild-type IL-2 form for pretreatment.

6. Screening Method

In still another aspect, the present invention provides a method for eliminating or reducing the binding affinity of the IL-2 protein for the IL-2Rα receptor and/or enhancing the binding affinity for the IL-2Rβ receptor, including introducing the mutation or combinatorial mutation described herein to the wild-type IL-2 protein, and identifying (for example, using the aforementioned assay method) the mutant protein with altered binding affinity for ILRα or β, and/or improved biological activity, such as one or more of the properties described above for the IL-2 mutant protein disclosed herein relative to the wild-type IL-2 protein. In some embodiments, the parental wild-type IL-2 protein used as a mutation template preferably has at least 80%, or at least 95% or 99% or higher identity to SEQ ID NO: 1, and more preferably is an IL-2 protein derived from human.

7. Pharmaceutical Composition and Pharmaceutical Preparation

The present invention also comprises a composition (including a pharmaceutical composition or a pharmaceutical preparation) comprising the IL-2 mutant protein or the fusion or immunoconjugate thereof, and a composition comprising the polynucleotide encoding the IL-2 mutant protein or the fusion or immunoconjugate thereof. Such compositions can further optionally comprise suitable pharmaceutical adjuvants, such as a pharmaceutical carrier and a pharmaceutical excipient known in the art, including buffers.

The pharmaceutical carrier applicable to the present invention may be sterile liquid, such as water and oil, including those derived from petroleum, animals, plants or synthesis, such as peanut oil, soybean oil, mineral oil, sesame oil, etc. Water is a preferred carrier when the pharmaceutical composition is administered intravenously. Saline solutions, aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, etc. For use and application of excipients, see "Handbook of Pharmaceutical Excipients", 5th Edition, R. C. Rowe, P. J. Seskey and S. C. Owen, Pharmaceutical Press, London, Chicago. The composition may further comprise a small quantity of wetting agent, emulsifier, or pH buffer, if desired. The compositions may take the form of a solution, a suspension, an emulsion, a tablet, a pill, a capsule, a powder, a sustained release preparation, and the like. Oral preparations may comprise standard carriers, such as pharmaceutical grade mannitol, lactose, starch, magnesium stearate, and saccharin.

The pharmaceutical preparation comprising the IL-2 mutant protein can be formulated by mixing the IL-2 mutant protein, the fusion or the immunoconjugate disclosed herein of a desired purity with one or more optional pharmaceutical excipients (*Remington's Pharmaceutical Sciences*, 16 th edition, Osol, A. eds. (1980)), preferably in the form of a lyophilized preparation or an aqueous solution. An exemplary lyophilized antibody preparation is described in U.S. Pat. No. 6,267,958. The aqueous antibody preparation includes those described in U.S. Pat. No. 6,171,586 and WO 2006/044908, and the latter preparation comprises a histidine-acetate buffer. In addition, a sustained release preparation can be prepared. Suitable examples of the sustained release preparation include a semipermeable matrix of a solid hydrophobic polymer comprising a protein. The matrix is in the form of a shaped article, such as a film or a microcapsule.

The pharmaceutical composition or preparation disclosed herein can further comprise one or more other active ingredients which are required for a specific indication being treated, preferably active ingredients having complementary activities that do not adversely affect one another. For example, it may be desirable to further provide other anti-cancer active ingredients, such as a chemotherapeutic agent and a PD-1 axis binding antagonist (e.g., an anti-PD-1 antibody, an anti-PD-L1 antibody or an anti-PD-L2 antibody). The active ingredients are suitably combined in an amount effective for an intended purpose.

Thus, in one embodiment, the composition further comprises a second therapeutic agent. For example, the second therapeutic agent can be an immune checkpoint inhibitor. For example, the second therapeutic agent may be one or more selected from the group including but not limited to, for example, an anti-CTLA-4 antibody, an anti-CD47 antibody, an anti-PD-1 antibody, an anti-PD-L1 antibody, an anti-CD40 antibody, an anti-OX40 (also referred to as CD134, TNFRSF4, ACT35, and/or TXGP1L) antibody, an anti-LAG-3 antibody, an anti-CD73 antibody, an anti-CD137 antibody, an anti-CD27 antibody, an anti-CSF-1R antibody, a TLR agonist, and a small molecule antagonist of IDO or TGFβ. Preferably, the second therapeutic agent is a PD-1 antagonist, particularly an anti-PD-1 antibody, an anti-PD-L1 antibody, an anti-LAG-3 antibody, and an anti-CD47 antibody. In addition to be an immunotherapeutic agent, the second therapeutic agent may also be another radiotherapeutic or chemotherapeutic agent.

8. Combination Product

In one aspect, the present invention further provides a combination product comprising the mutant protein or the fusion or immunoconjugate thereof disclosed herein, and one or more other therapeutic agents (e.g., a chemotherapeutic agent, other antibodies, a cytotoxic agent, a vaccine, and an anti-infective active agent). The combination product disclosed herein can be used in a therapeutic method disclosed herein.

In some embodiments, the present invention provides a combination product, wherein the aforementioned other therapeutic agents refer to, for example, a therapeutic agent, such as an antibody, which is effective to stimulate an immune response and thus further enhance, stimulate or upregulate the immune response in a subject. In some embodiments, the aforementioned other antibodies refer to, e.g., an anti-PD-1 antibody, an anti-PD-L1 antibody, an anti-PD-L2 antibody, an anti-LAG-3 antibody, an anti-CTLA-4 antibody or an anti-TIM-3 antibody.

In some embodiments, the combination product is used for preventing or treating a tumor. In some embodiments, the tumor is cancer, e.g., gastrointestinal cancer (such as gastric cancer, rectal cancer, colon cancer, and colorectal cancer), skin cancer (such as melanoma), renal cell carcinoma, bladder cancer, or non-small cell lung cancer. In some embodiments, the combination product is used for preventing or treating an infection, such as bacterial infection, viral infection, fungal infection, protozoal infection, and the like.

9. Therapeutic Method and Use

As used herein, the terms "individual" and "subject" can be used interchangeably and refer to a mammal. The mammals include, but are not limited to, domesticated animals (e.g., cows, sheep, cats, dogs, and horses), primates (e.g., human and non-human primates such as monkeys), rabbits and rodents (e.g., mice and rats). In particular, a subject is a human.

As used herein, the term "treating" refers to a clinical intervention intending to alter the natural progress of a disease in an individual being treated. Desired therapeutic effects include, but are not limited to, preventing the occurrence or recurrence of diseases, alleviating symptoms, reducing any direct or indirect pathological outcomes of diseases, preventing metastasis, delaying disease progression, improving or alleviating conditions, and improving prognosis.

In one aspect, the present invention provides a method for stimulating the immune system of a subject, comprising administering to the subject an effective amount of a pharmaceutical composition comprising the IL-2 mutant protein, the fusion or the immunoconjugate disclosed herein. The IL-2 mutant protein disclosed herein has high activity and selectivity for $CD25^-$ $CD122^+$ effector cells (cytotoxic $CD8^+$ T cells and NK cells), and has a reduced and removed stimulation effect on $CD25^+$ Treg cells. The IL-2 mutant protein disclosed herein can be used at a low dose to stimulate the immune system of the subject.

Thus, in some embodiments, the present invention relates to a method for enhancing the immune response of the body of a subject, comprising administering to the subject an effective amount of any of the IL-2 mutant proteins or the fusions or immunoconjugates thereof described herein. In some embodiments, the IL-2 mutant protein or the fusion or immunoconjugate thereof disclosed herein is administered to a subject with a tumor to stimulate an anti-tumor immune response. In other embodiments, the antibodies or the antigen-binding fragments thereof disclosed herein are administered to a subject with an infection to stimulate an anti-infection immune response. In one embodiment, the IL-2 mutant protein disclosed herein can be used in combination with a Treg-depleting antibody (e.g., FcγR-mediated Treg depletion) to further reduce the immunosuppressive effect caused by Treg. In one embodiment, the IL-2 mutant protein disclosed herein can be administered in combination with an immune checkpoint inhibitor (e.g., in combination with anti-PD-1 and anti-CTLA-4 antibodies) to, for example, enhance cancer immunotherapy effect.

In another aspect, the present invention relates to a method for treating a disease, such as tumor, cancer and infection, in a subject, wherein the method comprises administering to the subject an effective amount of any of the IL-2 mutant proteins or the fusions or immunoconjugates thereof described herein.

The cancer may be at an early, intermediate or advanced stage, or may be a metastatic cancer. In some embodiments, the tumor or tumor cell can be selected from colorectal tumor, ovarian tumor, pancreatic tumor, lung tumor, liver tumor, breast tumor, renal tumor, prostate tumor, gastrointestinal tumor, melanoma, cervical tumor, bladder tumor, glioblastoma, and head and neck tumor. In some embodiments, the cancer can be selected from colorectal cancer, ovarian cancer, pancreatic cancer, lung cancer, liver cancer, breast cancer, renal cancer, prostate cancer, gastrointestinal cancer, melanoma, cervical cancer, bladder cancer, glioblastoma, and head and neck cancer. In some embodiments, the tumor is melanoma, renal cell carcinoma, colorectal cancer, bladder cancer, or non-small cell lung cancer.

In another aspect, the present invention relates to a method for treating an infectious disease, e.g., chronic infection, in a subject, wherein the method comprises administering to the subject an effective amount of any of the IL-2 mutant proteins or the fragments thereof, or an immunoconjugate, a multispecific antibody, or a pharmaceutical composition comprising the antibodies or the fragments described herein. In one embodiment, the infection is virus infection.

In some embodiments, the method disclosed herein further comprises administering to the subject one or more therapies in combination (e.g., therapeutic modalities and/or other therapeutic agents), in addition to administering the IL-2 mutant protein or the fusion or conjugate thereof disclosed herein. In some embodiments, the therapeutic modality includes a surgical treatment and/or a radiation therapy. In some embodiments, the method disclosed herein further comprises administering at least one additional immunostimulatory antibody, e.g., an anti-PD-1 antibody, an anti-PD-L1 antibody, an anti-LAG-3 antibody, an anti-CD43 antibody, and/or an anti-CTLA-4 antibody, which can be, e.g., a fully human, chimeric, or humanized antibody.

In some embodiments, the anti-PD-1 antibody is selected from IBI308 (sintilimab, WO2017/025016A1), MDX-1106 (nivolumab, OPDIVO), Merck 3475 (MK-3475, pembrolizumab, KEYTRUDA) and CT-011 (pidilizumab). In some embodiments, the anti-PD-1 antibody is MDX-1106. In some embodiments, the anti-PD-1 antibody is nivolumab (CAS Registry Number: 946414-94-4). In some further embodiments, the IL-2 mutant protein or the fragment thereof used alone or in combination with a PD-1 antagonist can also be administered in combination with one or more other therapies, e.g., therapeutic modalities and/or other therapeutic agents. In some embodiments, the therapeutic modalities include a surgery (e.g., a tumor resection), a radiation therapy (e.g., an external beam therapy that involves a three-dimensional conformal radiation therapy in which an irradiation region is designed), a partial irradiation (e.g., an irradiation directed to a preselected target or an organ), a focused irradiations, and the like.

In some embodiments, a method for treating a disease (e.g., a tumor) is provided herein, comprising administering to a subject the mutant protein disclosed herein and a CTLA-4 antagonist antibody. The anti-CTLA-4 antibody may be, for example, an antibody selected from YERVOY® (ipilimumab or antibody 10D1, as described in PCT publication No. WO 01/14424), tremelimumab (formerly known as ticilimumab, CP-675,206), and anti-CTLA-4 antibodies described in the following publications: WO 98/42752; WO 00/37504; U.S. Pat. No. 6,207,156; Hurwitz et al. (1998), *Proc. Natl. Acad. Sci. USA* 95(17):10067-10071; Camacho et al. (2004), *J. Clin. Oncology* 22(145): Abstract No. 2505 (antibody CP-675206); and Mokyr et al. (1998), *Cancer Res.* 58:5301-5304.

In some embodiments, a method for treating a disease (e.g., a tumor) is provided, comprising administering to a subject the anti-mutant protein described herein and an anti-LAG-3 antagonist antibody. The anti-LAG-3 antibody may be, for example, an antibody selected from: antibodies 25F7, 26H10, 25E3, 8B7, 11F2 and 17E5 described in US 2011/0150892 and WO 2014/008218, antibodies comprising CDRs or variable regions of the above antibodies; BMS-986016; and IMP731 described in US 2011/007023.

In some embodiments, the IL-2 mutant protein disclosed herein can be administered in combination with a chemotherapy or a chemotherapeutic agent. In some embodiments, the IL-2 mutant protein disclosed herein can be administered in combination with a radiation therapy or a radiotherapeutic agent. In some embodiments, the IL-2 mutant protein disclosed herein can be administered in combination with a targeted therapy or a targeted therapeutic agent. In some embodiments, the IL-2 mutant protein disclosed herein can be administered in combination with an immunotherapy or an immunotherapeutic agent, such as a monoclonal antibody.

The mutant protein disclosed herein (or the pharmaceutical composition comprising the same, or the fusion or immunoconjugate thereof, and optionally an additional therapeutic agent) can be administered by any suitable method, including parenteral administration, intrapulmonary administration, intranasal administration, and, if required by local treatment, intralesional administration. Parenteral infusion includes intramuscular, intravenous, intra-arterial, intraperitoneal, or subcutaneous administration. The medicaments may be administered by any suitable means, such as injection, e.g., intravenous or subcutaneous injection, to some extent depending on short-term or long-term treatment. Various administration schedules are encompassed herein, including, but not limited to, single administration or multiple administrations at multiple time points, bolus injection, and pulse infusion.

In order to prevent or treat a disease, the appropriate dosage of the mutant protein disclosed herein (used alone or in combination with one or more additional therapeutic agents) will depend on the type of the disease to be treated, the type of the antibody, severity and progression of the disease, the purpose for which the antibody is administered (prevention or treatment), previous treatments, clinical history of a patient, responses to the antibody, and the discretion of an attending physician. The antibody is suitably administered to a patient through a single treatment or through a series of treatments.

In a further aspect, the present invention also provides use of the IL-2 mutant protein, composition, immunoconjugate, and fusion disclosed herein in preparation of a drug for use in the aforementioned method (e.g., for treatment).

The following examples are described to assist in understanding the present invention. The examples are not intended and should not be interpreted in any way as limiting the protection scope of the present invention.

EXAMPLES

Example 1: Design and Construction of an Interleukin-2 Mutant Library

Design of an Interleukin-2 Mutant Library

According to the crystal structure (PDB:1Z92) (as shown in FIG. 1) of the complex of interleukin-2 (referred to as IL-2) and its alpha receptor CD25 (referred to as IL-2Rα), the listed IL-2 residues at interaction sites were mutated as per Table 1. The original amino acids at each site accounted for 50%, and the remaining 50% was divided equally by the "mutant amino acids" in Table 1. The theoretical diversity of the library designed for the binding site of IL-2 to IL-2Rα was $3\times8\times8\times9\times6\times6\times3\times6\times6\times5\times6\approx2.0\times10^8$, and the library was named as IBYDL029 (Innoventbio Yeast Display Library).

TABLE 1

Mutation sites for the IBYDL029 library

| Site | Amino acid residue | Mutant amino acid | Diversity |
|---|---|---|---|
| 35 | Lys(K) | D, E | 3 |
| 37 | Thr(T) | D, E, R, K, F, Y, W | 8 |
| 38 | Arg(R) | D, E, F, Y, W, A, V | 8 |
| 41 | Thr(T) | K, R, M, F, Y, W, Q, E | 9 |
| 42 | Phe(F) | K, R, A, E, Q | 6 |
| 43 | Lys(K) | E, D, F, Y, W | 6 |
| 45 | Tyr(Y) | R, K | 3 |
| 61 | Glu(E) | R, K, W, Y, L | 6 |
| 62 | Glu(E) | R, K, W, Y, L | 6 |
| 68 | Glu(E) | R, K, W, Y | 5 |
| 72 | Leu(L) | R, K, F, Y, W | 6 |

Figure 2:
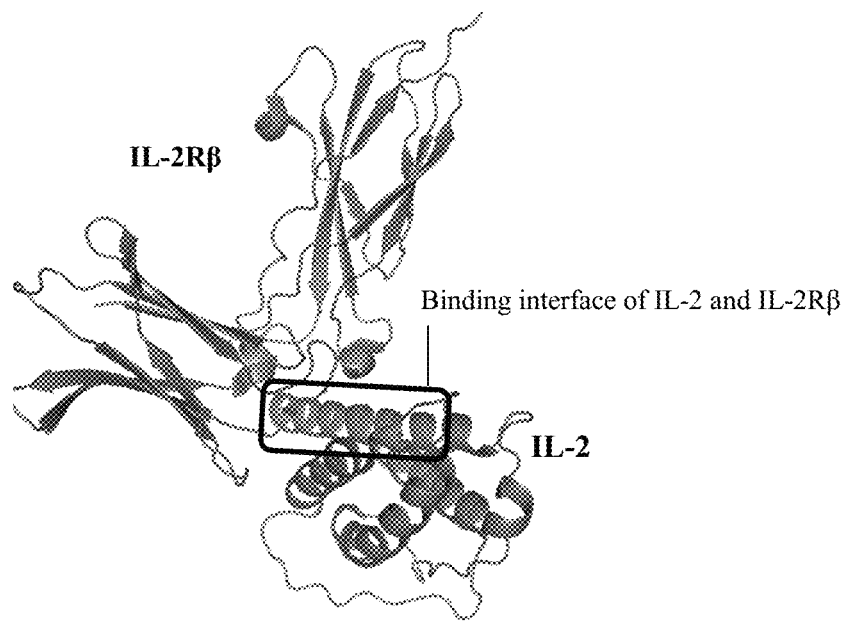
FIG. 2 shows the crystal structure of a complex of IL-2 and IL-2Rβ.

According to the crystal structure (PDB:2ERJ) (as shown in FIG. 2) of the complex of IL-2 and its β receptor CD122 (referred to as IL-2Rβ), the listed IL-2 residues at interaction sites were mutated as per Table 2. The original amino acids at each site accounted for 50%, and the remaining 50% was divided equally by the "mutant amino acids" in Table 2. Due to the large number of the binding sites of IL-2 to IL-2Rβ and large theoretical diversity of the library, the library was split into two small libraries. The mutant library at positions 12-23 was IBYDL030 with a theoretical diversity of $12\times8\times9\times12\times13\times7\times12\approx1.1\times10^7$, and the mutant library at positions 79-92 was IBYDL031 with a theoretical diversity of $8\times9\times4\times2\times7\times10\times7\times10\times11\approx3.1\times10^7$.

TABLE 2

Mutation sites for the IBYDL030-IBYDL031 libraries

| Site | Amino acid residue | Mutant amino acid | Diversity |
|---|---|---|---|
| 12 | Leu(L) | V, T, D, N, E, Q, R, K, F, Y, W | 12 |
| 13 | Gln(Q) | D, E, V, L, F, N, T | 8 |
| 15 | Glu(E) | D, N, Q, H, W, K, R, Y | 9 |
| 16 | His(H) | D, N, Q, H, W, Y, F, T, I, R, K | 12 |
| 19 | Leu(L) | V, I, M, T, D, N, E, Q, Y, H, R, K | 13 |
| 20 | Asp(D) | E, N, Q, T, V, L | 7 |
| 23 | Met(M) | V, L, D, N, E, Q, F, Y, W, R, K | 12 |
| 79 | His(H) | R, K, Y, W, D, E, Q | 8 |
| 81 | Arg(R) | D, E, N, Q, T, H, Y, W | 9 |
| 82 | Pro(P) | I, T, A | 4 |
| 83 | Arg(R) | E | 2 |
| 84 | Asp(D) | E, N, Q, H, T, V | 7 |
| 87 | Ser(S) | T, D, N, E, Q, K, R, Y, W | 10 |
| 88 | Asn(N) | D, E, Q, H, Y, W | 7 |
| 91 | Val(V) | T, L, I, M, D, N, E, Q, H | 10 |
| 92 | Ile(I) | V, L, M, F, Y, W, N, D, E, Q | 11 |

Construction of an Interleukin-2 Mutant Library

The wild-type IL-2 (uniprot: P60568, aa21-153, C125S, referred to as IL-2$^{WT}$) was placed between the two BamHI restriction enzyme cutting sites of yeast surface display plasmid pYDC011. The sequence of IL-2$^{WT}$ was set forth in SEQ ID NO: 1 in the present invention. A C125S mutation was introduced to position 125 of the sequence to avoid the formation of a disulfide-bridged IL-2 dimer. The specific steps of plasmid construction were as follows:
1. fragments were amplified using primers AMP0210 and AMP0211, with IL-2$^{WT}$ gene as a template;
2. plasmid pYDC011 was digested with BamHI (New England Biolab, Catalog No. R3136V), followed by gel extraction (QIAGEN Gel Extraction Kit, Catalog No. 28704);
3. the amplified product and digested product were extracted from 1% agarose gel;
4. after extraction, the products were homologously recombined in vitro using One Step Cloning Kit (Vazyme Catalog No. C113-02);
5. the recombined product was transferred into *Escherichia coli* Top10 competent cells (Tiangen, Catalog No. CB104-02), and the cells were coated on an ampicillin-resistant LB plate and cultured at 37° C. overnight;
6. after the growing monoclonal colonies were verified by sequencing, the correct plasmid was named as pYDC035.

According to existing literature, the IL-2 mutant IL-2$^{3X}$ does not bind to IL-2Rα, and has unchanged binding to IL-2Rβ (Rodrigo Vazquez-Lombardi et al., *Nature Communications*, 8:15373, DOI: 10.1038/ncomms15373); and the IL-2 mutant IL-2$^{H9}$ has enhanced binding to IL-2Rβ, as well as unchanged binding to IL-2Rα (Aron M. Levin et al., *Nature*, Vol 484, p 529-533, DOI: 10.1038/nature10975). IL-2$^{3X}$ and IL-2$^{H9}$ were displayed on the surface of yeasts and used as controls. The sequences of IL-2$^{3X}$ and IL-2$^{H9}$ were set forth in SEQ ID NOs: 2 and 3, respectively. The two proteins also comprised a C125S mutation, which were identical to IL-2$^{WT}$.

The required primers (as shown in FIG. 3) were designed according to the construction schemes of libraries in Table 1 and Table 2 and synthesized by Suzhou Genewiz Biological Technology Co., Ltd.

IBYDL029 library DNA amplification: 1. fragment 029-F was amplified with primers AMP0191 and AMP0200 using pYDC035 as a template; 2. fragment 029-R was amplified with primers AMP0201 and AMP0199 using pYDC035 as a template; 3. fragments 029-F and 029-R were extracted from gel and used as a PCR amplification template to amplify the full-length fragment 029 with primers AMP0191 and AMP0199.

IBYDL030 library DNA amplification: 1. fragment 030-F was amplified with primers AMP0191 and AMP0224 using pYDC035 as a template; 2. fragment 030-R was amplified with primers AMP0222 and AMP0199 using pYDC035 as a template; 3. fragments 030-F and 030-R were extracted from gel and used as a PCR amplification template to amplify the full-length fragment 030 with primers AMP0191 and AMP0199.

IBYDL031 library DNA amplification: 1. fragment 031-F was amplified with primers AMP0191 and AMP0225 using pYDC035 as a template; 2. fragment 031-R was amplified with primers AMP0223 and AMP0199 using pYDC035 as a template; 3. fragments 031-F and 031-R were extracted from gel and used as a PCR amplification template to amplify the full-length fragment 031 with primers AMP0191 and AMP0199.

100 μg of plasmid pYDC011 was digested with BamHI, and extracted using a PCR product recovery kit (QIAGEN PCR Purification Kit, Catalog No. 28104) to give a sufficient number of linear plasmids. The linear plasmids and library DNAs were mixed at a ratio of 4 μg:12 μg. The mixture of each library and linear plasmid was electrotransfected into EBY100 yeast strain according to the existing method (Lorenzo Benatuil et al., An improved yeast transformation method for the generation of very large human antibody libraries. *Protein Engineering, Design & Selection* vol. 23 no. 4 pp. 155-159, 2010). After electrotransfection, the libraries were gradiently diluted and coated on SD-Trp (TAKARA, Catalog No. 630309) plates. The number of growing colonies was counted. The actual diversities of the libraries obtained were: IBYDL029: 4.2×10$^8$, IBYDL030: 4.5×10$^8$, and IBYDL031: 3.8×10$^8$, all greater than the theoretical diversity of the library.

Example 2: Preparation and Biotin Labeling of IL-2$^{WT}$-FC, IL-2$^{3X}$-FC, IL-2Rα and IL-2Rβ Proteins Construction of Expression Plasmids The IL-2$^{WT}$ and IL-2$^{3X}$ gene sequences were placed between two BamHI restriction enzyme cutting sites in the vector pYDO_017 to express a fusion protein of IL-2$^{WT}$-FC and IL-2$^{3X}$-FC. The Fc used in the present invention is Fc of human IgG1 (L234A, L235A, referred to as FcLALA). An avi tag and a His6 tag were respectively linked to the C-terminus of the sequences (set forth in SEQ ID NOs: 11 and 12) of IL-2Rα (Uiprot: P01589, aa22-217) and IL-2Rβ (Uiprot: P14784, aa27-240), which were constructed into pTT5 vectors, for the expression of IL-2Rα and IL-2Rβ proteins.

Expression and Purification of Proteins

The plasmid expression vector constructed above was transferred into HEK293-F (Invitrogen, Catalog No. R79007) cells using a chemical transfection method. The cultured HEK293-F cells were transiently transfected with a chemical transfection reagent polyethyleneimine (referred to as PEI, Polysciences, Catalog No. 23966) according to a scheme provided by the manufacturer. 1/10 (v/v) of the final volume of Opti-MEM medium (Gibco, Catalog No. 31985-070) was taken as a buffer, added with plasmids, mixed well, and filtered with a 0.22 μm filter for later use. PEI (Polysciences, 23966) was added to the plasmids from the previous step (the mass ratio of plasmids to PEI was 1:3 in 293F cells), mixed well and incubated at room temperature for 10 min to give a DNA/PEI mixture. The DNA/PEI mixture was gently poured into HEK293 cells, mixed well, and cultured at 37° C., 8% $CO_2$ for 24 h, followed by the addition of VPA (Sigma, Catalog No. P4543-100G) to reach a final concentration of 2 mM. Then 2% (v/v) Feed (1 g/L Phytone Peptone+1 g/L Difco Select Phytone) was added and the resulting mixture was cultivated for 6 days.

The cell culture medium expressing the fusion protein of IL-$2^{WT}$-FC and IL-$2^{3X}$-FC was centrifuged at 13000 rpm for 20 min. The supernatant was collected, and purified by pre-packed column Hitrap Mabselect Sure (GE, 11-0034-95). The procedures were as follows: the packing column was equilibrated with 5-fold column volume of equilibration buffer (0.2 M Tris, 1.5 M NaCl, pH7.2) before purification; the collected supernatant was passed through the column, and then the column was washed with 10-fold column volume of equilibration buffer to remove non-specific binding proteins; the packing was washed with 5-fold column volume of elution buffer (1M sodium citrate, pH3.5), and the eluent was collected. 80 μL of Tris (2 M Tris) was added per 1 mL of eluent, and the mixture was buffer-exchanged into PBS (Gibco, 70011-044) using an ultrafiltration concentration tube (Shanghai Tuokai Biotechnology Co., Ltd., MCPM02C67), and then the concentration was determined. 100 μg of purified protein was taken with its concentration adjusted to 1 mg/mL. The protein purity was determined by gel filtration column (TOSOH Catalog No. 18675).

Cell culture media expressing IL-2Rα and IL-2Rβ proteins were centrifuged at 13000 rpm for 20 min. The supernatants were collected, and filtered with a 0.22 μm filter; nickel column (5 mL Histrap excel, GE, 17-3712-06) was soaked in 0.1 M NaOH for 2 h in advance, then washed with 10-fold column volume of ultrapure water to remove alkali liquor, and equilibrated with 5-fold column volume of binding buffer (20 mM Tris, 300 mM NaCl, pH7.4); the cell supernatants were passed through the column, and then the column was washed with 10-fold column volume of washing buffer (20 mM Tris, 300 mM NaCl, 10 mM imidazole, pH7.4) to remove non-specific binding impure proteins; finally, the target protein was eluted with 5-fold column volume of eluent (20 mM Tris, 300 mM NaCl, 100 mM imidazole, pH7.4), buffer-exchanged into PBS using an ultrafiltration concentration tube, and purified to determine the expression level and purity of proteins, see Table 3.

TABLE 3

Expression level and purity of proteins

| Protein | Expression level (mg/L) | Purity (SEC-HPLC) |
|---|---|---|
| IL-$2^{WT}$-FC | 18 | 45% |
| IL-$2^{3X}$-FC | 34 | 70% |
| IL-2Rα | 6 | 65% |
| IL-2Rβ IH(in house) | 6 | 72% |

Biotin Labeling of IL-2Rα and IL-2Rβ IH Proteins

The IL-2Rα and IL-2Rβ proteins were labeled with biotin by enzymatic method, of which the procedures were as follows: an appropriate amount of IL-2Rα and IL-2Rβ IH protein solutions were added with 1/10 (m/m) mass of His-BirA protein (uniprot: P06709), followed by ATP (Sigma, Catalog No. A2383-10G) with a final concentration of 2 mM, $MgCl_2$ with a final concentration of 5 mM, and D-biotin (AVIDITY, Catalog No. K0717) with a final concentration of 0.5 mM; the mixtures were incubated at 30° C. for 1 h, and purified by Superdex200 increase (GE, 10/300GL, 10245605) to remove excess biotin and His-BirA; the purified samples were verified by Streptavidin (SA) sensor (PALL, 18-5019) from Fortebio to confirm the successful biotin labeling. The biotin-labeled IL-2Rα and IL-2Rβ IH proteins obtained in this example were referred to as IL-2Rα-Biotin and IL-2Rβ IH-Biotin, respectively.

Example 3: Screening of IL-2 Mutant Library to Give IL-$2^{mutant}$ and Differential Staining Screening for IL-$2^{mutant}$ with High Affinity for IL-2R/3

The yeast-based IL-$2^{mutant}$ display libraries IBYDL029, IBYDL030 and IBYDL031 have a diversity of $2.0\times10^8$, $1.1\times10^7$, and $3.1\times10^7$, respectively, from each of which $2.0\times10^9$ yeast cells were taken for culture and induction. Due to the large diversity of the IBYDL029 library, magnetic-activated cell sorting was performed using the MACS system from Miltenyi in the first round of screening. First, $2\times10^9$ yeast cells were incubated in FACS washing buffer (lx PBS, containing 1% bovine serum albumin) for 30 min at room temperature, and the buffer contained 500 nM biotin-labeled commercial IL-21Rβ (Acro Biosystems, labeled with EZ-Link Sulfo-NHS-LC-Biotin, referred to as IL-21Rβ-Biotin). The cells were washed once with 50 mL of pre-cooled FACS buffer and resuspended in 10 mL of the same buffer, followed by addition of 40 μL of streptavidin microbeads (Miltenyi biotec, Catalog No. 130-090-485) and incubation at 4° C. for 15 min. The mixture was centrifuged at 3000 rpm for 3 min. After discarding the supernatant, the cells were resuspended in 10 mL of FACS buffer. The resulting cell suspension was loaded on a Miltenyi LS column. After loading, the column was washed three times, with 3 mL of FACS buffer each time. The Miltenyi LS column was removed from the magnetic field and eluted with 5 mL of growth medium. The eluted yeast cells were collected and incubated overnight at 30° C. Due to the relatively small diversities of IBYDL030 and IBYDL031 libraries, the first round of sorting could be directly performed using flow cytometer. $1\times10^8$ and $2.5\times10^8$ yeast cells were taken from the above libraries respectively, washed three times with FACS buffer, and incubated in FACS buffer containing 100 nM IL-21Rβ-Biotin and Anti Flag antibody (Sigma, Catalog No. F18041, diluted at a ratio of 1:1000) at room temperature for 30 min. After being washed twice with FACS buffer, the cells were mixed with FACS washing buffer containing SA-PE (streptavidin-PE, Thermo Fisher, Catalog No. S21388, diluted at a ratio of 1:200) and goat anti-mouse conjugated with Alex Flour-647 (Thermo Fisher, Catalog No. A21235, diluted at a ratio of 1:200), and incubated away from light at 4° C. for 15 min. The cells were washed twice with pre-cooled FACS buffer, resuspended in 1 mL of buffer and transferred into a separator tube with a filter. The cells were sorted using FACS MoFlo_XDP (Beckman), and the sorted yeast cells were incubated overnight at 30° C.

Cells of each library obtained through the first round of screening were induced by shaking at 20° C. for 24 h to display IL-$2^{mutant}$, and the second round of sorting was performed using flow cytometer. $3\times10^7$ yeast cells taken from each library were washed three times with FACS buffer, added to FACS buffer containing IL-21Rβ-Biotin of different concentrations (029: 300 nM, 030/031: 100 nM) and Anti Flag antibody, and incubated at room temperature for 30 min. After being washed twice with FACS buffer, the cells were mixed with FACS washing buffer containing SA-PE and goat anti-mouse conjugated with Alex Flour-647, and incubated away from light at 4° C. for 15 min. The cells were washed twice with pre-cooled FACS washing buffer, resuspended in 1 mL of buffer, and transferred into a separation tube with a filter. The cells were sorted using MoFlo_XDP, and the sorted yeast cells were incubated overnight at 30° C. The sorting scheme of the third round was the same as that of the second round. After three rounds of screening, the monoclones were picked and sent for sequencing.

After three rounds of screening using IL-2Rβ-Biotin, 53 mutant sequences, 0 mutant sequence, and 71 mutant sequences were obtained from IBYDL029, IBYDL030 and IBYDL031, respectively.

The self-made IL-2Rβ IH-Biotin obtained in Example 2 was used for the screening of the second batch in the yeast-based IL-2 mutant display libraries IBYDL029, IBYDL030 and IBYDL031. The magnetic-activated cell sorting was performed using MACS system in the first round of screening. First, 2×10$^9$ yeast cells taken from each library were incubated in FACS washing buffer containing IL-2Rβ IH-Biotin of different concentrations (IBYDL029: 500 nM, IBYDL030/031: 200 nM) at room temperature for 30 min. The subsequent steps were the same as those in the magnetic bead sorting of the first batch, and the sorted yeast cells were incubated overnight at 30° C. The second and third rounds of sorting were performed using flow cytometer. The concentrations of IL-2Rβ IH-Biotin adopted in both rounds were: IBYDL 029: 500 nM and IBYDL 030/031: 100 nM, and the remaining steps were the same as those in the second and third rounds of screening of the first batch.

After three rounds of screening using IL-2Rβ IH-Biotin, the monoclones were picked and sent for sequencing. Additional 25 mutant sequences, 0 mutant sequence, and additional 41 mutant sequences were obtained from IBYDL029, IBYDL030 and IBYDL031, respectively.

Differential Staining of IL-2$^{Mutant}$

Yeast cells comprising a single mutant sequence after sequencing were induced by shaking at 20° C. for 24 h to display IL-2$^{mutant}$, and stained together with their receptors IL-2Rα-Biotin and IL-2Rβ IH-Biotin, respectively. The specific steps were as follows:

I staining analysis of IL-2$^{mutant}$ displayed yeast cells together with IL-2Rα-Biotin:
  1. 1×10$^6$ cells from each sample were centrifuged to discard the supernatant, and washed with FACS buffer once for later use;
  2. the cells were added to 100 μL of FACS buffer containing 50 nM IL-2Rα-Biotin and Anti Flag antibody, and incubated at room temperature for 30 min;
  3. the mixture was centrifuged at 3000 rpm, 4° C. for 3 min, and washed with pre-cooled FACS buffer twice;
  4. 100 μL of FACS buffer containing SA-PE and goat anti-mouse conjugated with Alex Flour-647 was added, and the mixture was incubated on ice for 20 min away from light;
  5. after being washed twice with pre-cooled FACS buffer, the cells were resuspended in 100 μL of buffer, and the binding level of IL-2$^{mutant}$ to IL-2Rα was assayed by a flow cytometer (BD, ACCURI C6).

II Staining Analysis of IL-2$^{mutant}$ Displayed Yeast Cells Together with IL-2Rβ IH-Biotin:
  1. 1×10$^6$ cells from each sample were centrifuged to discard the supernatant, and washed with FACS buffer once for later use;
  2. the cells were added to 100 μL of FACS buffer containing IL-2Rβ IH-Biotin (30 nM-100 nM) and Anti Flag antibody, and incubated at room temperature for 30 min;
  3. following steps 3-5 described above, the binding level of IL-2$^{mutant}$ to IL-2Rβ was assayed.

It can be seen from the staining results of flow cytometry that: the mean fluorescence intensity of binding of 53 IL-2$^{mutant}$ obtained through the screening of the first batch of IBYDL029 (see FIG. 4A for the specific sequences) to IL-2Rα was close to that of IL-2$^{3X}$, i.e., neither of them bound to IL-2Rα; and the mean fluorescence intensity of binding to 2R13 was stronger than that of IL-2$^{3X}$, but weaker than that of IL-2$^{H9}$. The 12 mutations with the strongest binding signal to IL-2Rβ are listed in Table 3-1 below. The 25 IL-2$^{mutant}$ obtained through the screening of the second batch (see FIG. 4B for the specific sequences) did not bind to IL-2Rα; and compared with IL-2$^{3X}$, the binding to IL-2Rβ was improved to different degrees. The 14 mutations with the strongest binding signal to IL-2Rβ are listed in Table 3-1 below. The 112 IL-$2^{mutant}$ obtained through the screening of the two batches of IBYDL031 bound to IL-2Rα and IL-2Rβ, and the 25 mutations with stronger binding signal to IL-2Rβ (see FIG. 4C for the specific sequences) are listed in Table 3-1 below. The mean fluorescence intensity of binding of the 25 mutations to IL-2Rβ was significantly stronger than that of IL-$2^{3X}$ and equivalent to or slightly weaker than that of IL-$2^{H9}$.

TABLE 3-1

| IL-$2^{mutant}$ with high binding signal to IL-2Rβ identified by differential staining | | | |
|---|---|---|---|
| IL-$2^{mutant}$ from IBYDL029 | | IL-$2^{mutant}$ from IBYDL031 | |
| Y29D2 | Y34H1 | Y27D2 | Y35B6 |
| Y30B4 | Y34C2 | Y27D4 | Y35E1 |
| Y29B2 | Y33G4 | Y27E1 | Y36D6 |
| Y30D4 | Y34B3 | Y28F1 | Y36B2 |
| Y29A5 | Y33B5 | Y27F6 | Y35C2 |
| Y29C5 | Y33F4 | Y27C1 | Y35A5 |
| Y29A6 | Y33G6 | Y28A5 | Y35D2 |
| Y30B1 | Y34F4 | Y32D5 | Y35G4 |
| Y29A2 | Y33B4 | Y27C5 | Y36E3 |
| Y30E1 | Y33B1 | Y28F5 | Y35H1 |
| Y29A1 | Y33C5 | Y27C2 | Y36E5 |
| Y29D6 | Y33A6 | Y28A2 | Y36G2 |
| | Y33A5 | | Y35E6 |
| | Y33A4 | | |

In addition, mutations derived from IBYDL029 were combined with mutations derived from IBYDL031 (see FIG. 4D for the specific sequences) to give new mutants with no binding to IL-2Rα and enhanced binding to IL-2Rβ, as shown in Table 3-2.

TABLE 3-2

| Combinatorial mutations derived from IBYDL029 and IBYDL031 | | |
|---|---|---|
| Clone No. | IBYDL029 mutant | IBYDL031 mutant |
| Y01 | Y30C2 | Y27C1 |
| Y02 | Y29A4 | Y27C2 |
| Y03 | Y30C1 | Y27C5 |
| Y04 | Y27A3 | Y27D2 |
| Y05 | Y29D6 | Y27D4 |
| Y06 | Y29F4 | Y27E1 |
| Y07 | Y30G4 | Y27F6 |
| Y08 | Y29F3 | Y28A2 |
| Y09 | Y30B4 | Y28A5 |

TABLE 3-2-continued

Combinatorial mutations derived from IBYDL029 and IBYDL031

| Clone No. | IBYDL029 mutant | IBYDL031 mutant |
|---|---|---|
| Y10 | Y30E3 | Y28F1 |
| Y11 | Y30E6 | Y28F5 |
| Y12 | Y30B6 | Y32D5 |

Example 4: Expression of IL-2$^{mutant}$-FC Fusion Protein and Determination of its Affinity (Avidity) for a Receptor Construction of Expression Plasmids The IL-2$^{mutant}$ sequence was placed between two BamHI restriction enzyme cutting sites in the vector pYDO_017 to express an IL-2$^{mutant}$-FC fusion protein. The yeast surface display plasmids containing the IL-2$^{mutant}$ genes were mixed in equal proportions as a template, and fragments were amplified by two primers. After amplification, DNA fragments were extracted from 1% agarose gel. pYDO_017 BamHI digestion vector was homologously recombined with the extracted fragments, and the recombinant product was transformed into E. coli competent cells to give the expression plasmids of IL-2$^{mutant}$-FC verified by sequencing.

Expression and Purification of IL-2$^{mutant}$-FC Fusion Protein

A vector containing the gene encoding the fusion protein was transferred into HEK293 cells using a chemical transfection method. The cultured HEK293 cells were transiently transfected using chemical transfection reagent PEI according to a scheme provided by the manufacturer. First, the plasmid DNA and the transfection reagent were prepared in a superclean bench. 3 mL of Opti-MEM medium (Gibco, Catalog No. 31985-070) was added to a 50 mL centrifuge tube, followed by 30 μg of the corresponding plasmid DNA. The Opti-MEM medium containing the plasmid was filtered with a 0.22 μm filter, and then added with 90 μg of PEI (1 g/L), and the mixture was let stand for 20 min. The DNA/PEI mixture was gently poured into 27 mL of HEK293 cells, mixed well, and cultured at 37° C., 8% $CO_2$ for 20 h, followed by the addition of VPA to reach a final concentration of 2 mM. Then 2% (v/v) of Feed was added, and the resulting mixture was cultured for 6 days.

After culturing, the mixture was centrifuged at 13000 rpm for 20 min, and the supernatant was collected, and purified by pre-packed column Hitrap Mabselect Sure. The procedures were as follows: the packing column was equilibrated with 5-fold column volume of equilibration buffer (0.2 M Tris, 1.5 M NaCl, pH7.2) before purification; the collected supernatant was passed through the column, and then the column was washed with 10-fold column volume of equilibration buffer to remove non-specific binding proteins; the packing was washed with 5-fold column volume of elution buffer (1M sodium citrate, pH3.5), and the eluent was collected; 80 μL of Tris (2 M Tris) was added per 1 mL of eluent, and the mixture was buffer-exchanged into PBS using an ultrafiltration concentration tube, and then the concentration was determined. 100 μg of purified protein was taken with its concentration adjusted to 1 mg/mL. The protein purity was determined by gel filtration column. The expression and purification results of 47 IL-2$^{mutant}$ disclosed herein are shown in Table 4.

TABLE 4

Expression level and purity of the IL-2$^{mutant}$-FC fusion protein

| IL-2$^{mutant}$ | Expression level (mg/L) | Purity (SEC-HPLC) | IL-2$^{mutant}$ | Expression level (mg/L) | Purity (SEC-HPLC) |
|---|---|---|---|---|---|
| IL-2$^{WT}$ | 18 | 45% | Y34F4 | 42 | 97% |
| IL-2$^{3X}$ | 34 | 70% | Y34H1 | 17 | 90% |
| Y29A1 | No expression | N.D | Y27C1 | 7 | 35% |
| Y29A2 | 37 | 79% | Y27C2 | 1 | 10% |
| Y29A5 | 12 | 73% | Y27C5 | 1 | 15% |
| Y29A6 | 1 | 37% | Y27D2 | 1 | 28% |
| Y29B2 | 77 | 88% | Y27D4 | 7 | 9% |
| Y29C5 | 10 | 60% | Y27F6 | 9 | 14% |
| Y29D2 | 17 | 80% | Y28A2 | 33 | 88% |
| Y29D6 | 23 | 60% | Y28A5 | 15 | 21% |
| Y30B1 | 20 | 70% | Y28F5 | 9 | 12% |
| Y30B4 | No expression | N.D | Y32D5 | 8 | 47% |
| Y30D4 | No expression | N.D | Y01 | 12 | 95% |
| Y30E1 | 60 | 78% | Y02 | 7 | 80% |
| Y33A4 | 33 | 96% | Y03 | 63 | 95% |
| Y33A5 | 28 | 96% | Y04 | 30 | 89% |
| Y33A6 | 35 | 95% | Y05 | 13 | 91% |
| Y33B1 | 27 | 99% | Y06 | 18 | 85% |
| Y33B4 | 10 | 97% | Y07 | 63 | 88% |
| Y33B5 | 34 | 96% | Y08 | 13 | 85% |
| Y33C5 | 36 | 98% | Y09 | 3 | 94% |
| Y33F4 | 32 | 95% | Y10 | 80 | 92% |
| Y33G4 | 2 | N.D | Y11 | 37 | 94% |
| Y34B3 | No expression | N.D | Y12 | No expression | N.D |
| Y34C2 | 3 | N.D | | | |

Note:
N.D: not detected

Determination of Affinity of IL-2$^{mutant}$-FC Fusion Protein for its Receptor

The equilibrium dissociation constant ($K_D$) for binding of 34 IL-2$^{mutant}$-FC fusion proteins disclosed herein to their receptors was determined by bio-layer interferometry (BLI).

A BLI affinity assay was performed according to the prior art (Estep, P, et al., High throughput solution based measurement of antibody-antigen affinity and epitope binning. MAbs, 2013.5(2): p. 270-8). After the sensor was equilibrated off-line in an assay buffer for 20 min, according to the established method, the affinity of the candidate IL-2$^{mutant}$-FC fusion protein for IL-2Rα and IL-2Rβ was measured with Octet Red96: first, the baseline was established by detecting online for 120 s; then IL-2Rα-Biotin or IL-2Rβ 1H-Biotin was immobilized to the SA sensor (PALL, 18-5019); the sensor immobilized with IL-2Rα-Biotin or IL-2Rβ 1H-Biotin was exposed to a solution containing 100 nM IL-2$^{mutant}$-FC fusion protein until to a plateau (100 s), and then transferred to an assay buffer for dissociation for at least 2 min to measure the association and dissociation. Kinetic analysis was performed on the assay results using a 1:1 binding model.

In the assay described above, the affinity $K_D$ values of 36 IL-2$^{mutant}$-FC fusion proteins expressed by HEK293-F cells for their receptors are shown in Table 5.

TABLE 5

Affinity $K_D$ value of IL-2$^{mutant}$-FC for its receptor

| IL-2$^{mutant}$ | IL-2Rα affinity (M) | IL-2Rβ affinity (M) | IL-2$^{mutant}$ | IL-2Rα affinity (M) | IL-2Rβ affinity (M) |
|---|---|---|---|---|---|
| IL-2$^{WT}$ | 1.0E-08 | 4.1E-08 | Y01 | N.B | 6.9E-11 |
| IL-2$^{3X}$ | N.B | 1.6E-08 | Y02 | N.B | 3.1E-10 |
| Y29A2 | Very weak | 4.8E-10 | Y03 | Very weak | 1.4E-10 |
| Y29A5 | N.B | 3.4E-10 | Y04 | N.B | 1.3E-10 |

TABLE 5-continued

Affinity $K_D$ value of IL-2$^{mutant}$-FC for its receptor

| IL-2$^{mutant}$ | IL-2Rα affinity (M) | IL-2Rβ affinity (M) | IL-2$^{mutant}$ | IL-2Rα affinity (M) | IL-2Rβ affinity (M) |
| --- | --- | --- | --- | --- | --- |
| Y29A6 | N.B | 1.8E−09 | Y05 | N.B | 9.6E−11 |
| Y29B2 | N.B | 3.4E−10 | Y06 | N.B | 4.8E−10 |
| Y29C5 | N.B | 4.2E−10 | Y07 | N.B | 1.6E−10 |
| Y29D2 | Very weak | 8.5E−11 | Y08 | N.B | 4.1E−10 |
| Y29D6 | N.B | 1.9E−10 | Y09 | N.B | 1.4E−10 |
| Y30B1 | N.B | 1.9E−10 | Y10 | N.B | 1.1E−10 |
| Y30E1 | N.B | 5.9E−09 | Y11 | N.B | 3.4E−10 |
| Y33A4 | N.B | 2.2E−09 | Y27D2 | 3.2E−08 | 7.2E−09 |
| Y33A5 | N.B | 2.6E−09 | Y27F6 | 7.4E−10 | 1.3E−09 |
| Y33A6 | N.B | 2.1E−09 | Y28A2 | 1.3E−09 | 3.0E−10 |
| Y33B1 | N.B | 2.4E−09 | Y28A5 | 2.4E−10 | 3.8E−09 |
| Y33B4 | N.B | 3.5E−09 | | | |
| Y33B5 | N.B | 2.5E−09 | | | |
| Y33C5 | N.B | 2.3E−09 | | | |
| Y33F4 | N.B | 2.1E−09 | | | |
| Y34F4 | N.B | 2.4E−09 | | | |
| Y34H1 | N.B | 4.5E−10* | | | |

Note:
*Koff limits;
N.B: none binding

It can be seen from the results of the above table that: (1) the affinity of each IL-2$^{mutant}$-FC fusion protein obtained by library screening for IL-2Rβ was significantly enhanced compared with that of IL-2$^{WT}$ or IL-2$^{3X}$; (2) except for Y27D2, Y27F6, Y28A2, and Y28A5, the affinity of each IL-2$^{mutant}$-FC fusion protein for IL-2Rα was significantly reduced or absent compared with that of IL-2$^{WT}$, and was close to that of IL-2$^{3X}$. Based on the results of Table 4 and Table 5, Y29A2, Y29B2, Y30E1, Y07, Y10, Y33A4, Y33A5, Y33A6, Y33B1, Y33B4, Y33B5, Y33C5, Y33F4 and Y34F4 were selected for in vitro functional assays.

Example 5: In Vitro Functional Assay for IL-2$^{mutant}$-FC

Due to higher affinity for IL-2Rα than IL-2Rβ and IL-2Rγ, IL-2$^{WT}$ will preferentially bind to IL-2Rα on the cell surface, then recruit IL-2Rβγ. The downstream p-STAT5 signals are released by IL-2Rβγ to stimulate the proliferation of T cells and NK cells. As the IL-2Rα is present on the surface of Treg cells but absent on the surface of effector T cells and NK cells, normally the IL-2$^{WT}$ will preferentially stimulate the Treg cell proliferation and down regulate the immune response. Since the IL-2$^{mutant}$ does not bind to the IL-2Rα, the preference of the IL-2$^{mutant}$ for preferentially stimulating Treg cell proliferation is eliminated and meanwhile the number of effector T cells and NK cells is effectively increased by stimulating T cells and NK cells proliferation, thus improving the anti-tumor effect.

In this example, the elimination of the activation preference of each mutant for CD25$^+$ cells was verified by detecting the activation effect of each IL-2$^{mutant}$-FC on p-STAT5 signals of primary human CD8$^+$ T cells, and the mutant with a high activation effect on CD25$^-$ cells was screened. The specific steps are as follows:
1. Thawing PBMC cells:
    a) PBMC cells (Allcells, Catalog No. PB005F, 100 M package) were taken out from liquid nitrogen, and then rapidly placed in a 37° C. water bath for thawing;
    b) the cells were added to 10 mL of pre-warmed X-VIVO15 (Lonza, Catalog No. 04-418Q) culture medium containing 5% human AB serum (GemCell, Catalog No. 100-512) and 1‰ DNase (STRMCELL, Catalog No. 07900), centrifuged at 400 G and 25° C. for 10 min (the subsequent centrifugation was under the same condition) and washed once;
    c) 20 mL of culture medium was added to resuspend the cells, and the cells were cultured overnight in a 37° C. carbon dioxide incubator.
2. Purifying Human CD8$^+$ T Cells:
    a) the cell suspension obtained in step 1 was pipetted, and after centrifugation, the supernatant was discarded;
    b) a mixture of 1 mL of Robosep buffer (STEMCELL, Catalog No. 20104), 100 μL of human AB serum, and 100 μL of negative screening antibody in human CD8$^+$ T cell purification kit (Invitrogen, Catalog No. 11348D) was added to resuspend the cells;
    c) after mixing well, the cells were incubated for 20 min at 4° C. and shaken every 5 min;
    d) after incubation, 10 mL of Robosep buffer was added, and the cells were centrifuged and washed twice;
    e) meanwhile, 1 mL of magnetic microspheres (human CD8$^+$ T cell purification kit) was taken, and 7 mL of Robosep buffer was added; the mixture was placed on a magnetic frame for 1 min to discard the supernatant, and the magnetic microspheres were pre-washed;
    f) the microspheres and the cells were resuspended with 1 mL of Robosep buffer, and after mixing well, the mixture was subjected to rotary incubation for 30 min at room temperature;
    g) after incubation, 6 mL of Robosep buffer was added and the mixture was placed on a magnetic frame for 1 min, followed by the collection of the supernatant;
    h) the collected liquid was placed on the magnetic frame for 1 min, and the supernatant was collected;
    i) centrifugation was performed to discard the supernatant, the cells were resuspended using a preheated T culture medium, and the cell density was adjusted to 1×10$^6$/mL;
    j) ⅓ of the cells were taken to stimulate the expression of CD25 later, and the remaining cells were placed in a 37° C. carbon dioxide incubator for static culture overnight.
3. Stimulating CD8$^+$ T cells to express CD25:
    a) ⅓ of the CD8$^+$ T cells purified in step 2 were taken, into which magnetic microspheres of an anti-human CD3/CD28 antibody (GIBCO, Catalog No. 11131D) were added (the ratio of cells to microspheres was 3:1);
    b) the mixture was placed in a 37° C. carbon dioxide incubator for static culture for three days;
    c) 10 mL of culture medium was added to wash the cells twice;
    d) the culture medium was added to adjust the cell density to 1×10$^6$/mL, and the cells were placed in a 37° C. carbon dioxide incubator for static culture for 2 days.
4. Detecting the purity and expression level of the cells:
    a) an anti-human CD8-PE antibody (Invitrogen, Catalog No. 12-0086-42), an anti-human CD25-PE antibody (eBioscience, Catalog No. 12-0259-42), and an isotype control antibody (BD, Catalog No. 556653) were adopted to detect CD8 and CD25 of the cells;
    b) the cells in step 2 were CD8$^+$ CD25$^-$ T cells, and the cells in step 3 were CD8$^+$ CD25$^+$ T cells.

Figure 5A:
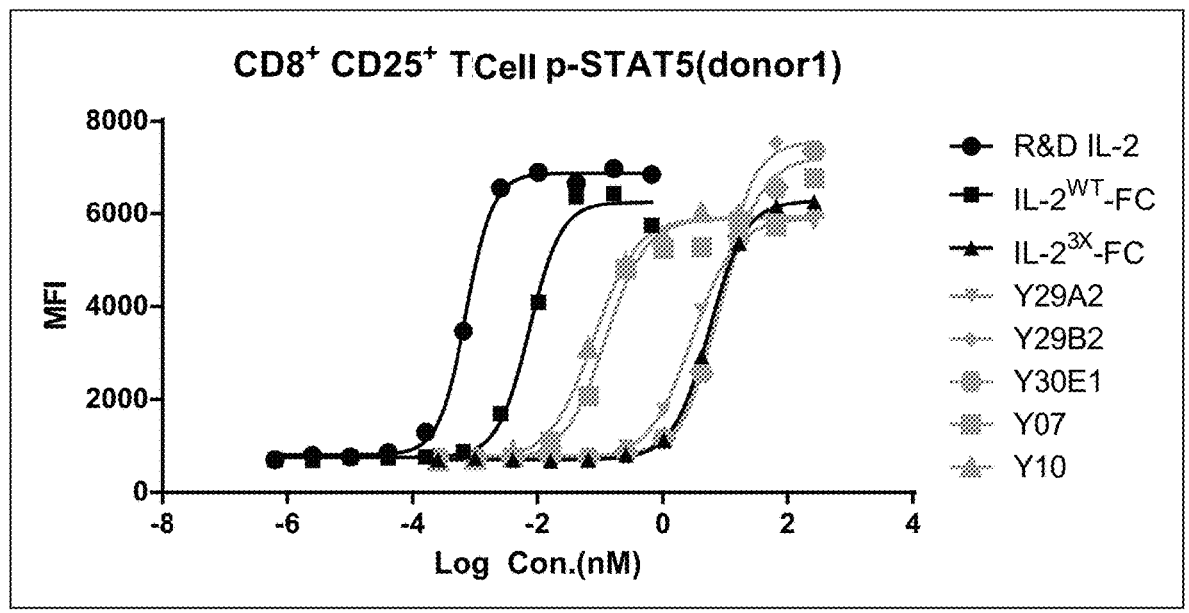
FIGS. 5A-D show curves of some screened and constructed IL-2$^{mutant}$-FC fusion proteins that activate p-STAT5 signals on CD8$^+$ CD25$^-$/CD25$^+$ T cells.
Figure 5B:
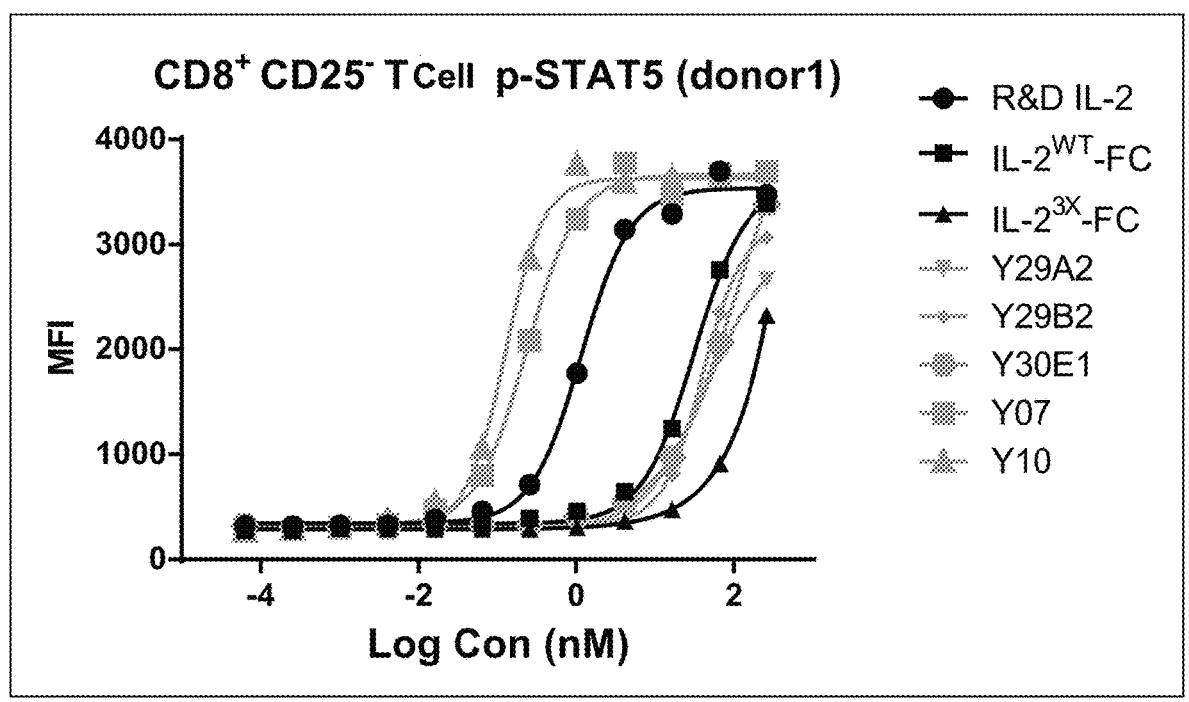
Figure 5C:
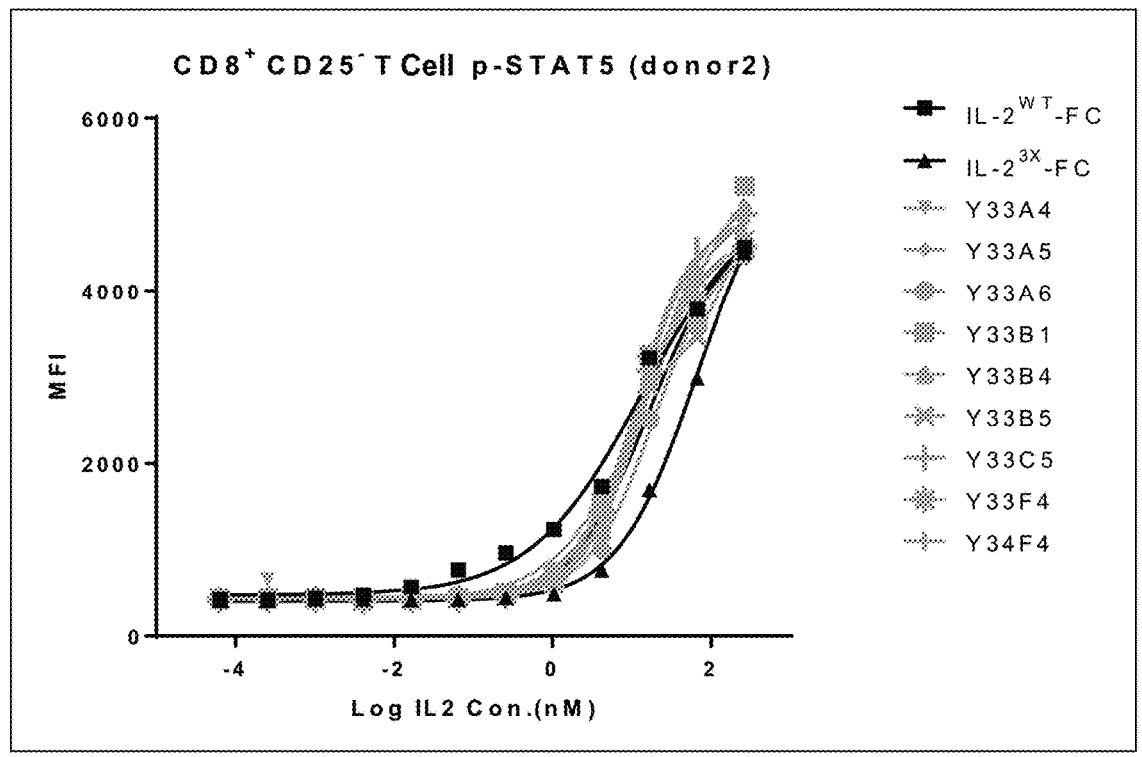
Figure 5D:
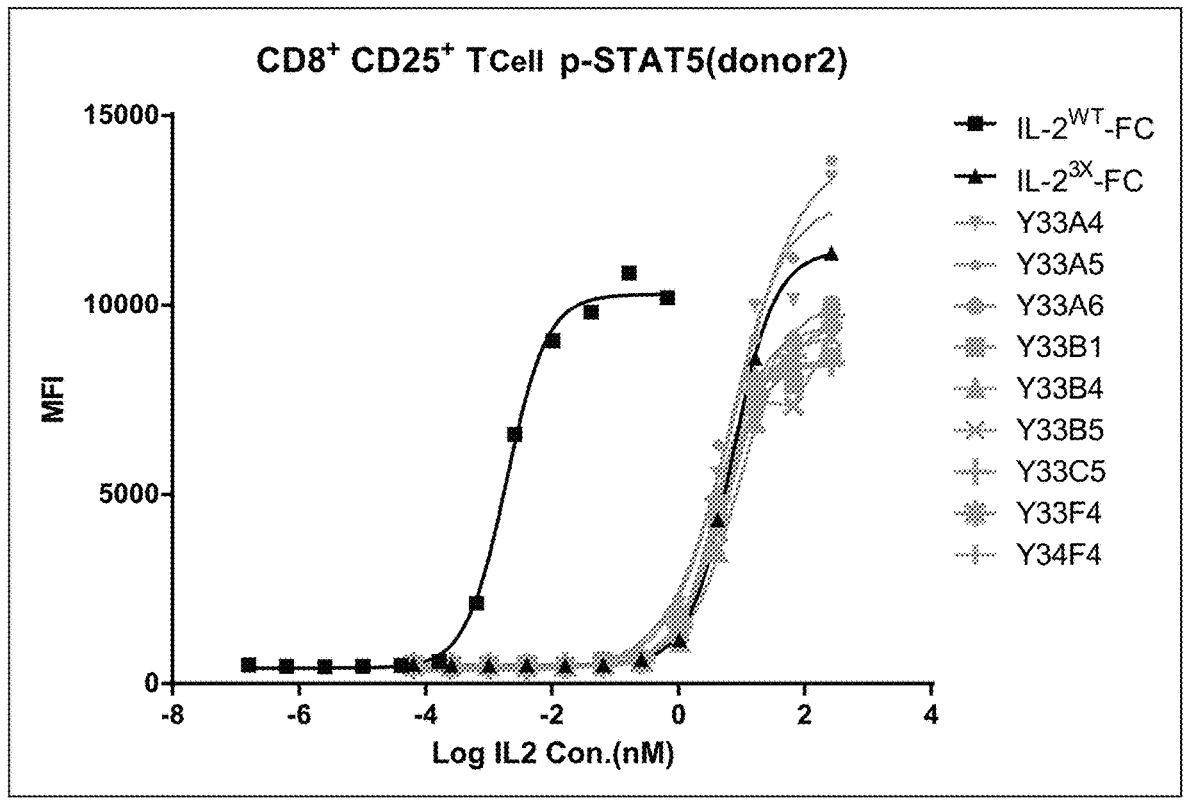

5. Detecting the $EC_{50}$ value of each IL-$2^{mutant}$-FC in activating p-STAT5 signals in CD8$^+$ CD25$^-$ T cells:
   a) CD8$^+$ CD25$^-$ T cells were added to 96-well U-bottom plates (Costar, Catalog No. CLS3799-50EA) at 1×10$^5$ cells per well;
   b) the IL-$2^{mutant}$-FC, the commercialized IL-2 (R&D, Catalog No. 202-IL-500), the IL-$2^{WT}$-FC, and the IL-$2^{3X}$-FC, each of 100 µL, were added and 4-fold diluted in gradient from a maximum concentration of 266.7 nM, for a total of 12 dilution gradients, and the cells were incubated in a 37° C. incubator for 20 min;
   c) 55.5 µL of 4.2% formaldehyde solution was added to immobilize the above cells at room temperature for 10 min;
   d) centrifugation was performed to discard the supernatant, and 200 µL of ice methanol (Fisher, Catalog No. A452-4) was added to resuspend the cells, which were then incubated in a 4° C. refrigerator for 30 min;
   e) centrifugation was performed to discard the supernatant, and the residue was washed 3 times with 200 µL of staining buffer (BD, Catalog No. 554657);
   f) 200 µL of permeabilization/fixation buffer (BD, Catalog No. 51-2091KZ) containing anti-p-STAT5-AlexFlour647 (BD, Catalog No. 562076, 1:200 dilution) was added, and the cells were incubated away from light for 3 h at room temperature;
   g) the cells were washed with staining buffer for three times, resuspended with 100 µL of staining buffer, and detected using a flow cytometer;
   h) curves were plotted with the antibody concentration as the abscissa and the mean fluorescence intensity of AlexFlour647 as the ordinate to give the $EC_{50}$ value of p-STAT5 signal. The results are shown in FIG. 5A and FIG. 5C.
6. Detecting the $EC_{50}$ value of each IL-$2^{mutant}$-FC in activating p-STAT5 signals in CD8$^+$ CD25$^+$ T cells:
   a) CD8$^+$ CD25$^+$ T cells were added to 96-well U-bottom plates at 1×10$^5$ cells per well;
   b) the $EC_{50}$ value and curve of the p-STAT5 signal were obtained as per b)-h) in step 5, and the results are shown in FIG. 5B and FIG. 5D.

According to the results, by comparing the ratio of the activation effect of IL-$2^{mutant}$-FC fusion protein on CD8$^+$ CD25+ T cells to the activation effect of IL-$2^{mutant}$-FC fusion protein on CD8+CD25$^-$ T cells (as shown in Table 6.1 and Table 6.2), it can be seen that: 1) the activation effect of each IL-$2^{mutant}$-FC fusion protein described herein on CD8$^+$ CD25$^-$ T cells was better than that of IL-$2^{3X}$-FC fusion protein, and relatively close to that of IL-$2^{WT}$-FC fusion protein, wherein the effects of Y07 and Y10 were even stronger than that of commercial IL-2; 2) when the expression of CD25 was stimulated, the activation effect of each IL-$2^{mutant}$-FC fusion protein described herein on CD8$^+$ CD25$^+$ T cells was slightly stronger than that on CD25$^-$ T cells, but significantly different from the substantially enhanced effect of commercial IL-2 and IL-$2^{WT}$-FC fusion protein. In conclusion, according to ratio of the CD25$^+$ $EC_{50}$/CD25$^-$ $EC_{50}$, it was obvious that each IL-2 mutant described herein effectively eliminated the activation preference for CD25$^+$ cells, and the activation effect of Y07 and Y10 on CD25$^-$ cells was better than that of other mutations.

TABLE 6.1

$EC_{50}$ of IL-$2^{mutant}$-FC fusion protein in activating p-STAT5 signals in CD25$^{+/-}$ T cells and ratio thereof (donor1)

| Donor1 | R&D IL-2 | IL-$2^{WT}$-FC | IL-$2^{3X}$-FC | Y29A2 | Y29B2 | Y30E1 | Y07 | Y10 |
|---|---|---|---|---|---|---|---|---|
| CD25$^-$ pSTAT5 $EC_{50}$ | 1.2 | 31.7 | Poor Fit | 46.1 | 40.5 | 105.7 | 0.2 | 0.2 |
| CD25$^+$ pSTAT5 $EC_{50}$ | 0.0007 | 0.0075 | 5.6 | 2.9 | 8.0 | 8.3 | 0.1 | 0.1 |
| Ratio of CD25$^-$ $EC_{50}$/CD25$^+$ $EC_{50}$ | 1624 | 4244 | NA | 16 | 5 | 13 | 2 | 2 |

TABLE 6.2

$EC_{50}$ of IL-$2^{mutant}$-FC fusion protein in activating p-STAT5 signals in CD25$^{+/-}$ T cells and ratio thereof (donor2)

| Donor2 | IL-$2^{WT}$-FC | IL-$2^{3X}$-FC | Y33A4 | Y33A5 | Y33A6 | Y33B1 | Y33B4 | Y33B5 | Y33C5 | Y33F4 | Y34F4 |
|---|---|---|---|---|---|---|---|---|---|---|---|
| CD25$^-$ pSTAT5 $EC_{50}$ | 13 | 64 | 11.6 | 13.8 | 18.9 | 21.6 | 15.6 | 16.1 | 11.4 | 10.7 | 10.8 |
| CD25$^+$ pSTAT5 $EC_{50}$ | 0.002 | 7.1 | 6.1 | 7.8 | 6.8 | 3.6 | 8.0 | 4.9 | 3.7 | 4.9 | 5.0 |
| Ratio of CD25$^-$ $EC_{50}$/CD25$^+$ $EC_{50}$ | 6500 | 9 | 2 | 2 | 3 | 6 | 2 | 3 | 3 | 2 | 2 |

SEQUENCE LISTING

IL-2$^{WT}$ (SEQ ID NO: 1) with Mutation (C125S)

APTSSSTKKTQLQLEHLLLDLQMILNGINNYKNPKLTRMLTFKFYMPKK
ATELKHLQCLEEELKPLEEVLNLAQSKNFHLRPRDLISNINVIVLELKG
SETTFMCEYADETATIVEFLNRWITFSQSIISTLT

IL-2$^{3X}$ (SEQ ID NO: 2) with Mutations (C125S, R38D, K43E, E61R)

APTSSSTKKTQLQLEHLLLDLQMILNGINNYKNPKLTDMLTFEFYMPKK
ATELKHLQCLERELKPLEEVLNLAQSKNFHLRPRDLISNINVIVLELKG
SETTFMCEYADETATIVEFLNRWITFSQSIISTLT

IL-2$^{H9}$ (SEQ ID NO: 3) with Mutations (C125S, L80F, R81D, L85V, I86V, I92F)

APTSSSTKKTQLQLEHLLLDLQMILNGINNYKNPKLTRMLTFKFYMPKK
ATELKHLQCLEEELKPLEEVLNLAQSKNFHFDPRDVVSNINVFVLELKG
SETTFMCEYADETATIVEFLNRWITFSQSIISTLT

Yeast Surface Display Plasmid pYDC011 (SEQ ID NO: 4)

ACGGATTAGAAGCCGCCGAGCGGGTGACAGCCCTCCGAAGGAAGACTCT
CCTCCGTGCGTCCTCGTCTTCACCGGTCGCGTTCCTGAAACGCAGATGT
GCCTCGCGCCGCACTGCTCCGAACAATAAAGATTCTACAATACTAGCTT
TTATGGTTATGAAGAGGAAAAATTGGCAGTAACCTGGCCCCACAAACCT
TCAAATGAACGAATCAAATTAACAACCATAGGATGATAATGCGATTAGT
TTTTTAGCCTTATTTCTGGGGTAATTAATCAGCGAAGCGATGATTTTTG
ATCTATTAACAGATATATAAATGCAAAAACTGCATAACCACTTTAACTA
ATACTTTCAACATTTTCGGTTTGTATTACTTCTTATTCAAATGTAATAA
AAGTATCAACAAAAAATTGTTAATATACCTCTATACTTTAACGTCAAGG
AGAAAAAACCCCGGATCGGACTACTAGCAGCTGTAATACGACTCACTAT
AGGGAATATTAAGCTAATTCCCTACTTCATACATTTTCAATTAAGATGC
AGTTACTTCGCTGTTTTTCAATATTTTCTGTTATTGCTTCAGTTTTAGC
AGGaTCctgacatagtagggattataaGGaGGcGGtGGaTCcGATTACA
AGGATGACGATGACAAGGGCGGAGGAGGCTCcCAGGAACTGACAACTAT
ATGCGAGCAAATCCCCTCACCAACTTTAGAATCGACGCCGTACTCTTTG
TCAACGACTACTATTTTGGCCAACGGGAAGGCAATGCAAGGAGTTTTTG
AATATTACAAATCAGTAACGTTTGTCAGTAATTGCGGTTCTCACCCCTC
AACgACTAGCAAAGGCAGCCCCATAAACACACAGTATGTTTTTtaaTGA
GTTTAAACCCGCTGATCTGATAACAACAGTGTAGATGTAACAAAATCGA
CTTTGTTCCCACTGTACTTTTAGCTCGTACAAAATACAATATACTTTTC
ATTTCTCCGTAAACAACATGTTTTCCCATGTAATATCCTTTTCTATTTT
TCGTTCCGTTACCAACTTTACACATACTTTATATAGCTATTCACTTCTA
TACACTAAAAAACTAAGACAATTTTAATTTTGCTGCCTGCCATATTTCA
ATTTGTTATAAATTCCTATAATTTATCCTATTAGTAGCTAAAAAAAGAT
GAATGTGAATCGAATCCTAAGAGAATTGGGCAAGTGCACAAACAATACT
TAAATAAATACTACTCAGTAATAACCTATTTCTTAGCATTTTTGACGAA
ATTTGCTATTTTGTTAGAGTCTTTTACACCATTTGTCTCCACACCTCCG
CTTACATCAACACCAATAACGCCATTTAATCTAAGCGCATCACCAACAT
TTTCTGGCGTCAGTCCACCAGCTAACATAAAATGTAAGCTCTCGGGGCT
CTCTTGCCTTCCAACCCAGTCAGAAATCGAGTTCCAATCCAAAAGTTCA
CCTGTCCCACCTGCTTCTGAATCAAACAAGGGAATAAACGAATGAGGTT
TCTGTGAAGCTGCACTGAGTAGTATGTTGCAGTCTTTTGGAAATACGAG
TCTTTTAATAACTGGCAAACCGAGGAACTCTTGGTATTCTTGCCACGAC
TCATCTCCGTGCAGTTGGACGATATCAATGCCGTAATCATTGACCAGAG
CCAAAACATCCTCCTTAGGTTGATTACGAAACACGCCAACCAAGTATTT
CGGAGTGCCTGAACTATTTTTATATGCTTTTACAAGACTTGAAATTTTC
CTTGCAATAACCGGGTCAATTGTTCTCTTTCTATTGGGCACACATATAA
TACCCAGCAAGTCAGCATCGGAATCTAGAGCACATTCTGCGGCCTCTGT
GCTCTGCAAGCCGCAAACTTTCACCAATGGACCAGAACTACCTGTGAAA
TTAATAACAGACATACTCCAAGCTGCCTTTGTGTGCTTAATCACGTATA
CTCACGTGCTCAATAGTCACCAATGCCCTCCCTCTTGGCCCTCTCCTTT
TCTTTTTTCGACCGAATTTCTTGAAGACGAAAGGGCCTCGTGATACGCC
TATTTTATAGGTTAATGTCATGATAATAATGGTTTCTTAGGACGGATC
GCTTGCCTGTAACTTACACGCGCCTCGTATCTTTTAATGATGGAATAAT
TTGGGAATTTACTCTGTGTTTATTTATTTTTATGTTTTGTATTTGGATT
TTAGAAAGTAAATAAAGAAGGTAGAAGAGTTACGGAATGAAGAAAAAAA
AATAAACAAAGGTTTAAAAAATTTCAACAAAAAGCGTACTTTACATATA
TATTTATTAGACAAGAAAAGCAGATTAAATAGATATACATTCGATTAAC
GATAAGTAAAATGTAAAATCACAGGATTTTCGTGTGTGGTCTTCTACAC
AGACAAGATGAAACAATTCGGCATTAATACCTGAGAGCAGGAAGAGCAA
GATAAAAGGTAGTATTTGTTGGCGATCCCCCTAGAGTCTTTTACATCTT
CGGAAAACAAAACTATTTTTTCTTTAATTTCTTTTTTTACTTTCTATT
TTTAATTTATATATTTATATTAAAAAATTTAAATTATAATTATTTTTAT
AGCACGTGATGAAAAGGACCCAGGTGGCACTTTTCGGGGAAATGTGCGC
GGAACCCCTATTTGTTTATTTTTCTAAATACATTCAAATATGTATCCGC
TCATGAGACAATAACCCTGATAAATGCTTCAATAATATTGAAAAGGAA
GAGTATGAGTATTCAACATTTCCGTGTCGCCCTTATTCCCTTTTTTGCG
GCATTTTGCCTTCCTGTTTTTGCTCACCCAGAAACGCTGGTGAAAGTAA
AAGATGCTGAAGATCAGTTGGGTGCACGAGTGGGTTACATCGAACTGGA
TCTCAACAGCGGTAAGATCCTTGAGAGTTTTCGCCCCGAAGAACGTTTT
CCAATGATGAGCACTTTTAAAGTTCTGCTATGTGGCGCGGTATTATCCC
GTGTTGACGCCGGGCAAGAGCAACTCGGTCGCCGCATACACTATTCTCA
GAATGACTTGGTTGAGTACTCACCAGTCACAGAAAAGCATCTTACGGAT

```
GGCATGACAGTAAGAGAATTATGCAGTGCTGCCATAACCATGAGTGATA

ACACTGCGGCCAACTTACTTCTGACAACGATCGGAGGACCGAAGGAGCT

AACCGCTTTTTTGCACAACATGGGGGATCATGTAACTCGCCTTGATCGT

TGGGAACCGGAGCTGAATGAAGCCATACCAAACGACGAGCGTGACACCA

CGATGCCTGTAGCAATGGCAACAACGTTGCGCAAACTATTAACTGGCGA

ACTACTTACTCTAGCTTCCCGGCAACAATTAATAGACTGGATGGAGGCG

GATAAAGTTGCAGGACCACTTCTGCGCTCGGCCCTTCCGGCTGGCTGGT

TTATTGCTGATAAATCTGGAGCCGGTGAGCGTGGGTCTCGCGGTATCAT

TGCAGCACTGGGGCCAGATGGTAAGCCCTCCCGTATCGTAGTTATCTAC

ACGACGGGCAGTCAGGCAACTATGGATGAACGAAATAGACAGATCGCTG

AGATAGGTGCCTCACTGATTAAGCATTGGTAACTGTCAGACCAAGTTTA

CTCATATATACTTTAGATTGATTTAAAACTTCATTTTTAATTTAAAAGG

ATCTAGGTGAAGATCCTTTTTGATAATCTCATGACCAAAATCCCTTAAC

GTGAGTTTTCGTTCCACTGAGCGTCAGACCCCGTAGAAAAGATCAAAGG

ATCTTCTTGAGATCCTTTTTTTCTGCGCGTAATCTGCTGCTTGCAAACA

AAAAAACCACCGCTACCAGCGGTGGTTTGTTTGCCGGATCAAGAGCTAC

CAACTCTTTTTCCGAAGGTAACTGGCTTCAGCAGAGCGCAGATACCAAA

TACTGTCCTTCTAGTGTAGCCGTAGTTAGGCCACCACTTCAAGAACTCT

GTAGCACCGCCTACATACCTCGCTCTGCTAATCCTGTTACCAGTGGCTG

CTGCCAGTGGCGATAAGTCGTGTCTTACCGGGTTGGACTCAAGACGATA

GTTACCGGATAAGGCGCAGCGGTCGGGCTGAACGGGGGGTTCGTGCACA

CAGCCCAGCTTGGAGCGAACGACCTACACCGAACTGAGATACCTACAGC

GTGAGCATTGAGAAAGCGCCACGCTTCCCGAAGGGAGAAAGGCGGACAG

GTATCCGGTAAGCGGCAGGGTCGGAACAGGAGAGCGCACGAGGGAGCTT

CCAGGGGGAACGCCTGGTATCTTTATAGTCCTGTCGGGTTTCGCCACC

TCTGACTTGAGCGTCGATTTTTGTGATGCTCGTCAGGGGGGCCGAGCCT

ATGGAAAAACGCCAGCAACGCGGCCTTTTTACGGTTCCTGGCCTTTTGC

TGGCCTTTTGCTCACATGTTCTTTCCTGCGTTATCCCCTGATTCTGTGG

ATAACCGTATTACCGCCTTTGAGTGAGCTGATACCGCTCGCCGCAGCCG

AACGACCGAGCGCAGCGAGTCAGTGAGCGAGGAAGCGGAAGAGCGCCCA

ATACGCAAACCGCCTCTCCCCGCGCGTTGGCCGATTCATTAATGCAGCT

GGCACGACAGGTTTCCCGACTGGAAAGCGGGCAGTGAGCGCAACGCAAT

TAATGTGAGTTACCTCACTCATTAGGCACCCCAGGCTTTACACTTTATG

CTTCCGGCTCCTATGTTGTGTGGAATTGTGAGCGGATAACAATTTCACA

CAGGAAACAGCTATGACCATGATTACGCCAAGCTCGGAATTAACCCTCA

CTAAAGGGAACAAAAGCTGGCTAGT
```

Primer Sequence:

AMP0191:                                   (SEQ ID NO: 5)
cccggatcggactactagcagc AMP0199:                                   (SEQ ID NO: 6)
CTCCTTGCATTGCCTTCCCGTTG AMP0210:                                   (SEQ ID NO: 7)
GTTATTGCTTCAGTTTTAGCAGCTCCCACCAGCAGCAGCACC AMP0211:                                   (SEQ ID NO: 8)
CATCGTCATCCTTGTAATCgGAtCCaCCgCCtCCGGTCAGTGTGCTGAT
GATGC

AMP0224:                                   (SEQ ID NO: 9)
CTGGGTCTTCTTGGTGCTGC

AMP0225:                                   (SEQ ID NO: 10)
GAAGTTCTTGCTCTGGGCTAAATTG

IL-2 Receptor Sequence:
IL-2Rα Receptor (SEQ ID NO: 11), C-Terminal with an Avi Tag and a His6 Tag

ELCDDDPPEIPHATFKAMAYKEGTMLNCECKRGFRRIKSGSLYMLCTGN

SSHSSWDNQCQCTSSATRNTTKQVTPQPEEQKERKTTEMQSPMQPVDQA

SLPGHCREPPPWENEATERIYHFVVGQMVYYQCVQGYRALHRGPAESVC

KMTHGKTRWTQPQLICTGEMETSQFPGEEKPQASPEGRPESETSCLVTT

<u>GLNDIFEAQKIEWHEHHHHHH</u>

IL-2RB Receptor (SEQ ID NO: 12), C-Terminal with an Avi Tag and a His6 Tag

AVNGTSQFTCFYNSRANISCVWSQDGALQDTSCQVHAWPDRRRWNQTCE

LLPVSQASWACNLILGAPDSQKLTTVDIVTLRVLCREGVRWRVMAIQDF

KPFENLRLMAPISLQVVHVETHRCNISWEISQASHYFERHLEFEARTLS

PGHTWEEAPLLTLKQKQEWICLETLTPDTQYEFQVRVKPLQGEFTTWSP

WSQPLAFRTKPAALGKDT<u>GLNDIFEAQKIEWHEHHHHHH</u>

Vector pYDO_017: (SEQ ID NO: 13)

```
gacggatcgggagatctcccgatcccctatggtgcactctcagtacaat ctgctctgatgccgcatagttaagccagtatctgctccctgcttgtgtg ttggaggtcgctgagtagtgcgcgagcaaaatttaagctacaacaaggc aaggcttgaccgacaattgcatgaagaatctgcttagggttaggcgttt tgcgctgcttcgcgatgtacgggccagatatacgcgttgacattgatta ttgactagttattaatagtaatcaattacggggtcattagttcatagcc catatatggagttccgcgttacataacttacggtaaatggcccgcctgg ctgaccgcccaacgacccccgcccattgacgtcaataatgacgtatgtt cccatagtaacgccaatagggactttccattgacgtcaatgggtggagt atttacggtaaactgcccacttggcagtacatcaagtgtatcatatgcc aagtacgccccctattgacgtcaatgacggtaaatggcccgcctggcat tatgcccagtacatgaccttatgggactttcctacttggcagtacatct acgtattagtcatcgctattaccatggtgatgcggttttggcagtacat
```

-continued caatgggcgtggatagcggtttgactcacggggatttccaagtctccac
cccattgacgtcaatgggagtttgttttggcaccaaaatcaacgggact
ttccaaaatgtcgtaacaactccgccccattgacgcaaatgggcggtag
gcgtgtacggtgggaggtctatataagcagagctctctggctaactaga
gaacccactgcttactggcttatcgaaattaatacgactcactataggg
agacccaagctggatggagaccgacaccctcttactgtgggctgctg
ctgtgggttcccggttccactggATCctgacatagtagggattataaGG
aGGcGGtGGaTCcggcggcggaggctccgacaaaacccatacatgtcct
ccttgccccgccctgaggctgctggaggcccagcgtgttcctgtttc
ccccaagcccaaagataccctcatgatctccaggaccccgaagtgac
ctgcgtcgtggtcgacgtgagccacgaggaccctgaagtcaagttcaac
tggtacgtcgatggcgtggaggtgcacaacgctaagaccaaaccccggg
aagagcagtacaattccacctacagggtggtgtccgtcctgacagtgct
gcaccaagactggctgaatggaaaggagtacaagtgcaaagtgagcaat
aaggccctccctgctcccattgagaagaccatttccaaggccaaaggcc
agcctcgggaacccaggtgtacacactgccccttccagggaggagat
gaccaagaaccaggtgagcctcacctgcctggtgaagggcttctaccct
agcgacattgctgtgagtgggagagcaacggccagcccgaaaacaact
ataagacaacccctcccgtgctggacagcgacggctccttctttctgta
ctccaagctcaccgtggacaagtccaggtggcaacagggaaacgtgttc
tcctgctccgtgatgcacgaggcctccacaaccactacacccagaaga
gcctgagcctgtcccctggcaagtgatgaagcggccgctcgagtctaga
gggcccgtttaaacccgctgatcagcctcgactgtgccttctagttgcc
agccatctgttgtttgcccctcccccgtgccttccttgaccctggaagg
tgccactcccactgtccttttcctaataaaatgaggaaattgcatcgcat
tgtctgagtaggtgtcattctattctggggggtgggggggcaggacag
caaggggaggattgggaagacaatagcaggcatgctggggatgcggtg
ggctctatggcttctgaggcggaaagaaccagctggggctctagggggt
atccccacgcgccctgtagcggcgcattaagcgcggcgggtgtggtggt
tacgcgcagcgtgaccgctacacttgccagcgccctagcgcccgctcct
ttcgctttcttcccttcctttctcgccacgttcgccggctttccccgtc
aagctctaaatcgggggctccctttagggttccgatttagtgctttacg
gcacctcgaccccaaaaaacttgattagggtgatggttcacgtagtggg
ccatcgccctgatagacggtttttcgccctttgacgttggagtccacgt
tctttaatagtggactcttgttccaaactggaacaacactcaaccctat
ctcggtctattcttttgatttataagggattttgccgatttcggcctat
tggttaaaaaatgagctgatttaacaaaaatttaacgcgaattaattct
gtggaatgtgtgtcagttagggtgtggaaagtccccaggctccccagca
ggcagaagtatgcaaagcatgcatctcaattagtcagcaaccaggtgtg
gaaagtccccaggctccccagcaggcagaagtatgcaaagcatgcatct -continued caattagtcagcaaccatagtcccgcccctaactccgcccatcccgccc
ctaactccgccagttccgccattctccgcccatggctgactaattt
tttttatttatgcagaggccgaggccgcctctgcctctgagctattcca
gaagtagtgaggaggcttttttggaggcctaggcttttgcaaaaagctc
ccgggagcttgtatatccatttcggatctgatcaagagacaggatgag
gatcgtttcgcatgattgaacaagatggattgcacgcaggttctccggc
cgcttgggtggagaggctattcggctatgactgggcacaacagacaatc
ggctgctctgatgccgccgtgttccggctgtcagcgcaggggcgcccgg
ttcttttgtcaagaccgacctgtccggtgccctgaatgaactgcagga
cgaggcagcgcggctatcgtggctggccacgacgggcgttccttgcgca
gctgtgctcgacgttgtcactgaagcgggaagggactggctgctattgg
gcgaagtgccggggcaggatctcctgtcatctcaccttgctcctgccga
gaaagtatccatcatggctgatgcaatgcggcggctgcatacgcttgat
ccggctacctgcccattcgaccaccaagcgaaacatcgcatcgagcgag
cacgtactcggatggaagccggtcttgtcgatcaggatgatctggacga
agagcatcaggggctcgcgccagccgaactgttcgccaggctcaaggcg
cgcatgcccgacggcgaggatctcgtcgtgacccatggcgatgcctgct
tgccgaatatcatggtggaaaatggccgcttttctggattcatcgactg
tggccggctgggtgtggcggaccgctatcaggacatagcgttggctacc
cgtgatattgctgaagagcttggcggcgaatgggctgaccgcttcctcg
tgctttacggtatcgccgctcccgattcgcagcgcatcgccttctatcg
ccttcttgacgagttcttctgagcgggactctggggttcgaaatgaccg
accaagcgacgcccaacctgccatcacgagatttcgattccaccgccgc
cttctatgaaaggttgggcttcggaatcgttttccgggacgccggctgg
atgatcctccagcgcggggatctcatgctggagttcttcgcccaccca
acttgtttattgcagcttataatggttacaaataaagcaatagcatcac
aaatttcacaaataaagcatttttttcactgcattctagttgtggttg
tccaaactcatcaatgtatcttatcatgtctgtataccgtcgacctcta
gctagagcttggcgtaatcatggtcatagctgtttcctgtgtgaaattg
ttatccgctcacaattccacacaacatacgagccggaagcataaagtgt
aaagcctggggtgcctaatgagtgagctaactcacattaattgcgttgc
gctcactgcccgctttccagtcgggaaacctgtcgtgccagctgcatta
atgaatcggccaacgcgcggggagaggcggtttgcgtattgggcgctct
tccgcttcctcgctcactgactcgctgcgctcggtcgttcggctgcggc
gagcggtatcagctcactcaaaggcggtaatacggttatccacagaatc
aggggataacgcaggaaagaacatgtgagcaaaaggccagcaaaaggcc
aggaaccgtaaaaaggccgcgttgctggcgtttttccataggctccgcc
cccctgacgagcatcacaaaaatcgacgctcaagtcagaggtggcgaaa
cccgacaggactataaagataccaggcgtttccccctggaagctccctc
gtgcgctctcctgttccgaccctgccgcttaccggatacctgtccgcct
ttctcccttcgggaagcgtggcgctttctcatagctcacgctgtaggta

```
tctcagttcggtgtaggtcgttcgctccaagctgggctgtgtgcacgaa
cccccgttcagcccgaccgctgcgccttatccggtaactatcgtcttg
agtccaacccggtaagacacgacttatcgccactggcagcagccactgg
taacaggattagcagagcgaggtatgtaggcggtgctacagagttcttg
aagtggtggcctaactacggctacactagaagaacagtatttggtatct
gcgctctgctgaagccagttaccttcggaaaaagagttggtagctcttg
atccggcaaacaaaccaccgctggtagcggtttttttgtttgcaagcag
cagattacgcgcagaaaaaaggatctcaagaagatcctttgatctttt
ctacggggtctgacgctcagtggaacgaaaactcacgttaagggatttt
ggtcatgagattatcaaaaaggatcttcacctagatccttttaaattaa
aaatgaagttttaaatcaatctaaagtatatatgagtaaacttggtctg
acagttaccaatgcttaatcagtgaggcacctatctcagcgatctgtct
atttcgttcatccatagttgcctgactccccgtcgtgtagataactacg
atacgggagggcttaccatctggccccagtgctgcaatgataccgcgag
acccacgctcaccggctccagatttatcagcaataaaccagccagccgg
aagggccgagcgcagaagtggtcctgcaactttatccgcctccatccag
```

```
tctattaattgttgccgggaagctagagtaagtagttcgccagttaata
gtttgcgcaacgttgttgccattgctacaggcatcgtggtgtcacgctc
gtcgtttggtatggcttcattcagctccggttcccaacgatcaaggcga
gttacatgatccccatgttgtgcaaaaaagcggttagctccttcggtc
ctccgatcgttgtcagaagtaagttggccgcagtgttatcactcatggt
tatggcagcactgcataattctcttactgtcatgccatccgtaagatgc
ttttctgtgactggtgagtactcaaccaagtcattctgagaatagtgta
tgcggcgaccgagttgctcttgcccggcgtcaatacgggataataccgc
gccacatagcagaactttaaaagtgctcatcattggaaaacgttcttcg
gggcgaaaactctcaaggatcttaccgctgttgagatccagttcgatgt
aacccactcgtgcacccaactgatcttcagcatcttttactttcaccag
cgtttctgggtgagcaaaaacaggaaggcaaaatgccgcaaaaaaggga
ataagggcgacacggaaatgttgaatactcatactcttcctttttcaat
attattgaagcatttatcagggttattgtctcatgagcggatacatatt
tgaatgtatttagaaaaataaacaatagggggttccgcgcacatttccc
cgaaaagtgccacctgacgtc
```

---

The invention claimed is:

1. An IL-2 mutant protein, comprising at least one mutation compared with a wild-type IL-2 comprising the amino acid sequence of SEQ ID NO:1, wherein the mutant protein has an eliminated or reduced binding affinity for an IL-2Rα receptor and/or an enhanced binding affinity for an IL-2Rß receptor, wherein the IL-2 mutant protein comprises mutations of K35/T37E/R38/F42 at positions corresponding to positions in SEQ ID NO: 1.

2. The IL-2 mutant protein of claim 1, wherein the IL-2 mutant protein comprises a combinatorial mutation of
K35E/T37E/R38E/F42A
wherein the IL-2 mutant protein has a reduced or eliminated binding affinity for IL-2Rα receptor relative to wild IL-2 protein.

3. The IL-2 mutant protein of claim 1, wherein the IL-2 mutant protein has an amino acid residue S at position 125.

4. The IL-2 mutant protein of claim 1, wherein, when expressed in a fusion to an Fc antibody fragment in a mammalian cell, the IL-2 mutant protein reaches a purity of higher than 70%, 80%, or 90% after being purified by one-step protein A affinity chromatography, as detected by a SEC-HPLC.

5. A fusion protein comprising the IL2 mutant protein of claim 1.

6. The fusion protein of claim 5, wherein the IL-2 mutant protein is fused to an Fc antibody fragment.

7. An immunoconjugate comprising the IL-2 mutant protein of claim 1 and an antigen-binding molecule.

8. An isolated polynucleotide, encoding the IL-2 mutant protein of claim 1 or a fusion of the IL-2 mutant protein.

9. An expression vector, comprising the polynucleotide of claim 8.

10. A host cell, comprising the polynucleotide of claim 8.

11. A method for producing an IL-2 mutant protein or a fusion thereof, comprising culturing the host cell of claim 10 under a condition suitable for expressing the IL-2 mutant protein or the fusion thereof.

12. A pharmaceutical composition, comprising the IL-2 mutant protein of claim 1 or a fusion thereof, and a pharmaceutically acceptable carrier.

* * * * *

SEQUENCE LISTING

<160> NUMBER OF SEQ ID NOS: 13

<210> SEQ ID NO 1
<211> LENGTH: 133
<212> TYPE: PRT
<213> ORGANISM: artificial sequence
<220> FEATURE:
<223> OTHER INFORMATION: IL-2WT with mutations(C125S)

<400> SEQUENCE: 1

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 2
<211> LENGTH: 133
<212> TYPE: PRT

```
<213> ORGANISM: artificial sequence
<220> FEATURE:
<223> OTHER INFORMATION: IL-2 3X with mutations(C125S,R38D, K43E, E61R)

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Asp Met Leu Thr Phe Glu Phe Tyr Met Pro Lys
        35                  40                  45

Lys Ala Thr Glu Leu Lys His Leu Gln Cys Leu Glu Arg Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 3
<211> LENGTH: 133
<212> TYPE: PRT
<213> ORGANISM: artificial sequence
<220> FEATURE:
<223> OTHER INFORMATION: IL-2H9 with mutations(C125S,L80F,R81D,L85V,
      I86V, I92F)

<400> SEQUENCE: 3

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 4
<211> LENGTH: 4827
<212> TYPE: DNA
<213> ORGANISM: artificial sequence
<220> FEATURE:
<223> OTHER INFORMATION: yeast display plasmid pYDC011
```

```
<400> SEQUENCE: 4
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240 ttagttttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc cctacttcat acattttcaa ttaagatgca     540
gttacttcgc tgttttttcaa tattttctgt tattgcttca gttttagcag gatcctgaca     600
tagtagggat tataaggagg cggtggatcc gattacaagg atgacgatga caagggcgga     660
ggaggctccc aggaactgac aactatatgc gagcaaatcc cctcaccaac tttagaatcg     720
acgccgtact ctttgtcaac gactactatt ttggccaacg ggaaggcaat gcaaggagtt     780
tttgaatatt acaaatcagt aacgtttgtc agtaattgcg gttctcaccc ctcaacgact     840
agcaaaggca gccccataaa cacacagtat gttttttaat gagtttaaac ccgctgatct     900
gataacaaca gtgtagatgt aacaaaatcg actttgttcc cactgtactt ttagctcgta     960
caaaatacaa tatacttttc atttctccgt aaacaacatg ttttcccatg taatatcctt    1020
ttctattttt cgttccgtta ccaactttac acatacttta tatagctatt cacttctata    1080
cactaaaaaa ctaagacaat tttaattttg ctgcctgcca tatttcaatt tgttataaat    1140
tcctataatt tatcctatta gtagctaaaa aaagatgaat gtgaatcgaa tcctaagaga    1200
attgggcaag tgcacaaaca atacttaaat aaatactact cagtaataac ctatttctta    1260
gcatttttga cgaaatttgc tattttgtta gagtctttta caccatttgt ctccacacct    1320
ccgcttacat caacaccaat aacgccattt aatctaagcg catcaccaac attttctggc    1380
gtcagtccac cagctaacat aaaatgtaag ctctcggggc tctcttgcct tccaacccag    1440
tcagaaatcg agttccaatc caaaagttca cctgtcccac ctgcttctga atcaaacaag    1500
ggaataaacg aatgaggttt ctgtgaagct gcactgagta gtatgttgca gtcttttgga    1560
aatacgagtc ttttaataac tggcaaaccg aggaactctt ggtattcttg ccacgactca    1620
tctccgtgca gttggacgat atcaatgccg taatcattga ccagagccaa acatcctcc     1680 ttaggttgat tacgaaacac gccaaccaag tatttcggag tgcctgaact attttttatat   1740 gcttttacaa gacttgaaat tttccttgca ataaccgggt caattgttct ctttctattg    1800
ggcacacata taatacccag caagtcagca tcggaatcta gagcacattc tgcggcctct    1860
gtgctctgca agccgcaaac tttcaccaat ggaccagaac tacctgtgaa attaataaca    1920
gacatactcc aagctgcctt tgtgtgctta atcacgtata ctcacgtgct caatagtcac    1980
caatgccctc cctcttggcc ctctcctttt cttttttcga ccgaatttct tgaagacgaa    2040
agggcctcgt gatacgccta tttttatagg ttaatgtcat gataataatg gtttcttagg    2100
acggatcgct tgcctgtaac ttacacgcgc ctcgtatctt ttaatgatgg aataatttgg    2160
gaatttactc tgtgtttatt tatttttatg ttttgtattt ggattttaga agtaaataa     2220 agaaggtaga agagttacgg aatgaagaaa aaaaataaa caaggtttta aaaaatttca     2280
acaaaaagcg tactttacat atatatttat tagacaagaa aagcagatta aatagatata   2340
```

```
cattcgatta acgataagta aaatgtaaaa tcacaggatt ttcgtgtgtg gtcttctaca    2400
cagacaagat gaaacaattc ggcattaata cctgagagca ggaagagcaa gataaaaggt    2460
agtatttgtt ggcgatcccc ctagagtctt ttacatcttc ggaaaacaaa aactattttt    2520
tctttaattt ctttttttac tttctatttt taatttatat attatatatta aaaaatttaa   2580 attataatta ttttttatagc acgtgatgaa aaggacccag gtggcacttt tcggggaaat   2640
gtgcgcggaa cccctatttg tttattttttc taaatacatt caaatatgta tccgctcatg   2700
agacaataac cctgataaat gcttcaataa tattgaaaaa ggaagagtat gagtattcaa    2760
catttccgtg tcgcccttat tcccttttttt gcggcatttt gccttcctgt ttttgctcac   2820
ccagaaacgc tggtgaaagt aaaagatgct gaagatcagt tgggtgcacg agtgggttac    2880
atcgaactgg atctcaacag cggtaagatc cttgagagtt ttcgccccga gaacgttttt    2940
ccaatgatga gcacttttaa agttctgcta tgtggcgcgg tattatcccg tgttgacgcc    3000
gggcaagagc aactcggtcg ccgcatacac tattctcaga atgacttggt tgagtactca    3060
ccagtcacag aaaagcatct tacggatggc atgacagtaa gagaattatg cagtgctgcc    3120
ataaccatga gtgataacac tgcggccaac ttacttctga caacgatcgg aggaccgaag    3180
gagctaaccg cttttttgca acatggggg gatcatgtaa ctcgccttga tcgttgggaa    3240
ccggagctga atgaagccat accaaacgac gagcgtgaca ccacgatgcc tgtagcaatg    3300
gcaacaacgt tgcgcaaact attaactggc gaactactta ctctagcttc ccggcaacaa    3360
ttaatagact ggatggaggc ggataaagtt gcaggaccac ttctgcgctc ggcccttccg    3420
gctggctggt ttattgctga taaatctgga gccggtgagc gtgggtctcg cggtatcatt    3480
gcagcactgg ggccagatgg taagccctcc cgtatcgtag ttatctacac gacgggcagt    3540
caggcaacta tggatgaacg aaatagacag atcgctgaga taggtgcctc actgattaag    3600
cattggtaac tgtcagacca agtttactca tatatacttt agattgattt aaaacttcat    3660
ttttaattta aaaggatcta ggtgaagatc ctttttgata atctcatgac caaaatccct    3720
taacgtgagt tttcgttcca ctgagcgtca gaccccgtag aaaagatcaa aggatcttct    3780
tgagatcctt ttttttctgcg cgtaatctgc tgcttgcaaa caaaaaaacc accgctacca    3840
gcggtggttt gtttgccgga tcaagagcta ccaactcttt ttccgaaggt aactggcttc    3900
agcagagcgc agataccaaa tactgtcctt ctagtgtagc cgtagttagg ccaccacttc    3960
aagaactctg tagcaccgcc tacatacctc gctctgctaa tcctgttacc agtggctgct    4020
gccagtggcg ataagtcgtg tcttaccggg ttggactcaa gacgatagtt accggataag    4080
gcgcagcggt cgggctgaac ggggggttcg tgcacacagc ccagcttgga gcgaacgacc    4140
tacaccgaac tgagatacct acagcgtgag cattgagaaa gcgccacgct tcccgaaggg    4200
agaaaggcgg acaggtatcc ggtaagcggc agggtcggaa caggagagcg cacgagggag    4260
cttccagggg gaacgcctg gtatctttat agtcctgtcg ggtttcgcca cctctgactt     4320
gagcgtcgat ttttgtgatg ctcgtcaggg gggccgagcc tatggaaaaa cgccagcaac    4380
gcggcctttt tacggttcct ggccttttgc tggccttttg ctcacatgtt ctttcctgcg    4440
ttatcccctg attctgtgga taaccgtatt accgcctttg agtgagctga taccgctcgc    4500
cgcagccgaa cgaccgagcg cagcgagtca gtgagcgagg aagcggaaga gcgcccaata    4560
cgcaaaccgc ctctccccgc gcgttggccg attcattaat gcagctggca cgacaggttt    4620
cccgactgga aagcgggcag tgagcgcaac gcaattaatg tgagttacct cactcattag    4680
```

```
gcaccccagg ctttacactt tatgcttccg gctcctatgt tgtgtggaat tgtgagcgga    4740
taacaatttc acacaggaaa cagctatgac catgattacg ccaagctcgg aattaaccct    4800
cactaaaggg aacaaaagct ggctagt                                        4827
```

```
<210> SEQ ID NO 5
<211> LENGTH: 22
<212> TYPE: DNA
<213> ORGANISM: artificial sequence
<220> FEATURE:
<223> OTHER INFORMATION: primer AMP0191

<400> SEQUENCE: 5
cccggatcgg actactagca gc                                              22

<210> SEQ ID NO 6
<211> LENGTH: 23
<212> TYPE: DNA
<213> ORGANISM: artificial sequence
<220> FEATURE:
<223> OTHER INFORMATION: primer AMP0199

<400> SEQUENCE: 6
ctccttgcat tgccttcccg ttg                                             23

<210> SEQ ID NO 7
<211> LENGTH: 42
<212> TYPE: DNA
<213> ORGANISM: artificial sequence
<220> FEATURE:
<223> OTHER INFORMATION: primer AMP0210

<400> SEQUENCE: 7
gttattgctt cagttttagc agctcccacc agcagcagca cc                        42

<210> SEQ ID NO 8
<211> LENGTH: 54
<212> TYPE: DNA
<213> ORGANISM: artificial sequence
<220> FEATURE:
<223> OTHER INFORMATION: primer AMP0211

<400> SEQUENCE: 8
catcgtcatc cttgtaatcg gatccaccgc ctccggtcag tgtgctgatg atgc           54

<210> SEQ ID NO 9
<211> LENGTH: 20
<212> TYPE: DNA
<213> ORGANISM: artificial sequence
<220> FEATURE:
<223> OTHER INFORMATION: primer AMP0224

<400> SEQUENCE: 9
ctgggtcttc ttggtgctgc                                                 20

<210> SEQ ID NO 10
<211> LENGTH: 25
<212> TYPE: DNA
<213> ORGANISM: artificial sequence
<220> FEATURE:
<223> OTHER INFORMATION: primer AMP0225

<400> SEQUENCE: 10
gaagttcttg ctctgggcta aattg                                           25
```

```
<210> SEQ ID NO 11
<211> LENGTH: 217
<212> TYPE: PRT
<213> ORGANISM: artificial sequence
<220> FEATURE:
<223> OTHER INFORMATION: IL-2R with C-terminal avi tag and His6 tag

<400> SEQUENCE: 11

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Gly Leu Asn Asp Ile Phe Glu Ala Gln Lys Ile Glu
        195                 200                 205

Trp His Glu His His His His His His
    210                 215

<210> SEQ ID NO 12
<211> LENGTH: 235
<212> TYPE: PRT
<213> ORGANISM: artificial sequence
<220> FEATURE:
<223> OTHER INFORMATION: IL-2R with C-terminal avi tag and His6 tag

<400> SEQUENCE: 12

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95
```

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr Gly Leu Asn Asp Ile Phe Glu Ala Gln Lys
    210                 215                 220

Ile Glu Trp His Glu His His His His His
225                 230                 235

<210> SEQ ID NO 13
<211> LENGTH: 6147
<212> TYPE: DNA
<213> ORGANISM: artificial sequence
<220> FEATURE:
<223> OTHER INFORMATION: vector pYDO_017

<400> SEQUENCE: 13

| | | | | | |
|---|---|---|---|---|---|
| gacggatcgg | gagatctccc | gatcccctat | ggtgcactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggag | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggatgga | 900 |
| gaccgacacc | ctcttactgt | gggtgctgct | gctgtgggtt | cccggttcca | ctggatcctg | 960 |
| acatagtagg | gattataagg | aggcggtgga | tccggcggcg | gaggctccga | caaaacccat | 1020 |
| acatgtcctc | cttgccccgc | ccctgaggct | gctggaggcc | ccagcgtgtt | cctgtttccc | 1080 |
| cccaagccca | agatacccct | catgatctcc | aggacccccg | aagtgacctg | cgtcgtggtc | 1140 |
| gacgtgagcc | acgaggaccc | tgaagtcaag | ttcaactggt | acgtcgatgg | cgtggaggtg | 1200 |
| cacaacgcta | agaccaaacc | ccgggaagag | cagtacaatt | ccacctacag | ggtggtgtcc | 1260 |

```
gtcctgacag tgctgcacca agactggctg aatggaaagg agtacaagtg caaagtgagc    1320
aataaggccc tccctgctcc cattgagaag accatttcca aggccaaagg ccagcctcgg    1380 gaacccagg tgtacacact gcccccttcc agggaggaga tgaccaagaa ccaggtgagc     1440
ctcacctgcc tggtgaaggg cttctaccct agcgacattg ctgtggagtg ggagagcaac    1500
ggccagcccg aaaacaacta taagacaacc cctcccgtgc tggacagcga cggctccttc    1560
tttctgtact ccaagctcac cgtggacaag tccaggtggc aacagggaaa cgtgttctcc    1620
tgctccgtga tgcacgaggc cctccacaac cactacaccc agaagagcct gagcctgtcc    1680
cctggcaagt gatgaagcgg ccgctcgagt ctagagggcc cgtttaaacc cgctgatcag    1740
cctcgactgt gccttctagt tgccagccat ctgttgtttg cccctccccc gtgccttcct    1800
tgaccctgga aggtgccact cccactgtcc tttcctaata aaatgaggaa attgcatcgc    1860
attgtctgag taggtgtcat tctattctgg ggggtggggt ggggcaggac agcaaggggg    1920
aggattggga agacaatagc aggcatgctg gggatgcggt gggctctatg gcttctgagg    1980
cggaaagaac cagctggggc tctaggggt atccccacgc gccctgtagc ggcgcattaa     2040
gcgcggcggg tgtggtggtt acgcgcagcg tgaccgctac acttgccagc gccctagcgc    2100
ccgctccttt cgctttcttc ccttcctttc tcgccacgtt cgccggcttt cccgtcaag     2160 ctctaaatcg gggctccct ttagggttcc gatttagtgc tttacggcac ctcgacccca     2220
aaaaacttga ttagggtgat ggttcacgta gtggccatc gccctgatag acggttttc      2280 gccctttgac gttggagtcc acgttcttta atagtggact cttgttccaa actggaacaa    2340
cactcaaccc tatctcggtc tattcttttg atttataagg gattttgccg atttcggcct    2400
attggttaaa aaatgagctg atttaacaaa aatttaacgc gaattaattc tgtggaatgt    2460
gtgtcagtta gggtgtggaa agtccccagg ctccccagca ggcagaagta tgcaaagcat    2520
gcatctcaat tagtcagcaa ccaggtgtgg aaagtcccca ggctcccag caggcagaag     2580 tatgcaaagc atgcatctca attagtcagc aaccatagtc ccgcccctaa ctccgcccat    2640 cccgcccta actccgccca gttccgccca ttctccgccc catggctgac taatttttt      2700 tatttatgca gaggccgagg ccgcctctgc ctctgagcta ttccagaagt agtgaggagg    2760 ctttttttgga ggcctaggct tttgcaaaaa gctcccggga gcttgtatat ccattttcgg   2820
atctgatcaa gagacaggat gaggatcgtt tcgcatgatt gaacaagatg gattgcacgc    2880
aggttctccg gccgcttggg tggagaggct attcggctat gactgggcac aacagacaat    2940
cggctgctct gatgccgccg tgttccggct gtcagcgcag gggcgcccgg ttcttttgt     3000 caagaccgac ctgtccggtg ccctgaatga actgcaggac gaggcagcgc ggctatcgtg    3060
gctggccacg acgggcgttc cttgcgcagc tgtgctcgac gttgtcactg aagcgggaag    3120
ggactggctg ctattgggcg aagtgccggg gcaggatctc ctgtcatctc accttgctcc    3180
tgccgagaaa gtatccatca tggctgatgc aatgcggcgg ctgcatacgc ttgatccggc    3240
tacctgccca ttcgaccacc aagcgaaaca tcgcatcgag cgagcacgta ctcggatgga    3300
agccggtctt gtcgatcagg atgatctgga cgaagagcat caggggctcg cgccagccga    3360
actgttcgcc aggctcaagg cgcgcatgcc cgacggcgag gatctcgtcg tgacccatgg    3420
cgatgcctgc ttgccgaata tcatggtgga aaatggccgc ttttctggat tcatcgactg    3480
tggccggctg ggtgtggcgg accgctatca ggacatagcg ttggctaccc gtgatattgc    3540
tgaagagctt ggcggcgaat gggctgaccg cttcctcgtg ctttacggta tcgccgctcc    3600
cgattcgcag cgcatcgcct tctatcgcct tcttgacgag ttcttctgag cgggactctg    3660
```

```
gggttcgaaa tgaccgacca agcgacgccc aacctgccat cacgagattt cgattccacc    3720
gccgccttct atgaaaggtt gggcttcgga atcgttttcc gggacgccgg ctggatgatc    3780
ctccagcgcg gggatctcat gctggagttc ttcgcccacc ccaacttgtt tattgcagct    3840
tataatggtt acaaataaag caatagcatc acaaatttca caaataaagc attttttca     3900 ctgcattcta gttgtggttt gtccaaactc atcaatgtat cttatcatgt ctgtataccg    3960
tcgacctcta gctagagctt ggcgtaatca tggtcatagc tgtttcctgt gtgaaattgt    4020
tatccgctca caattccaca acatacga gccggaagca taaagtgtaa agcctggggt      4080
gcctaatgag tgagctaact cacattaatt gcgttgcgct cactgcccgc tttccagtcg    4140
ggaaacctgt cgtgccagct gcattaatga atcggccaac gcgcggggag aggcggtttg    4200
cgtattgggc gctcttccgc ttcctcgctc actgactcgc tgcgctcggt cgttcggctg    4260
cggcgagcgg tatcagctca ctcaaaggcg gtaatacggt tatccacaga atcaggggat    4320
aacgcaggaa agaacatgtg agcaaaaggc cagcaaaagg ccaggaaccg taaaaaggcc    4380
gcgttgctgg cgtttttcca taggctccgc cccctgacg agcatcacaa aaatcgacgc     4440
tcaagtcaga ggtggcgaaa cccgacagga ctataaagat accaggcgtt cccccctgga    4500
agctccctcg tgcgctctcc tgttccgacc ctgccgctta ccggatacct gtccgccttt    4560
ctcccttcgg gaagcgtggc gctttctcat agctcacgct gtaggtatct cagttcggtg    4620
taggtcgttc gctccaagct gggctgtgtg cacgaacccc ccgttcagcc cgaccgctgc    4680
gccttatccg gtaactatcg tcttgagtcc aacccggtaa gacacgactt atcgccactg    4740
gcagcagcca ctggtaacag gattagcaga gcgaggtatg taggcggtgc tacagagttc    4800
ttgaagtggt ggcctaacta cggctacact agaagaacag tatttggtat ctgcgctctg    4860
ctgaagccag ttaccttcgg aaaaagagtt ggtagctctt gatccggcaa acaaaccacc    4920
gctggtagcg gtttttttgt ttgcaagcag cagattacgc gcagaaaaaa aggatctcaa    4980
gaagatcctt tgatctttc tacggggtct gacgctcagt ggaacgaaaa ctcacgttaa     5040
gggattttgg tcatgagatt atcaaaaagg atcttcacct agatcctttt aaattaaaaa    5100
tgaagtttta atcaatcta aagtatatat gagtaaactt ggtctgacag ttaccaatgc     5160
ttaatcagtg aggcacctat ctcagcgatc tgtctatttc gttcatccat agttgcctga    5220
ctccccgtcg tgtagataac tacgatacgg gagggcttac catctggccc cagtgctgca    5280
atgataccgc gagacccacg ctcaccggct ccagatttat cagcaataaa ccagccagcc    5340
ggaagggccg agcgcagaag tggtcctgca actttatccg cctccatcca gtctattaat    5400
tgttgccggg aagctagagt aagtagttcg ccagttaata gtttgcgcaa cgttgttgcc    5460
attgctacag gcatcgtggt gtcacgctcg tcgtttggta tggcttcatt cagctccggt    5520
tcccaacgat caaggcgagt tacatgatcc cccatgttgt gcaaaaaagc ggttagctcc    5580
ttcggtcctc cgatcgttgt cagaagtaag ttggccgcag tgttatcact catggttatg    5640
gcagcactgc ataattctct tactgtcatg ccatccgtaa gatgcttttc tgtgactggt    5700
gagtactcaa ccaagtcatt ctgagaatag tgtatgcggc gaccgagttg ctcttgcccg    5760
gcgtcaatac gggataatac cgcgccacat agcagaactt taaaagtgct catcattgga    5820
aaacgttctt cggggcgaaa actctcaagg atcttaccgc tgttgagatc cagttcgatg    5880
taacccactc gtgcacccaa ctgatcttca gcatctttta ctttcaccag cgtttctggg    5940
tgagcaaaaa caggaaggca aaatgccgca aaaaagggaa taagggcgac acggaaatgt    6000
```

```
tgaatactca tactcttcct tttttcaatat tattgaagca tttatcaggg ttattgtctc    6060
atgagcggat acatatttga atgtatttag aaaaataaac aaatagggt tccgcgcaca     6120 tttccccgaa aagtgccacc tgacgtc                                        6147
```